US012780782B2

(12) United States Patent
Sudhakar et al.

(10) Patent No.: US 12,780,782 B2
(45) Date of Patent: Nov. 3, 2026

(54) AZIRINE CONTAINING COMPOUNDS AS ANTI-ANGIOGENESIS AGENTS AND A PROCESS FOR THE PREPARATION THEREOF

(71) Applicant: COUNCIL OF SCIENTIFIC & INDUSTRIAL RESEARCH, New Delhi (IN)

(72) Inventors: Gangarajula Sudhakar, Hyderabad (IN); Nagam Satish, Hyderabad (IN); Tella Ramesh Babu, Hyderabad (IN); Kumaravelu Jagavelu, Lucknow (IN); Himalaya Singh, Lucknow (IN); Mohammad Imran Siddiqi, Lucknow (IN); Muhammad Wahajuddin, Lucknow (IN); Sandeep Kumar Singh, Luknow (IN); Mamunur Rashid, Lucknow (IN); Anil Kumar Karunakaran Sasikala, Lucknow (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 872 days.

(21) Appl. No.: 18/007,960

(22) PCT Filed: Jun. 4, 2021

(86) PCT No.: PCT/IN2021/050544
§ 371 (c)(1),
(2) Date: Dec. 2, 2022

(87) PCT Pub. No.: WO2021/245705
PCT Pub. Date: Dec. 9, 2021

(65) Prior Publication Data

US 2023/0234920 A1 Jul. 27, 2023

(30) Foreign Application Priority Data

Jun. 4, 2020 (IN) ............................ 202011023422

(51) Int. Cl.

| | |
|---|---|
| ***C07D 203/04*** | (2006.01) |
| ***A61K 31/00*** | (2006.01) |
| ***A61P 9/00*** | (2006.01) |
| ***C07D 203/08*** | (2006.01) |
| ***C07D 203/26*** | (2006.01) |
| ***C07D 403/04*** | (2006.01) |
| ***C07D 403/06*** | (2006.01) |
| ***C07D 405/04*** | (2006.01) |
| ***C07D 405/06*** | (2006.01) |
| ***C07D 405/12*** | (2006.01) |
| ***C07F 9/564*** | (2006.01) |

(52) U.S. Cl.
CPC .............. *C07D 203/04* (2013.01); *A61P 9/00* (2018.01); *C07D 403/04* (2013.01); *C07D 403/06* (2013.01); *C07D 405/06* (2013.01); *C07D 405/12* (2013.01); *C07F 9/564* (2013.01)

(58) Field of Classification Search
CPC .. C07D 203/04; C07D 203/26; C07D 405/04; C07D 203/08; A61K 31/00
See application file for complete search history.

(56) References Cited

FOREIGN PATENT DOCUMENTS

KR 20057009447 A 5/2005

OTHER PUBLICATIONS

Harvey et al. (Journal of Organic Chemistry (1966), 31(12), 3907-10). Abstarct.*
Shin et al. (Chemistry Letters (1976), (10), 1063-6). Abstract.*
Sakamoto et al. Organic Letters (2011), 13(24), 6374-6377). Abstract.*
Hassner et al. (Journal of the American Chemical Society (1968), 90(11), 2869-75). Abstract.*
Qi et al. (Chemical Communications (Cambridge, United Kingdom) (2011), 47(27),7848-7850). Abstract.*
Skepper et al. (Bioorganic & Medicinal Chemistry Letters (2010), 20(6), 2029-2032.*
International Search Report mailed Sep. 7, 2021 in reference to co-pending Application No. PCT/IN2021/050544 filed Jun. 4, 2021.
Written Opinion mailed Sep. 7, 2021 in reference to co-pending Application No. PCT/IN2021/050544 filed Jun. 4, 2021.
Stapley, et al., "Microbial Production and Biological Characteristics", The Journal of Antibiotics, vol. 24, No. 1, pp. 42-47, Jan. 1971.
Miller, et al., "Isolation and Chemical Characterization as 3-Methyl-2(2H) Azirinecarboxylic Acid", The Journal of Antibiotics, vol. 24, No. 1, pp. 48-50, Jan. 1971.

(Continued)

*Primary Examiner* — Bruck Kifle
(74) *Attorney, Agent, or Firm* — DINSMORE & SHOHL LLP

(57) ABSTRACT

The present invention relates to azirine containing compounds useful as anti-angiogenesis agents and preparation thereof. Particularly the present invention relates to azirine containing compounds of formula I, Formula I wherein $R_1$, $R_2$ and $R_3$ are same as defined in the description. The compounds of the present invention are with asymmetric centers this, they are mixture of enantiomers and mixture of diastereomers in some cases. The present invention includes the individual enantiomers and diastereomeric forms of the compound formula I besides the mixtures thereof.

Formula I

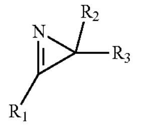

11 Claims, 10 Drawing Sheets

(56) References Cited

OTHER PUBLICATIONS

Molinski, et al., “Dysidazirine, a Cytotoxic Azacyclopropene from the Marine Sponge Dysidea fragilis”, Journal of Org. Chemistry, vol. 53, pp. 2103-2105, 1988.
Salomon, et al., “New Azacyclopropene Derivatives from Dysidea Fragilis Collected in Pohnpei”, Journal of Natural Products, vol. 58, No. 9, pp. 1463-1466, Sep. 1995.
Keffer, et al., “Motualevic Acids A-F, Antimicrobial Acids from the Sponge *Siliquariaspongia* sp.”, Organic Letters, vol. 11, No. 5, pp. 1087-1090, 2009.
Verstappen, et al., “Asymmetric Synthesis of 2H-Azirine Carboxylic Esters by an Alkaloid-Mediated Neber Reaction”, Journal of American Chem. Soc., vol. 188, pp. 8491-8492, 1996.
Qi, et al., “Facile synthesis of 2-alkyl/aryloxy-2H-azirines and their application in the synthesis of pyrroles”, Chem. Communication, vol. 48, pp. 3996-3998, 2012.
Jiang, et al., “Expedient Synthesis of Highly Substituted Pyrroles via Tandem Rearrangement of α-Diazo Oxime Ethers”, Journal of the American Chemical Society, vol. 134, pp. 4104-4107, 2012.
Sakamoto, et al., “Organocatalytic Asymmetric Neber Reaction for the Synthesis of 2H-Azirine Carboxylic Esters”, Organic Letters, vol. 13, No. 24, pp. 6374-6377, 2011.
Prechter, et al., “Gold-Catalyzed Synthesis of Functionalized Pyridines by Using 2H-Azirines as Synthetic Equivalents of Alkenyl Nitrenes”, Angewandte Communications Int. Ed., vol. 53, pp. 4959-4963, 2014.
Loy, et al., “Synthesis of Pyridines by Carbenoid-Mediated Ring Opening of 2H-Azirines”, Angewandte Comunications Int. Ed, vol. 52, pp. 2212-2216, 2013.
Kadam, et al., “Total Synthesis of motualevic acids A-F, (E) and (Z)-antizirines”, Tetrahedron, vol. 71, pp. 1058-1067, 2015.

* cited by examiner

AZIRINE CONTAINING COMPOUNDS AS ANTI-ANGIOGENESIS AGENTS AND A PROCESS FOR THE PREPARATION THEREOF

CROSS REFERENCES TO RELATED APPLICATIONS

This application is a national-stage application under 35 U.S.C. § 371 of International Application No. PCT/PCT/IN2021/050544, filed Jun. 4, 2021 which International Application claims benefit of priority to Indian patent application Ser. No. 20/201,1023422, filed Jun. 4, 2020.

FIELD OF THE INVENTION

The present invention relates to an azirine containing compound of formula I, an enantiomer, diastereoisomer, or a pharmaceutically acceptable salt thereof, to be useful as anti-angiogenesis agents.

Formula I

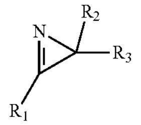

wherein $R_1$ is selected from alkyl ($C_1$-$C_{12}$); alkenyl ($C_1$-$C_{12}$), hydroxy, nitro, halogen, amino, cyano, aryl, heteroaryl, cycloalkyl ($C_1$-$C_7$), cyclo ether ($C_1$-$C_6$), heteroalkyl, alkoxy, alkylamino, aryl amino, alkyl ($C_1$-$C_{12}$) ester, (hetero)aryl ester, alkyl phosphonate, (hetero)aryl phosphonate, tetrazole;

$R_2$ and $R_3$ are either same or different and selected from the group consisting of H, $COOR_4$, cyano, tetrazole, phosphonate, alkoxybenzyl, hydroxy, nitro, halogen, amino, alkyl ($C_1$-$C_{12}$), aryl, heteroaryl, cycloalkyl ($C_1$-$C_7$), heteroalkyl, alkoxy, alkylamino, aryl amino, (hetero)aryl ester, alkyl phosphonate, (hetero)aryl phosphonate or tetrazole;

wherein each of these groups [R1, R2 and R3] may further substituted with one or more substituents selected from the group consisting of hydrogen, hydroxy, halogen, cyano, alkyl amino, aryl amino, alkoxy, amino, nitro, aldehyde, carboxylic acid, ester or phosphoester, (hetero)aryl,

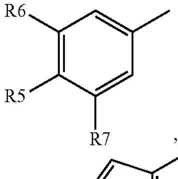
,
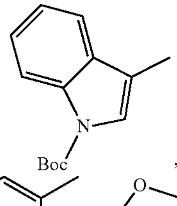
,
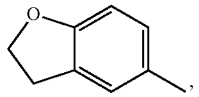
,
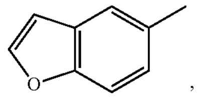
,
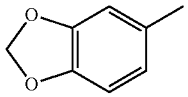
,
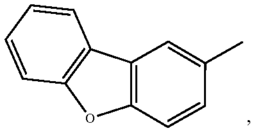
,
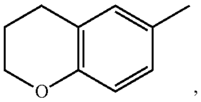
, -continued

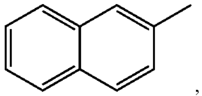
,
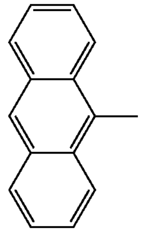

or 5-7 membered hetrocyclic ring wherein heteroatom is O, N or S.

R4 is selected from the group consisting of alkyl ($C_1$-$C_{12}$), allyl, methoxyethyl and benzyl;

$R_5$, $R_6$ and $R_7$ are either same or different and selected from the group consisting of H, OMe, H, CH3, t-butyl; Halogen (Cl, Br, F, I), OCF3, CN, OBu, vinyl; dimethylamino or

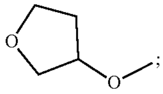
;

wherein R5 and R6 may be joined to form a 5 to 6 membered hetrocyclic ring.

Particularly, the present invention relates to a process for the preparation of azirine containing compounds of formula I.

BACKGROUND OF THE INVENTION

Azirine ring is the smallest nitrogen-containing heterocycle, and its existence in the natural products is remarkable. The first azirine containing natural product, azirinomicine, was isolated from a strain of the soil bacterium *Streptomyces aureus* (*J. Antibiot.* 1971, 24, 42-47; *J. Antibiot.* 1971, 24, 48-50). The long chain azirine carboxylic acid methyl ester, dysidazirines (*J. Org. Chem.* 1988, 53, 2103-2105, *J. Nat. Prod.* 1995, 58, 1463-1466) and terminal halogenated compounds, antazirines (*J. Nat. Prod.* 1995, 58, 1463-1466) were isolated from *Dysidea fragilis*. Recently, motualevic acid F along with antazirine were isolated from *Siliquariaspongia* sp. (*Org. Lett.* 2009, 11, 1087-1090). Apart from being in the natural products, azirine is also the reactive intermediate and serves as electrophile and nucleophile. Thus, it is widely used in the synthesis of several heterocycles such as pyrroles, indoles, and isoxazoles. The versatility of azirine ring prompted several research groups to develop synthetic methods, and the conventional methods such as thermolysis, photolysis of vinyl azides and Neber rearrangement of ketoxime tosylates are more often employed to access their synthesis. Although extensive efforts in developing methods for azirines and converting them into other heterocycles, the activity profiles of azirines are not up to far with other heterocycles, this is presumably the azirine ring erroneously assumed as an inherently unstable molecule. However, a very few numbers of azirine derivatives were synthesized and evaluated for various biological activities and found to exhibit prominent activities. The following are the references related to the invention. EP3053905, CH619706A5, CH619461A5, US20030027769; US20090317456; U.S. Pat. Nos. 7,872,029; 7,709,031; 6,664,272; 3,772,284; KR20050097494; EP0713393; EP0684820; US20070185069, U.S. Pat. No.

3,772,284, WO2013081549, U.S. Pat. No. 7,030,134, *J. Am. Chem. Soc.* 1996, 118, 8491-8492; U.S. Pat. Nos. 5,576,330; 6,025,353; *Chem. Commun.,* 2012, 48, 3996-3998; *J. Am. Chem. Soc.* 2012, 134, 4104-4107; *Org. Lett.,* 13, 24, 2011, 6374-6377; *Angew. Chem. Int. Ed.* 2014, 53, 4959-4963; *Angew. Chem. Int. Ed.* 2013, 52, 2212-2216; *Tetrahedron* 71, 2015, 1058-1067.

The existence of several natural products and their limited anti-microbial and cytotoxicity activity screening data prompted us to synthesize azirine containing compounds and evaluate their anti-angiogenesis activity. Angiogenesis is the formation of new blood vessels from pre-existing blood vessels which has a crucial role in wound healing and several diseases states such as diabetic retinopathy, rheumatoid arthritis, cancers, etc. Inhibition of blood vessel growth through anti-angiogenesis technique is a promising strategy to cure diseases like cancers. Over last few decades, researchers have been developing several drug inhibitors and monoclonal antibodies to stop the angiogenesis process in cancer. However, the emergence of drug resistance, low bioavailability, and other factors limit their use for effective treatment. Therefore, potent anti-angiogenic molecules are currently in demand to cure malignant tumors. Cancer research always requires the discovery of new drugs that inhibit tumor growth by attenuation of blood vessel formation. In this context a library of azirine containing compounds with diverse structural features have been synthesized and evaluated for their anti-angiogenesis potential. We have found highly potent lead molecule for anti-angiogenic activity based on in vitro and in vivo experiments. In primary studies, the compound shows better efficacy as compared to Sunitinib.

OBJECTS OF THE INVENTION

The main objective of the present invention is to provide an azirine containing compound of formula I.

Another objective of the present invention is to provide a process for the preparation of azirine containing compound of formula I.

Yet another objective of the present invention is to provide azirine containing compound of formula I, useful as anti-angiogenesis agents.

SUMMARY OF THE INVENTION

Accordingly, the present invention provides an Azirine containing compound of formula I, an enantiomer, diastereoisomer, a pharmaceutically acceptable salt or a mixture thereof, Formula I

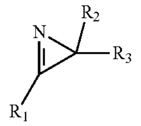

wherein $R_1$ is selected from alkyl ($C_1$-$C_{12}$); alkenyl ($C_1$-$C_{12}$), hydroxy, nitro, halogen, amino, cyano, aryl, heteroaryl, cycloalkyl ($C_1$-$C_7$), cyclo ether ($C_1$-$C_6$), heteroalkyl, alkoxy, alkylamino, aryl amino, alkyl ($C_1$-$C_{12}$) ester, (hetero)aryl ester, alkyl phosphonate, (hetero)aryl phosphonate, tetrazole;

$R_2$ and $R_3$ are either same or different and selected from the group consisting of H, $COOR_4$, cyano, tetrazole, phosphonate, alkoxybenzyl, hydroxy, nitro, halogen, amino, alkyl ($C_1$-$C_{12}$), aryl, heteroaryl, cycloalkyl ($C_1$-$C_7$), heteroalkyl, alkoxy, alkylamino, aryl amino, (hetero)aryl ester, alkyl phosphonate, (hetero)aryl phosphonate or tetrazole;

wherein each of these groups [R1, R2 and R3] may further substituted with one or more substituents selected from the group consisting of hydrogen, hydroxy, halogen, cyano, alkyl amino, aryl amino, alkoxy, amino, nitro, aldehyde, carboxylic acid, ester or phosphoester, (hetero)aryl;

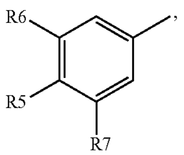
,
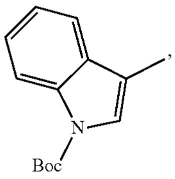
,
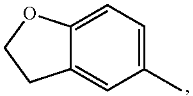
,
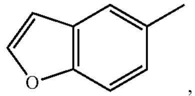
,
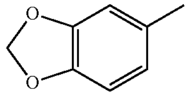
,
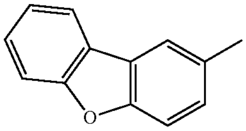
,
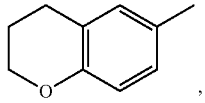
,
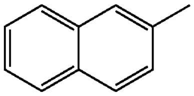
,
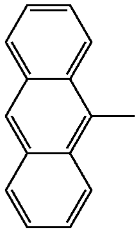

or 5-7 membered hetrocyclic ring wherein heteroatom is O, N or S, wherein R4 is selected from the group consisting of alkyl ($C_1$-$C_{12}$), allyl, methoxyethyl and benzyl;

$R_5$, $R_6$, $R_7$ are either same or different and selected from the group consisting of H, OMe, CH3, t-butyl, halogen, OCF3, CN, OBu, vinyl, dimethylamino and

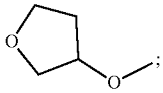
;

wherein the halogen is selected from the group consisting of chlorine (Cl), bromine (Br), fluorine (F) and iodine (I);

wherein R5 and R6 is optionally joined to form a 5 to 6 membered hetrocyclic ring.

In an embodiment of the present invention, the compound of formula I is selected from the group consisting of:

i. Ethyl 3-(4-methoxyphenethyl)-2H-azirine-2-carboxylate (1);

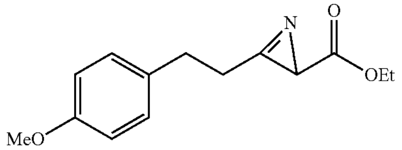 [SMILES: CCOC(=O)C1N=C1CCc1ccc(OC)cc1]

ii. Ethyl 3-(pent-4-en-1-yl)-2H-azirine-2-carboxylate (2);

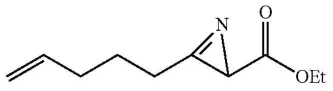

iii. Ethyl 3-dodecyl-2H-azirine-2-carboxylate (3);

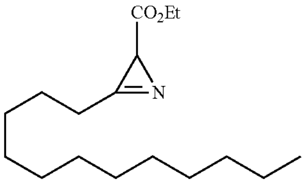 [SMILES: CCCCCCCCCCCCC1=NC1C(=O)OCC]

iv. Ethyl 3-(4-methylpent-3-en-1-yl)-2H-azirine-2-carboxylate (4);

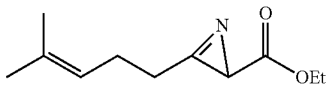

v. Ethyl (E)-3-(4,8-dimethylnona-3,7-dien-1-yl)-2H-azirine-2-carboxylate (5);

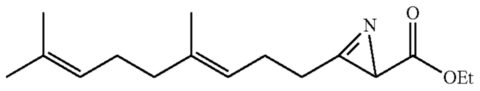 [SMILES: CCOC(=O)C1N=C1CC/C=C(\C)CCC=C(C)C]

vi. Ethyl 3-phenethyl-2H-azirine-2-carboxylate (6);

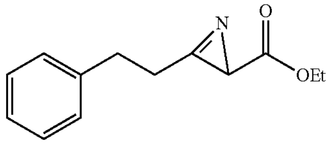 [SMILES: CCOC(=O)C1N=C1CCc1ccccc1]

vii. Ethyl 3-(4-methylphenethyl)-2H-azirine-2-carboxylate (7);

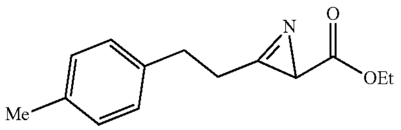 [SMILES: CCOC(=O)C1N=C1CCc1ccc(C)cc1]

viii. Ethyl 3-(4-chlorophenethyl)-2H-azirine-2-carboxylate (8);

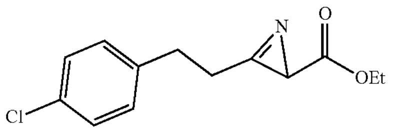 [SMILES: CCOC(=O)C1N=C1CCc1ccc(Cl)cc1]

ix. Ethyl 3-(4-(tert-butyl)phenethyl)-2H-azirine-2-carboxylate (9);

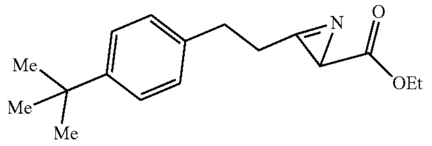 [SMILES: CCOC(=O)C1N=C1CCc1ccc(C(C)(C)C)cc1]

x. Ethyl 3-(4-fluorophenethyl)-2H-azirine-2-carboxylate (10);

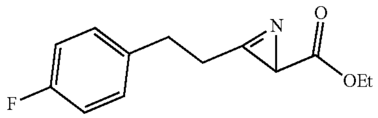 [SMILES: CCOC(=O)C1N=C1CCc1ccc(F)cc1]

xi. Ethyl (E)-3-(4-phenylbut-3-en-1-yl)-2H-azirine-2-carboxylate (11);

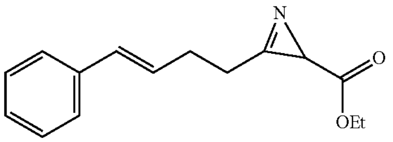 [SMILES: CCOC(=O)C1N=C1CC/C=C/c1ccccc1]

xii. Ethyl 3-(3,4,5-trimethoxyphenethyl)-2H-azirine-2-carboxylate (12);

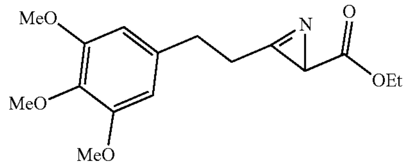 [SMILES: CCOC(=O)C1N=C1CCc1cc(OC)c(OC)c(OC)c1]

xiii. Ethyl (E)-3-(4-methoxystyryl)-2H-azirine-2-carboxylate (13);

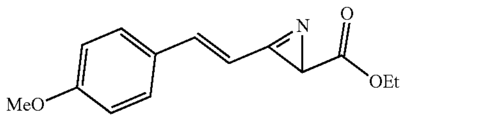 [SMILES: CCOC(=O)C1N=C1/C=C/c1ccc(OC)cc1]

xiv. Methyl 3-(4-methoxyphenethyl)-2H-azirine-2-carboxylate (14);

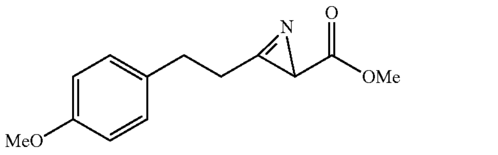 [SMILES: COC(=O)C1N=C1CCc1ccc(OC)cc1]

xv. Ethyl 3-(4-bromophenethyl)-2H-azirine-2-carboxylate (15);

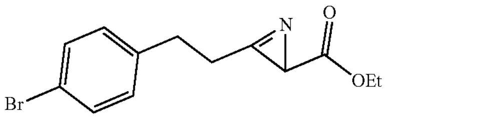 [SMILES: CCOC(=O)C1N=C1CCc1ccc(Br)cc1]

xvi. Ethyl 3-(4-iodophenethyl)-2H-azirine-2-carboxylate (16);

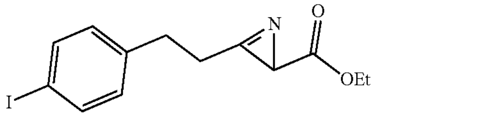 [SMILES: CCOC(=O)C1N=C1CCc1ccc(I)cc1]

xvii. tert-Butyl 3-(4-methoxyphenethyl)-2H-azirine-2-carboxylate (17);

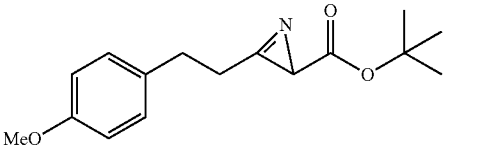 [SMILES: COc1ccc(CCC2=NC2C(=O)OC(C)(C)C)cc1]

xviii. Benzyl 2-(4-methoxybenzyl)-3-methyl-2H-azirine-2-carboxylate (18);

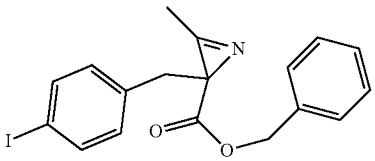 [SMILES: CC1=NC1(Cc1ccc(I)cc1)C(=O)OCc1ccccc1]

xix. Propyl 3-(4-methoxyphenethyl)-2H-azirine-2-carboxylate (19);

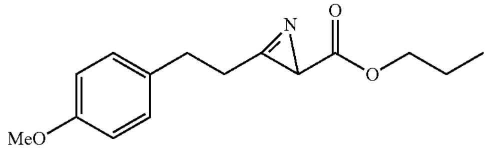 [SMILES: CCCOC(=O)C1N=C1CCc1ccc(OC)cc1]

xx. Isopropyl 3-(4-methoxyphenethyl)-2H-azirine-2-carboxylate (20);

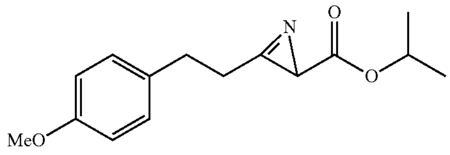 [SMILES: COc1ccc(CCC2=NC2C(=O)OC(C)C)cc1]

xxi. Isobutyl 3-(4-methoxyphenethyl)-2H-azirine-2-carboxylate (21);

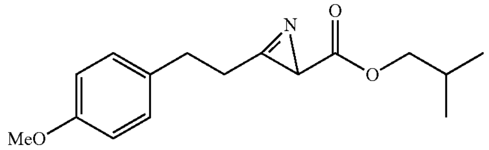 [SMILES: COc1ccc(CCC2=NC2C(=O)OCC(C)C)cc1]

xxii. sec-Butyl 3-(4-methoxyphenethyl)-2H-azirine-2-carboxylate (21);

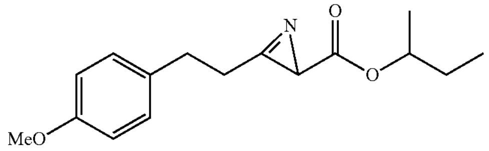 [SMILES: CCC(C)OC(=O)C1N=C1CCc1ccc(OC)cc1]

xxiii. Pentyl 3-(4-methoxyphenethyl)-2H-azirine-2-carboxylate (23);

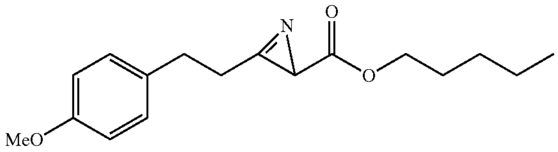 [SMILES: CCCCCOC(=O)C1N=C1CCc1ccc(OC)cc1]

xxiv. Isopentyl 3-(4-methoxyphenethyl)-2H-azirine-2-carboxylate (24);

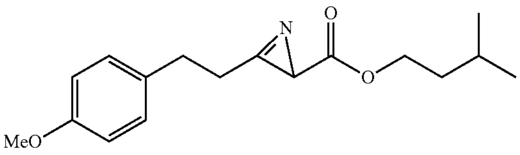 [SMILES: COc1ccc(CCC2=NC2C(=O)OCCC(C)C)cc1]

xxv. 2-Methoxyethyl 3-(4-methoxyphenethyl)-2H-azirine-2-carboxylate (25);

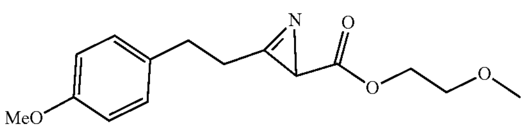 [SMILES: COCCOC(=O)C1N=C1CCc1ccc(OC)cc1]

xxvi. Allyl 3-(4-methoxyphenethyl)-2H-azirine-2-carboxylate (26);

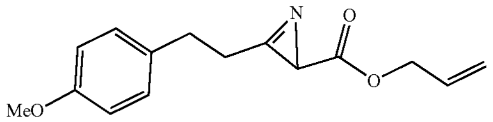 [SMILES: C=CCOC(=O)C1N=C1CCc1ccc(OC)cc1]

xxvii. Ethyl 3-(2-(naphthalen-2-yl)ethyl)-2H-azirine-2-carboxylate (27);

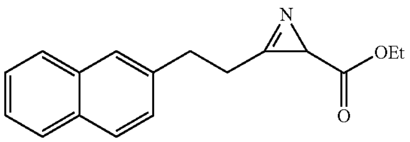 [SMILES: CCOC(=O)C1N=C1CCc1ccc2ccccc2c1]

xxviii. Ethyl 3-(4-(trifluoromethoxy)phenethyl)-2H-azirine-2-carboxylate (28);

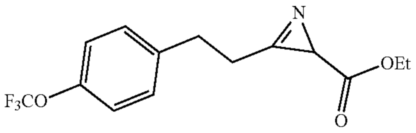 [SMILES: CCOC(=O)C1N=C1CCc1ccc(OC(F)(F)F)cc1]

xxix. Octyl 3-(4-methoxyphenethyl)-2H-azirine-2-carboxylate (29);

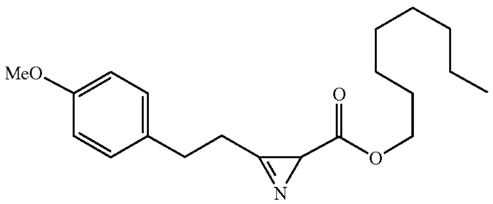 [SMILES: CCCCCCCCOC(=O)C1N=C1CCc1ccc(OC)cc1]

xxx. Ethyl 3-(2-(tetrahydrofuran-2-yl)ethyl)-2H-azirine-2-carboxylate (30);

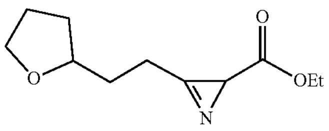 [SMILES: CCOC(=O)C1N=C1CCC1CCCO1]

xxxi. Ethyl 3-(4-cyanophenethyl)-2H-azirine-2-carboxylate (31);

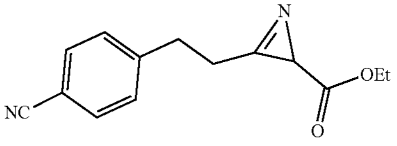 [SMILES: CCOC(=O)C1N=C1CCc1ccc(C#N)cc1]

xxxii. Ethyl 3-(4-butoxyphenethyl)-2H-azirine-2-carboxylate (32);

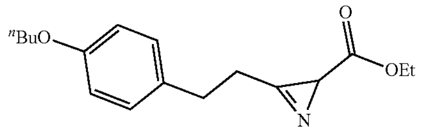

xxxiii. Ethyl 3-(2-(anthracen-9-yl)ethyl)-2H-azirine-2-carboxylate (33);

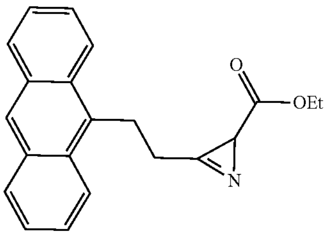 [SMILES: CCOC(=O)C1N=C1CCc1c2ccccc2cc2ccccc12]

xxxiv. Ethyl 3-(3,4-dimethoxyphenethyl)-2H-azirine-2-carboxylate (34);

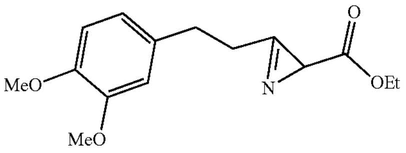 [SMILES: CCOC(=O)C1N=C1CCc1ccc(OC)c(OC)c1]

xxxv. Diethyl 3-(4-methoxyphenethyl)-2H-azirine-2,2-dicarboxylate (35);

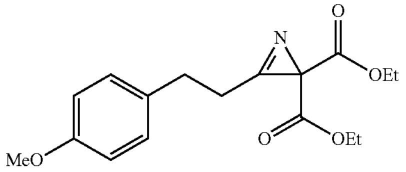 [SMILES: CCOC(=O)C1(C(=O)OCC)N=C1CCc1ccc(OC)cc1]

xxxvi. Ethyl 3-(4-vinylphenethyl)-2H-azirine-2-carboxylate (36);

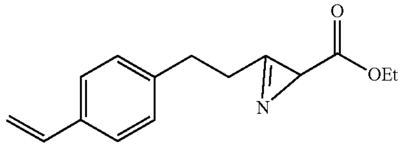 [SMILES: C=Cc1ccc(CCC2=NC2C(=O)OCC)cc1]

xxxvii. Ethyl-3-(3-(2,3-dihydrobenzofuran-5-yl)propyl)-2H-azirine-2-carboxylate (37);

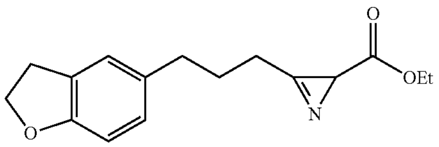 [SMILES: CCOC(=O)C1N=C1CCCc1ccc2c(c1)CCO2]

xxxviii. tert-Butyl-3-(2-(2-(ethoxycarbonyl)-2H-azirin-3-yl)ethyl)-1H-indole-1-carboxylate (38);

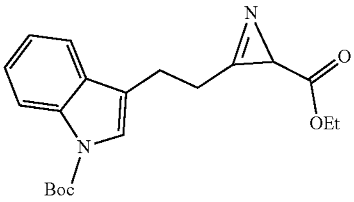 [SMILES: CCOC(=O)C1N=C1CCc1cn(C(=O)OC(C)(C)C)c2ccccc12]

xxxix. Ethyl 3-(2-(2,3-dihydrobenzofuran-5-yl)ethyl)-2H-azirine-2-carboxylate (39);

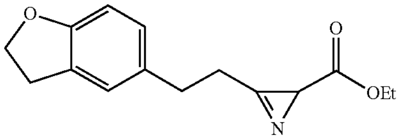 [SMILES: CCOC(=O)C1N=C1CCc1ccc2c(c1)CCO2]

xl. Ethyl-3-(3-(benzofuran-5-yl)propyl)-2H-azirine-2-carboxylate (40);

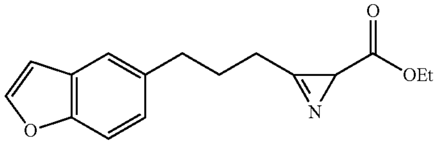 [SMILES: CCOC(=O)C1N=C1CCCc1ccc2occc2c1]

xli. Ethyl 3-(2-(benzo[d][1,3]dioxol-5-yl)ethyl)-2H-azirine-2-carboxylate (41);

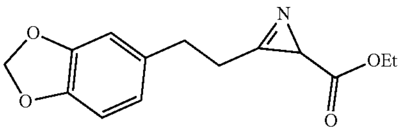 [SMILES: CCOC(=O)C1N=C1CCc1ccc2c(c1)OCO2]

xlii. Ethyl 3-(4-(2,3-dihydrobenzofuran-5-yl)butyl)-2H-azirine-2-carboxylate (42);

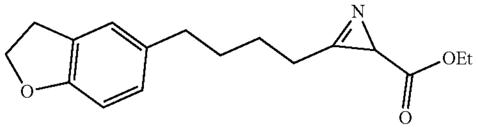 [SMILES: CCOC(=O)C1N=C1CCCCc1ccc2c(c1)CCO2]

xliii. Ethyl 3-(3-(benzo[d][1,3]dioxol-5-yl)propyl)-2H-azirine-2-carboxylate (43);

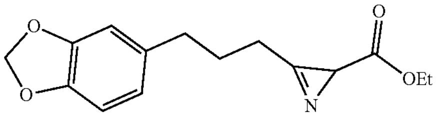 [SMILES: CCOC(=O)C1N=C1CCCc1ccc2c(c1)OCO2]

xliv. Ethyl 3-(3-(dibenzo[b,d]furan-2-yl)propyl)-2H-azirine-2-carboxylate (44);

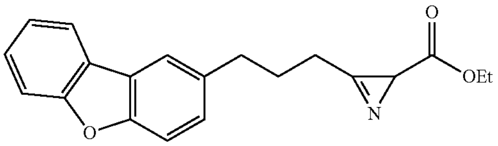 [SMILES: CCOC(=O)C1N=C1CCCc1ccc2oc3ccccc3c2c1]

xlv. Ethyl 3-(3-(chroman-6-yl)propyl)-2H-azirine-2-carboxylate (45);

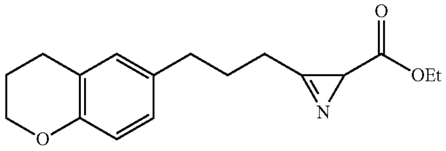 [SMILES: CCOC(=O)C1N=C1CCCc1ccc2c(c1)CCCO2]

xlvi. Ethyl (E)-3-(4-(dimethylamino)styryl)-2H-azirine-2-carboxylate (46);

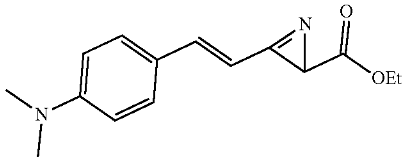 [SMILES: CCOC(=O)C1N=C1/C=C/c1ccc(N(C)C)cc1]

xlvii. Ethyl 3-(4-(dimethylamino)phenethyl)-2H-azirine-2-carboxylate (47);

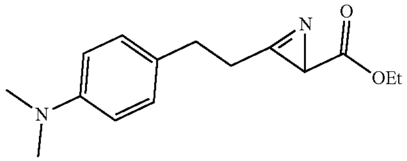 [SMILES: CCOC(=O)C1N=C1CCc1ccc(N(C)C)cc1]

xlviii. 3-(4-Methoxyphenethyl)-2H-azirine-2-carbonitrile (48);

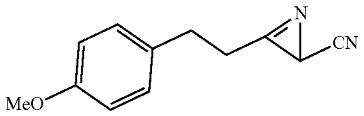 [SMILES: COc1ccc(CCC2=NC2C#N)cc1]

xlix. Diethyl (3-(4-methoxyphenethyl)-2H-azirin-2-yl) phosphonate (49);

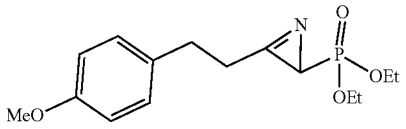 [SMILES: CCOP(=O)(OCC)C1N=C1CCc1ccc(OC)cc1]

l. Ethyl 3-(4-((tetrahydrofuran-3-yl)oxy)phenethyl)-2H-azirine-2-carboxylate (50);

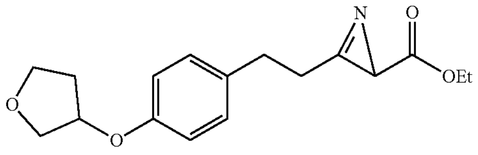 [SMILES: CCOC(=O)C1N=C1CCc1ccc(OC2CCOC2)cc1]

li. 5-(3-(4-Methoxyphenethyl)-2H-azirin-2-yl)-1H-tetrazole (51).

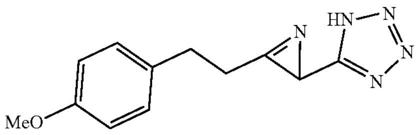 [SMILES: COc1ccc(CCC2=NC2c2nnn[nH]2)cc1]

In yet another embodiment, the present invention provides a pharmaceutical composition comprising the compound of formula I along with pharmaceutically acceptable excipients and pharmaceutically acceptable salts thereof.

In yet another embodiment of present invention, the excipients are selected from the group consisting of Carboxy methyl cellulose, tween 20, polyethylene glycol (PEG 400), dimethyl formamide (DMF) and olive oil.

In yet another embodiment of present invention, the salts are selected from salts of basic or acidic groups present in compounds of the invention and basic salts are selected from the group consisting of aluminum, calcium, lithium, magnesium, potassium or sodium and acidic salts are selected from the group consisting of hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate or p-toluenesulfonate.

In yet another embodiment, present invention provides a process for the preparation of Azirine containing compound of formula I comprising the steps of:

a) treating a beta-keto ester compound of formula II with hydroxylamine salt and an amine base in alcoholic solvent at temperature in the range of −5 to 5° C. for period in the range of 6-12 h to obtain oxime compound of formula III;

Formula II

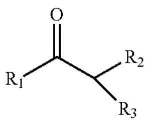

-continued

Formula III

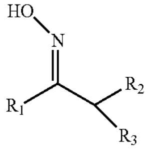

wherein $R_1$, R2 and R3 are same as defined above;

a) treating oxime compound of formula III as obtained in step (a), with p-toluenesulfonic anhydride and an amine base in organic solvent at temperature in the range of −5 to 5° C. for a time period in the range of 6-12 h to obtain a tosyloxime compound of formula IV;

IV

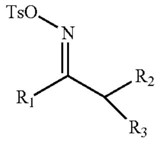

wherein $R_1$, R2 and R3 are same as defined above;

b) treating tosyloxime compound of formula IV obtained in step (b), with an amine base in organic solvent at temperature in the range of −5 to 5° C. for period in the range of 6-12 h to obtain the azirine containing compound of formula I;

c) optionally treating oxime compound of formula III as obtained in step (a) with p-toluenesulfonyl chloride and an amine base in organic solvent at temperature in the range of −5 to 35° C. for period in the range of 6-12 h to obtain the azirine containing compound of formula I.

In yet another embodiment of present invention, the amine base is selected from the group consisting of pyridine, triethylamine, pyrrolidine or imidazole.

In yet another embodiment of present invention, the organic solvent is selected from the group consisting of toluene, tetrahydrofuran, dioxin, dichloromethane, chloroform, hexane, pentane, heptane or acetonitrile and alcoholic solvent is selected from the group consisting of methanol, ethanol, propanol, butanol or isopropanol.

In yet another embodiment, present invention provides a method of treating angiogenesis comprises administering the compound of formula I or the pharmaceutical composition comprising the compound of formula I, to a subject in need thereof.

In yet another embodiment of present invention, said compounds are useful as anti-angiogenesis.

In yet another embodiment of present invention, said compounds are useful as anti-angiogenesis for the treatment of eye disorders, macular degeneration and reduce intraocular pressure.

In yet another embodiment, present invention provides use of compound of formula I for the treatment of abnormal angiogenesis.

DETAILS OF THE BIOLOGICAL MATERIALS USED

Figure 1:
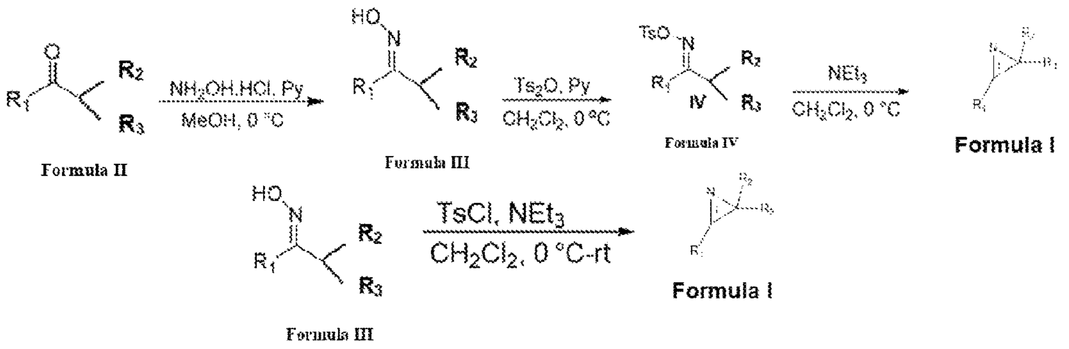
FIG. 1 represents synthesis of azirine containing compounds of formula I.

Olive Oil used in the present invention was purchased from Sigma Aldrich Ltd (St Louis, USA).

DETAILED DESCRIPTION OF THE INVENTION

Present invention provides an azirine containing compound of formula I, which have been synthesized by diverse functional modifications with azirine as the basic core. Accordingly, the present invention affords a new class of azirine containing compounds of formula I, Formula I

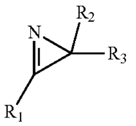

wherein $R_1$ is selected from alkyl ($C_1$-$C_{12}$); alkenyl ($C_1$-$C_{12}$), hydroxy, nitro, halogen, amino, cyano, aryl, heteroaryl, cycloalkyl ($C_1$-$C_7$), cyclo ether ($C_1$-$C_6$), heteroalkyl, alkoxy, alkylamino, aryl amino, alkyl ($C_1$-$C_{12}$) ester, (hetero)aryl ester, alkyl phosphonate, (hetero)aryl phosphonate, tetrazole;

$R_2$ and $R_3$ are either same or different and selected from the group consisting of H, $COOR_4$, cyano, tetrazole, phosphonate, alkoxybenzyl, hydroxy, nitro, halogen, amino, alkyl ($C_1$-$C_{12}$), aryl, heteroaryl, cycloalkyl ($C_1$-$C_7$), heteroalkyl, alkoxy, alkylamino, aryl amino, (hetero)aryl ester, alkyl phosphonate, (hetero)aryl phosphonate or tetrazole;

wherein each of these groups [R1, R2 and R3] may further substituted with one or more substituents selected from the group consisting of hydrogen, hydroxy, halogen, cyano, alkyl amino, aryl amino, alkoxy, amino, nitro, aldehyde, carboxylic acid, ester or phosphoester, (hetero)aryl;

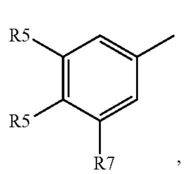 , 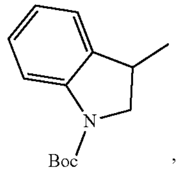 , 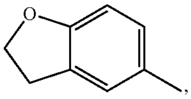 , 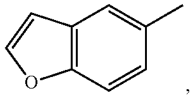 , 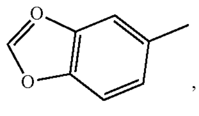 , 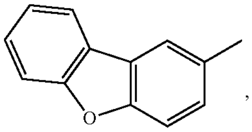 , 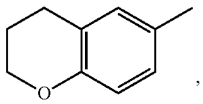 , 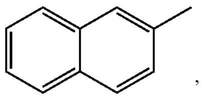 , 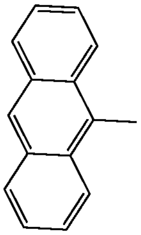

or 5-7 membered hetrocyclic ring wherein heteroatom is O, N or S.

R4 is selected from the group consisting of alkyl ($C_1$-$C_{12}$), allyl, Methoxyethyl; benzyl;

$R_5$ $R_6$ and $R_7$ are either same or different and selected from the group consisting of H, OMe; H, CH3, t-butyl; Halogen (Cl, Br, F, I), OCF3, CN, OBu, vinyl; dimethylamino or

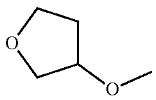

R5 and R6 may be joined to form a 5 to 6 membered hetrocyclic ring.

The compounds of the present invention are with asymmetric centers; thus, they are mixture of enantiomers and mixture of diastereomers in some cases. The present invention includes the individual enantiomers and diastereomeric forms of the compound formula I besides the mixtures thereof.

The present invention also provides a process for the preparation of azirine containing compound of formula I.

A large number of various azirine containing compounds possessing diversely substituted architecture were found to exhibit several biological properties. These functionalities are prominent structural motifs of new medicines from different pharmacological groups. The development of new structural scaffolds of azirine containing architecture is very important for the drug discovery process. In this connection a large number of azirine containing compounds were developed as depicted in the formula I. The processes for the synthesis of these azirine containing compounds involve operationally simple and highly efficient improved synthetic protocol giving rise to the desired products in high yields.

A process for the preparation of azirine containing compound of formula I wherein the said process comprising the steps of:

a) treating beta-keto ester compound of formula II with hydroxylamine salt and an amine base in alcoholic solvent at temperature in the range of −5 to 5° C. for period in the range of 6-12 h to obtain oxime compound of formula III;

b) treating oxime compound of formula III obtained in step-a, with p-toluenesulfonic anhydride and an amine base in organic solvent at temperature in the range of −5 to 5° C. for period in the range of 6-12 h to obtain tosyloxime compound of formula IV;

c) treating tosyloxime compound of formula IV obtained in step-b, with an amine base in organic solvent at temperature in the range of −5 to 5° C. for period in the range of 6-12 h to obtain azirine containing compound of formula I.

d) monitoring of the reaction by thin layer chromatography or HPLC methods;

e) reaction workup using solvent extraction methods; and f) purification of the product by column chromatography.

Optionally, the process steps (b) and (c) can also be performed in one-pot operation using p-toluenesulfonyl chloride and an amine base in organic solvent at temperature in the range of −5 to 35° C. for period in the range of 6-12 h to obtain azirine containing compound of formula I.

The amine base used is selected from the group consisting of pyridine, triethylamine, pyrrolidine or imidazole.

The alcoholic solvents used is selected from the group consisting of methanol, ethanol, propanol, butanol or isopropanol either alone or combination thereof.

The organic solvent used is selected from the group consisting of toluene, tetrahydrofuran, dioxin, dichloromethane, chloroform, hexane, pentane, heptane or acetonitrile either alone or combination thereof.

All the products are purified by column chromatography.

Biological Activity

Azirine containing compounds are efficient structural motifs capable of showing diverse biological activities. The azirine containing compounds prepared are tested for anti-angiogenesis activity and in this study, compound 1 possessed an effective and potent anti-angiogenic activity on primary tubulogenesis screening (75 nM) and 3D angiogenesis screening (250 nm) activity. This compound showed its anti-angiogenic activity in different models such as matrigel implantation assay, CAM and ear angiogenesis assay. The compound 1 inhibits the tumor growth in the in vivo xenograft mouse model both in the intramuscular and intra peritoneal injection 25 mg/kg compound. Further, the compound 1 partially inhibits the expression of VEGFR2 and SRC kinase expression. The compound 1 also inhibited angiogenesis through its binding of the ligand endothelin. In total, the compound 1 is a potent inhibitor angiogenesis with a new target.

EXAMPLES

Following examples are given by way of illustration and therefore should not be construed to limit the scope of the invention.

Example 1

General Procedure for the Synthesis of Compound of Formula III

To a solution of compound II (1 g, 4.00 mmol) in methanol (7.9 mL) was added hydroxylamine hydrochloride (0.568 g, 12.00 mmol) at 0° C. Then, pyridine (0.3 mL, 4.40 mmol) was added and stirred until completion of the reaction. Upon completion, the crude mixture was quenched with cold water and extracted with EtOAc. The combined organic layers were washed with brine, dried over $Na_2SO_4$, filtered and concentrated in vacuo and the crude material III was used in the next step.

Example 2

General Procedure for the Synthesis of Compound of Formula IV

To a solution of E/Z-isomers of ketoxime III (1.2 g, 4.528 mmol) in dichloromethane (9 mL) was added p-toluenesulfonic anhydride (1.77 g, 5.434 mmol) at 0° C. Then, pyridine (0.4 mL, 4.981 mmol) was added and stirred the reaction mixture at room temperature. Upon completion, the reaction mixture was quenched with cold water and extracted with EtOAc. The combined organic layers were washed with brine, dried over $Na_2SO_4$, filtered and concentrated in vacuo and purified by using silica gel column chromatography (10% EtOAc/hexane) to yield IV (0.85 g, 47%) ($R_f$=0.6, 20% EtOAc/hexane). Conversion of the hydroxyl group to a leaving group is also achieved from other reagents such as acetic anhydride, acyl chloride, 2,4,6-triisopropylbenzenesulfonyl chloride, 2,4,6-triisopropylbenzenesulfonyl anhydride, and tosyl chloride.

Example 3

General Procedure for the Synthesis of Compound of Formula I

To a solution of E/Z isomers of compound IV (0.85 g, 2.028 mmol) in dichloromethane (4 mL) was added triethylamine (1.12 mL, 8.145 mmol) and stirred at 0° C. Upon completion, the reaction mixture was quenched with cold water and extracted with EtOAc. The combined organic layers were washed with brine, dried over $Na_2SO_4$, filtered and concentrated in vacuo and purified by using silica gel column chromatography (7% EtOAc/hexane) to give I (0.24 g, 48%) $R_f$=0.5, 20% EtOAc/hexane).

Example 4

General Procedure for the Synthesis of Compound of Formula I From Compound of Formula III To a solution of E/Z-isomers of ketoxime III (1.2 g, 4.528 mmol) in dichloromethane (9 mL) was added p-toluenesulfonyl chloride (1 g, 5.433 mmol) at 0° C., followed by triethylamine (2.5 mL, 18.113 mmol) at 0° C. Then, the reaction mixture was stirred, and upon completion, the crude reaction mixture was quenched with cold water and extracted with EtOAc. The combined organic layers were washed with brine, dried over $Na_2SO_4$, filtered and concentrated in vacuo and purified by using silica gel column chromatography (7% EtOAc/hexane) to give the compound I (0.642 g, 58%) $R_f$=0.5, 20% EtOAc/hexane).

Example 5

Ethyl 3-(4-methoxyphenethyl)-2H-azirine-2-carboxylate (1) Compound 1 was synthesized from the corresponding keto-compound following the general procedure. Yield: 48% as pale yellow color oil $R_f$=0.5 (20% EtOAc/hexane); $^1$H NMR (400 MHz, $CDCl_3$): δ (ppm) 7.15 (d, J=8.6 Hz, 2H), 6.85 (d, J=8.6 Hz, 2H), 4.24-4.08 (m, 2H), 3.79 (s, 3H), 3.16-3.07 (m, 2H), 3.07-2.96 (m, 2H), 2.42 (s, 1H), 1.26 (t, J=7.2 Hz, 3H); $^{13}$C NMR (100 MHz, $CDCl_3$): δ (ppm) 171.9, 161.7, 158.3, 131.2, 129.1, 114.0, 61.0, 55.1, 29.4, 28.9, 28.6, 14.1; IR (Neat): $\nu_{max}$ 2982, 2936, 2836, 1790, 1721, 1611, 1512, 1464, 1444, 1369, 1333, 1245, 1176, 1107, 1030, 972, 822, 789, 701 $cm^{-1}$; Mass (m/z): 248.15 $(M+H)^+$ (calculated for $C_{14}H_{17}NO_3$: M 247.1208); HPLC: 99% (Purity).

Example 6

Ethyl 3-(pent-4-en-1-yl)-2H-azirine-2-carboxylate (2)

Yield: 32% $R_f$=0.5 (10% EtOAc/hexane); $^1$H NMR (400 MHz, $CDCl_3$): δ (ppm) 5.8 (m, 1H), 5.1-5.0 (m, 2H), 4.3-4.12 (m, 2H), 2.85 (m, 2H), 2.42 (s, 1H), 2.25 (m, 2H), 1.9-1.8 (m, 2H), 1.24 (t, J=7.2 Hz, 3H); $^{13}$C NMR (75 MHz, $CDCl_3$): δ (ppm) 172.1, 161.9, 136.8, 116.1, 61.0, 32.7, 28.7, 25.9, 23.3, 14.2; IR (Neat): $\nu_{max}$ 3447, 3078, 2923, 2853, 1782, 1728, 1370, 1334, 1285, 1193, 1035, 994, 916, 772 $cm^{-1}$; Mass (m/z): 182.20 $(M+H)^+$ (calculated for $C_{10}H_{15}NO_2$: M 181.1102).

Example 7

Ethyl 3-dodecyl-2H-azirine-2-carboxylate (3)

Yield: 28% $R_f$=0.5 (10% EtOAc/hexane); $^1$H NMR (400 MHz, $CDCl_3$): δ (ppm) 4.25-4.05 (m, 2H), 2.8 (m, 2H), 2.42 (s, 1H), 1.8-1.6 (m, 2H), 1.5-1.0 (m, 21H), 0.9 (t, J=7.0 Hz, 3H); $^{13}$C NMR (75 MHz, $CDCl_3$): δ (ppm) 172.1, 162.0, 61.0, 31.8, 29.5, 29.5, 29.3, 29.2, 29.0, 28.7, 26.7, 24.2, 22.6, 14.1; IR (Neat): $\nu_{max}$ 3446, 2925, 2854, 1791, 1731, 1463, 1333, 1283, 1188, 1036, 974, 770 $cm^{-1}$; Mass (m/z): 282.25 $(M+H)^+$ (calculated for $C_{17}H_{31}NO_2$: M 281.2354).

Example 8

Ethyl 3-(4-methylpent-3-en-1-yl)-2H-azirine-2-carboxylate (4)

Yield: 31% $R_f$=0.5 (10% EtOAc/hexane); $^1$H NMR (400 MHz, $CDCl_3$): δ (ppm) 5.15 (m, 1H), 4.3-4.1 (m, 2H), 2.8 (m, 2H), 2.45 (m, 2H), 2.42 (s, 1H), 1.7 (s, 3H), 1.6 (s, 3H), 1.25 (t, J=7.0 Hz, 3H); $^{13}$C NMR (75 MHz, $CDCl_3$): δ (ppm) 172.1, 161.9, 134.2, 121.3, 61.0, 28.8, 27.0, 25.6, 22.9, 17.7, 14.2; IR (Neat): $\nu_{max}$ 3447, 2925, 2859, 1727, 1635, 1455, 1374, 1333, 1263, 1193, 1036, 759, 573 $cm^{-1}$; Mass (m/z): 196.15 $(M+H)^+$ (calculated for $C_{11}H_{17}NO_2$: M 195.1259).

Example 9

Ethyl (E)-3-(4, 8-dimethylnona-3, 7-dien-1-yl)-2H-azirine-2-carboxylate (5) Yield: 30% $R_f$=0.5 (10% EtOAc/hexane); $^1$H NMR (400 MHz, $CDCl_3$): δ (ppm) 5.15 (m, 1H), 5.05 (m, 1H), 4.25-4.20 (m, 2H), 2.8 (m, 2H), 2.45 (m, 2H), 2.42 (s, 1H), 2.1-2.0 (m, 2H), 2.0-1.9 (m, 2H), 1.69 (s, 3H), 1.62 (s, 3H), 1.6 (s, 3H), 1.26 (t, J=7.0 Hz, 3H); $^{13}$C NMR (75 MHz, $CDCl_3$): δ (ppm) 171.8, 161.6, 137.4, 131.1, 123.7, 121.0, 60.7, 39.3, 28.6, 26.7, 26.2, 25.4, 22.6, 17.4, 15.8, 13.9; IR (Neat): $\nu_{max}$ 3444, 2975, 2925, 1791, 1728, 1662, 1372, 1333, 1285, 1192, 1100, 1036, 973, 768 $cm^{-1}$; Mass (m/z): 264.25 $(M+H)^+$ (calculated for $C_{16}H_{25}NO_2$: M 263.1885).

Example 10

Ethyl 3-phenethyl-2H-azirine-2-carboxylate (6)

Yield: 49% as colorless oil $R_f$=0.5 (20% EtOAc/hexane); $^1$H NMR (400 MHz, $CDCl_3$): δ (ppm) 7.31 (t, J=7.9 Hz, 2H), 7.25-7.19 (m, 3H), 4.22-4.09 (m, 2H), 3.19-3.11 (m, 2H), 3.11-3.03 (m, 2H), 2.42 (s, 1H), 1.25 (t, J=7.1 Hz, 3H); $^{13}$C NMR (125 MHz, $CDCl_3$): δ (ppm) 171.9, 161.7, 139.1, 128.6, 128.1, 126.6, 61.0, 30.2, 29.0, 28.4, 14.1; IR (Neat): $\nu_{max}$ 3441, 3028, 2982, 2931, 1790, 1726, 1334, 1266, 1196, 1034, 971, 747, 700 $cm^{-1}$; Mass (m/z): 218.00 $(M+H)^+$ (calculated for $C_{13}H_{15}NO_2$: M 217.1102); HPLC: 99% (Purity).

Example 11

Ethyl 3-(4-methylphenethyl)-2H-azirine-2-carboxylate (7)

Yield: 49% as a colorless oil $R_f$=0.4 (20% EtOAc/hexane); $^1$H NMR (400 MHz, $CDCl_3$): δ (ppm) 7.12 (s, 4H), 4.23-4.09 (m, 2H), 3.16-3.08 (m, 2H), 3.08-3.01 (m, 2H), 2.42 (s, 1H), 2.32 (s, 3H), 1.25 (t, J=7.0 Hz, 3H); $^{13}$C NMR (75 MHz, $CDCl_3$): δ (ppm) 171.9, 161.8, 136.2, 136.1, 129.3, 128.0, 61.0, 29.8, 29.0, 28.5, 20.9, 14.1; IR (Neat): $\nu_{max}$ 3447, 2923, 2854, 1791, 1726, 1370, 1333, 1266, 1193, 1035, 808, 761, 668 $cm^{-1}$; Mass (m/z): 232.00 $(M+H)^+$ (calculated for $C_{14}H_{17}NO_2$: M 231.1259); HPLC: 97% (Purity).

Example 12

Ethyl 3-(4-chlorophenethyl)-2H-azirine-2-carboxylate (8)

Yield: 45% as colorless oil $R_f$=0.4 (10% EtOAc/hexane); $^1$H NMR (400 MHz, $CDCl_3$): δ (ppm) 7.29 (d, J=8.4 Hz, 2H), 7.18 (d, J=8.4 Hz, 2H), 4.25-4.08 (m, 2H), 3.20-3.01 (m, 4H), 2.43 (s, 1H), 1.26 (t, J=7.1 Hz, 3H); $^{13}$C NMR (75 MHz, $CDCl_3$): δ (ppm) 171.8, 161.6, 137.6, 132.4, 129.6, 128.7, 61.1, 29.6, 29.0, 28.2, 14.1; IR (Neat): $\nu_{max}$ 3440, 2983, 2933, 1790, 1726, 1492, 1370, 1334, 1267, 1197, 1093, 1035, 813, 669 $cm^{-1}$; Mass (m/z): 252.00 $(M+H)^+$ (calculated for $C_{13}H_{14}ClNO_2$: M 251.0713); HPLC: 96% Purity).

Example 13

Ethyl 3-(4-(tert-butyl)phenethyl)-2H-azirine-2-carboxylate (9)

Yield: 35% as colorless oil $R_f$=0.6 (20% EtOAc/hexane); $^1$H NMR (400 MHz, $CDCl_3$): δ (ppm) 7.3 (d, J=8.3 Hz, 2H), 7.1 (d, J=8.3 Hz, 2H), 4.2-4.0 (m, 2H), 3.18-3.08 (m, 2H), 3.08-2.97 (m, 2H), 2.42 (s, 1H), 1.30 (s, 9H), 1.23 (t, J=7.1 Hz, 3H); $^{13}$C NMR (75 MHz, $CDCl_3$): δ (ppm) 171.6, 161.5, 149.1, 135.9, 127.6, 125.2, 60.6, 34.0, 31.0, 29.4, 28.7, 28.1, 13.9; IR (Neat): $\nu_{max}$ 3441, 2961, 2869, 1791, 1727, 1367, 1334, 1267, 1193, 1110, 1036, 821, 761, 666 $cm^{-1}$; Mass (m/z): 274.00 $(M+H)^+$ (calculated for $C_{17}H_{23}NO_2$: M 273.1728); HPLC: 95% (Purity).

Example 14

Ethyl 3-(4-fluorophenethyl)-2H-azirine-2-carboxylate (10)

Yield: 48% as colorless oil $R_f$=0.5 (20% EtOAc/hexane); $^1H$ NMR (300 MHz, $CDCl_3$): δ (ppm) 7.21 (td, J=5.2, 1.8, Hz, 2H), 7.0 (t, J=8.6 Hz, 2H), 4.2-4.0 (m, 2H), 3.19-3.08 (m, 4H), 2.43 (s, 1H), 1.26 (t, J=6.9 Hz, 3H); $^{13}C$ NMR (100 MHz, $CDCl_3$): δ (ppm) 171.9, 161.6, 129.7, 129.6, 115.5, 115.3, 61.1, 29.5, 29.0, 28.5, 14.1; IR (Neat): $v_{max}$ 3440, 2984, 2932, 1790, 1726, 1511, 1370, 1334, 1222, 1196, 1035, 829, 786, 705 $cm^{-1}$; Mass (m/z): 236.00 $(M+H)^+$ (calculated for $C_{13}H_{14}FNO_2$: M 235.1008); HPLC: 91% (Purity).

Example 15

Ethyl (E)-3-(4-phenylbut-3-en-1-yl)-2H-azirine-2-carboxylate (11)

Yield: 35% as colorless oil $R_f$=0.4 (20% EtOAc/hexane); $^1H$ NMR (400 MHz, $CDCl_3$): δ (ppm) 7.38-7.18 (m, 5H), 6.48 (d, J=15.8 Hz, 1H), 6.23 (m, 1H), 4.21-4.07 (m, 2H), 3.0 (t, J=7.3 Hz, 2H), 2.68 (qd, 14.7, 7.3 Hz, 2H), 2.46 (s, 1H), 1.23 (t, J=7.09 Hz, 3H); $^{13}C$ NMR (100 MHz, $CDCl_3$): δ (ppm) 171.9, 161.7, 136.8, 131.9, 128.4, 127.3, 126.8, 126.0, 61.0, 28.8, 27.6, 26.6, 14.1; IR (Neat): $v_{max}$ 3441, 3026, 2982, 2929, 1791, 1726, 1369, 1333, 1266, 1196, 1033, 966, 771, 745, 694 $cm^{-1}$; Mass (m/z): 266.00 $(M+Na)^+$244.00 (M+H)+(calculated for $C_{15}H_{17}NO_2$: M 243.1259); HPLC: 90% (Purity).

Example 16

Ethyl 3-(3,4,5-trimethoxyphenethyl)-2H-azirine-2-carboxylate (12)

Yield: 40% as a colorless oil $R_f$=0.5 (20% EtOAc/hexane); $^1H$ NMR (400 MHz, $CDCl_3$): δ (ppm), 6.45 (s, 2H), 4.23-4.07 (m, 2H), 3.84 (s, 6H), 3.81 (s, 3H), 3.12 (t, J=7.2 Hz, 2H), 3.02 (t, J=7.2 Hz, 2H), 2.4 (s, 1H), 1.24 (t, J=7.0 Hz, 3H); $^{13}C$ NMR (75 MHz, $CDCl_3$): δ (ppm) 171.9, 161.7, 153.2, 136.6, 134.9, 105.1, 61.1, 60.7, 56.0, 30.6, 29.0, 28.6, 14.1; IR (Neat): $v_{max}$ 3444, 2937, 2837, 1724, 1590, 1507, 1459, 1240, 1193, 1125, 1009, 824, 774 $cm^{-1}$; Mass (m/z): 308.15 $(M+H)^+$ (calculated for $C_{16}H_{21}NO_5$: M 307.1419); HPLC: 88% (Purity).

Example 17

Ethyl (E)-3-(4-methoxystyryl)-2H-azirine-2-carboxylate (13)

Yield: 30% as a colorless oil $R_f$=0.5 (20% EtOAc/hexane); $^1H$ NMR (400 MHz, $CDCl_3$): δ (ppm) 7.53 (d, J=8.8 Hz, 2H), 7.29 (d, J=15.7 Hz, 1H), 7.0 (d, J=15.7 Hz, 1H), 6.9 (d, J=8.8 Hz, 2H), 4.28-4.16 (m, 2H), 3.86 (s, 3H), 2.67 (s, 1H), 1.28 (t, J=7.2 Hz, 3H); $^{13}C$ NMR (75 MHz, $CDCl_3$): δ (ppm) 171.9, 162.0, 156.7, 149.0, 130.2, 126.7, 114.5, 106.7, 61.1, 55.4, 28.7, 14.2; IR (Neat): $v_{max}$ 2979, 2842, 1757, 1724, 1601, 1511, 1257, 1176, 1033, 971, 822, 770, 565 $cm^{-1}$; Mass (m/z): 268.10 $(M+Na)^+$ (calculated for $C_{14}H_{15}NO_3$: M 245.1051); HPLC: 96% (Purity).

Example 18

Methyl 3-(4-methoxyphenethyl)-2H-azirine-2-carboxylate (14)

Yield: 48% as a colorless oil $R_f$=0.6 (20% EtOAc/hexane); $^1H$ NMR (500 MHz, $CDCl_3$): δ (ppm) 7.15 (d, J=8.6 Hz, 2H), 6.85 (d, J=8.6 Hz, 2H), 3.79 (s, 3H), 3.70 (s, 3H), 3.14-3.07 (m, 2H), 3.06-2.98 (m, 2H), 2.43 (s, 1H); $^{13}C$ NMR (100 MHz, $CDCl_3$): δ (ppm) 172.3, 161.7, 158.2, 131.1, 129.1, 113.9, 55.1, 52.0, 29.3, 28.7, 28.6; IR (Neat): $v_{max}$ 3446, 3001, 2952, 2839, 1790, 1729, 1611, 1513, 1439, 1341, 1248, 1203, 1182, 1032, 823, 770, 709 $cm^{-1}$; Mass (m/z): 256.10 $(M+Na)^+$ (calculated for $C_{13}H_{15}NO_3$: M 233.1051); HPLC: 90% (Purity).

Example 19

Ethyl 3-(4-bromophenethyl)-2H-azirine-2-carboxylate (15)

Yield: 35% as a colorless oil; $R_f$=0.6 (20% EtOAc/hexane); $^1H$ NMR (500 MHz, $CDCl_3$): δ (ppm) 7.47-7.37 (m, 2H), 7.11 (d, J=6.8 Hz, 2H), 4.21-4.07 (m, 2H), 3.17-3.08 (m, 2H), 3.08-2.99 (m, 2H), 2.43 (d, J=2.2 Hz, 1H), 1.23 (td, J=7.0, 2.2 Hz, 3H); $^{13}C$ NMR (75 MHz, $CDCl_3$): δ (ppm) 171.8, 161.5, 138.1, 131.6, 129.9, 120.5, 61.1, 29.6, 29.0, 28.2, 14.1; IR (Neat): $v_{max}$ 3445, 2930, 1792, 1724, 1629, 1486, 1265, 1195, 1034, 810, 766 $cm^{-1}$; Mass (m/z): 318.00 $(M+Na)^+$ (calculated for $C_{13}H_{14}BrNO_2$: M 295.0207); HPLC: 98% (Purity).

Example 20

Ethyl 3-(4-iodophenethyl)-2H-azirine-2-carboxylate (16)

Yield: 39% as a colorless oil; $R_f$=0.6 (20% EtOAc/hexane); $^1H$ NMR (400 MHz, $CDCl_3$): δ (ppm) 7.63 (d, J=8.3 Hz, 2H), 7.0 (d, J=8.3 Hz, 2H), 4.2-4.0 (m, 2H), 3.2-3.0 (m, 2H), 3.0-3.0 (m, 2H), 2.43 (s, 1H), 1.26 (t, J=7.0 Hz, 3H); $^{13}C$ NMR (100 MHz, $CDCl_3$): δ (ppm) 171.8, 161.6, 138.8, 137.7, 130.3, 91.9, 61.1, 29.8, 29.1, 28.1, 14.1; IR (Neat): $v_{max}$ 3447, 2925, 2854, 1791, 1724, 1266, 1195, 1034, 1008, 807, 765, 669 $cm^{-1}$; Mass (m/z): 366.00 $(M+Na)^+$ (calculated for $C_{13}H_{14}NO_2$: M 343.0069); HPLC: 97% (Purity).

Example 21 tert-butyl 3-(4-methoxyphenethyl)-2H-azirine-2-carboxylate (17)

Yield: 49% as a colorless oil $R_f$=0.6 (20% EtOAc/hexane); $^1H$ NMR (400 MHz, $CDCl_3$): δ (ppm) 7.15 (d, J=8.6 Hz, 2H), 6.84 (d, J=8.6 Hz, 2H), 3.78 (s, 3H), 3.13-3.04 (m, 2H), 3.04-2.96 (m, 2H), 2.43 (s, 1H), 1.44 (s, 9H); $^{13}C$ NMR (100 MHz, $CDCl_3$): δ (ppm) 171.1, 162.0, 158.2, 131.3, 129.1, 114.0, 81.3, 55.1, 29.8, 29.4, 28.7, 27.9; IR (Neat): $v_{max}$ 3443, 2929, 1720, 1615, 1513, 1343, 1248, 1156, 1033, 974, 826, 763 $cm^{-1}$; Mass (m/z): 298.00 $(M+Na)^+$ (calculated for $C_{16}H_{21}NO_3$: M 275.1521); HPLC: 95% (Purity).

Example 22

Benzyl 2-(4-methoxybenzyl)-3-methyl-2H-azirine-2-carboxylate (18)

Yield: 35% as a colorless oil $R_f$=0.6 (20% EtOAc/hexane); $^1$H NMR (400 MHz, $CDCl_3$): δ (ppm) 7.37-7.26 (m, 5H), 7.01 (d, J=8.5 Hz, 2H), 6.78 (d, J=8.5 Hz, 2H), 5.12 (q, J=12.3 Hz, 2H), 3.76 (s, 3H), 3.52 (d, J=15.1 Hz, 1H), 2.99 (d, J=15.1 Hz, 1H), 2.19 (s, 3H); $^{13}$C NMR (75 MHz, $CDCl_3$): δ (ppm) 172.6, 162.8, 158.1, 135.6, 130.5, 129.1, 128.4, 128.1, 127.8, 113.7, 66.8, 55.1, 38.9, 35.8, 12.2; IR (Neat): $\nu_{max}$ 3450, 2925, 2855, 1725, 1196, 1100, 1034, 765, 553 $cm^{-1}$; Mass (m/z): 332.00 $(M+Na)^+$, 310.00 $(M+H)^+$ (calculated for $C_{19}H_{19}NO_3$: M 309.364); HPLC: 93% (Purity).

Example 23

Propyl 3-(4-methoxyphenethyl)-2H-azirine-2-carboxylate (19)

Yield: 45% as a colorless oil $R_f$=0.5 (20% EtOAc/hexane); $^1$H NMR (500 MHz, $CDCl_3$): δ (ppm) 7.15 (d, J=8.6 Hz, 2H), 6.85 (d, J=8.6 Hz, 2H), 4.12-4.0 (m, 2H), 3.79 (s, 3H), 3.4-3.06 (m, 2H), 3.06-2.96 (m, 2H), 2.43 (s, 1H), 1.64 (m, 2H), 0.93 (t, J=7.4 Hz, 3H); $^{13}$C NMR (75 MHz, $CDCl_3$): δ (ppm) 172.0, 161.7, 158.2, 131.2, 129.1, 114.0, 66.4, 55.1, 29.4, 28.9, 28.7, 21.8, 10.2; IR (Neat): $\nu_{max}$ 3447, 2923, 1798, 1651, 1514, 1342, 1247, 1156, 1032, 973, 827, 763 $cm^{-1}$; Mass (m/z): 294.25 $(M-OMe)^+$, 262.20 $(M+H)^+$ (calculated for $C_{15}H_{19}NO_3$: M 261.1364); HPLC: 97% (Purity).

Example 24

Isopropyl 3-(4-methoxyphenethyl)-2H-azirine-2-carboxylate (20)

Yield: 39% as a colorless oil $R_f$=0.6 (20% EtOAc/hexane); $^1$H NMR (400 MHz, $CDCl_3$): δ (ppm) 7.16 (d, J=8.6 Hz, 2H), 6.85 (d, J=8.6 Hz, 2H), 5.03 (m, 1H), 3.79 (s, 3H), 3.14-3.06 (m, 2H), 3.05-2.98 (m, 2H), 2.40 (s, 1H), 1.24 (d, J=6.2 Hz, 6H); $^{13}$C NMR (75 MHz, $CDCl_3$): δ (ppm) 171.5, 161.8, 158.3, 131.3, 129.1, 114.0, 68.6, 55.1, 29.4, 29.2, 28.7, 21.7, 21.7; IR (Neat): $\nu_{max}$ 2981, 2932, 1788, 1721, 1612, 1513, 1248, 1202, 1107, 1033, 981, 822, 768 $cm^{-1}$; Mass (m/z): 262.20 $(M+H)^+$ (calculated for $C_{15}H_{19}NO_3$: M 261.1364); HPLC: 93% (Purity).

Example 25

Isobutyl 3-(4-methoxyphenethyl)-2H-azirine-2-carboxylate (21)

Yield: 45% as a colorless oil $R_f$=0.6 (20% EtOAc/hexane); $^1$H NMR (400 MHz, $CDCl_3$): δ (ppm) 7.15 (d, J=8.6 Hz, 2H), 6.85 (d, J=8.6 Hz, 2H), 3.94-3.84 (m, 2H), 3.79 (s, 3H), 3.14-3.09 (m, 2H), 3.06-2.99 (m, 2H), 2.4 (s, 1H), 1.92 (m, 1H), 0.92 (d, J=6.7 Hz, 6H); $^{13}$C NMR (100 MHz, $CDCl_3$): δ (ppm) 172.0, 161.7, 158.3, 131.2, 129.2, 114.0, 71.1, 55.1, 29.4, 28.9, 28.7, 27.6, 18.9; IR (Neat): $\nu_{max}$ 3418, 2961, 1788, 1725, 1613, 1513, 1463, 1249, 1188, 1028, 821, 698 $cm^{-1}$; Mass (m/z): 308.25 $(M-OMe)^+$, 276.20 $(M+H)^+$ (calculated for $C_{16}H_{21}NO_3$: M 275.1521); HPLC: 97% (Purity).

Example 26 sec-Butyl 3-(4-methoxyphenethyl)-2H-azirine-2-carboxylate (22)

Yield: 50% as a colorless oil; $R_f$=0.6 (20% EtOAc/hexane); $^1$H NMR (400 MHz, $CDCl_3$): δ (ppm) 7.15 (d, J=8.6 Hz, 2H), 6.85 (d, J=8.6 Hz, 2H), 4.87 (m, 1H), 3.79 (s, 3H), 3.14-3.06 (m, 2H), 3.06-2.99 (m, 2H), 2.4 (s, 1H), 1.65-1.48 (m, 2H), 1.20 (dd, J=6.2, 0.9 Hz, 3H), 0.89 (t, J=7.4 Hz, 3H); $^{13}$C NMR (75 MHz, $CDCl_3$): δ (ppm) 171.6, 161.8, 158.3, 131.3, 129.1, 114.0, 73.1, 55.1, 29.4, 29.1, 28.7, 28.6, 19.3, 9.5; IR (Neat): $\nu_{max}$ 2928, 1788, 1721, 1614, 1513, 1249, 1199, 1116, 1030, 824, 764 $cm^{-1}$; Mass (m/z): 276.20 $(M+H)^+$ (calculated for $C_{16}H_{21}NO_3$: M 275.1521); HPLC: 97% (Purity).

Example 27

Pentyl 3-(4-methoxyphenethyl)-2H-azirine-2-carboxylate (23)

Yield: 33% as a colorless oil $R_f$=0.6 (20% EtOAc/hexane); $^1$H NMR (400 MHz, $CDCl_3$): δ (ppm) 7.15 (d, J=8.5 Hz, 2H), 6.84 (d, J=8.5 Hz, 2H), 4.12-4.0 (m, 2H), 3.78 (s, 3H), 3.15-3.06 (m, 2H), 3.06-2.96 (m, 2H), 2.43 (s, 1H), 1.71-1.56 (m, 2H), 1.39-1.24 (m, 4H), 0.93 (t, J=6.9 Hz, 3H); $^{13}$C NMR (75 MHz, $CDCl_3$): δ (ppm) 172.0, 161.7, 158.3, 131.2, 129.1, 114.0, 65.2, 55.1, 29.4, 28.9, 28.7, 28.2, 27.9, 22.2, 13.8; IR (Neat): $\nu_{max}$ 2956, 2864, 1790, 1725, 1612, 1512, 1461, 1336, 1248, 1187, 1035, 822, 549 $cm^{-1}$; Mass (m/z): 322.25 $(M-OMe)^+$, 290.30 $(M+H)^+$ (calculated for $C_{17}H_{23}NO_3$: M 289.1677); HPLC: 95% (Purity).

Example 28

Isopentyl 3-(4-methoxyphenethyl)-2H-azirine-2-carboxylate (24): Yield: 45% as colorless oil $R_f$=0.6 (20% EtOAc/hexane); $^1$H NMR (500 MHz, $CDCl_3$): δ (ppm) 7.15 (d, J=8.6 Hz, 2H), 6.84 (d, J=8.6 Hz, 2H), 4.19-4.06 (m, 2H), 3.78 (s, 3H), 3.14-3.06 (m, 2H), 3.06-2.98 (m, 2H), 2.4 (s, 1H), 1.71-1.60 (m, 1H), 1.51 (q, J=6.8 Hz, 2H), 0.91 (d, J=6.6 Hz, 6H); $^{13}$C NMR (100 MHz, $CDCl_3$): δ (ppm) 172.0, 161.7, 158.3, 131.2, 129.2, 114.0, 63.8, 55.1, 37.2, 29.4, 29.0, 28.7, 24.9, 22.4, 22.3; IR (Neat): $\nu_{max}$ 3782, 3446, 2957, 2926, 1791, 1726, 1613, 1512, 1248, 1188, 1035, 823, 770, 671, 535 $cm^{-1}$; Mass (m/z): 290.20 (M+H)+ (calculated for $C_{17}H_{23}NO_3$: M 289.1677); HPLC: 96% (Purity).

Example 29

2-Methoxyethyl 3-(4-methoxyphenethyl)-2H-azirine-2-carboxylate (25): Yield: 31% as a colorless oil $R_f$=0.5 (30% EtOAc/hexane); $^1$H NMR (400 MHz, $CDCl_3$): δ (ppm) 7.14 (d, J=8.6 Hz, 2H), 6.84 (d, J=8.6 Hz, 2H), 4.32-4.19 (m, 2H), 3.78 (s, 3H), 3.63-3.54 (m, 2H), 3.38 (m, 3H), 3.14-3.06 (m, 2H), 3.05-2.95 (m, 2H), 2.4 (s, 1H); $^{13}$C NMR (100 MHz, $CDCl_3$): δ (ppm) 171.9, 161.5, 158.2, 131.2, 129.1, 113.9, 70.1, 64.0, 58.8, 55.1, 29.3, 28.7, 28.6; IR (Neat): $\nu_{max}$ 2930, 1791, 1725, 1610, 1511, 1246, 1184, 1128, 1034, 824, 533

$cm^{-1}$; Mass (m/z): 278.20 $(M+H)^+$ (calculated for $C_{15}H_{19}NO_4$: M 277.1314); HPLC: 91% (Purity).

Example 30

Allyl 3-(4-methoxyphenethyl)-2H-azirine-2-carboxylate (26): Yield: 21% as a colorless oil $R_f$=0.6 (20% EtOAc/hexane); $^1$H NMR (400 MHz, $CDCl_3$): δ (ppm) 7.15 (d, J=8.5 Hz, 2H), 6.85 (d, J=8.5 Hz, 2H), 5.95-5.85 (m, 1H), 5.31 (dd, J=17.2, 1.3 Hz, 1H), 5.24 (dd, J=10.3, 0.9 Hz, 1H), 4.60 (m, 2H), 3.79 (s, 3H), 3.17-3.07 (m, 2H), 3.07-2.98 (m, 2H), 2.4 (s, 1H); $^{13}$C NMR (75 MHz, $CDCl_3$): δ (ppm) 171.6, 161.6, 158.3, 131.7, 131.2, 129.2, 118.5, 114.0, 65.7, 55.2, 29.4, 28.9, 28.7; IR (Neat): $\nu_{max}$ 2979, 2842, 1757, 1724, 1601, 1511, 1257, 1176, 1033, 972, 823, 771, 566 $cm^{-1}$; Mass (m/z): 260.20 $(M+H)^+$ (calculated for $C_{15}H_{17}NO_3$: M 259.1208); HPLC: 97% (Purity).

Example 31

Ethyl 3-(2-(naphthalen-2-yl) ethyl)-2H-azirine-2-carboxylate (27): Yield: 45% as a colorless oil $R_f$=0.5 (20% EtOAc/hexane); $^1$H NMR (400 MHz, $CDCl_3$): δ (ppm) 7.84-7.73 (m, 3H), 7.67 (s, 1H), 7.49-7.41 (m, 2H), 7.35 (dd, J=8.3, 1.7 Hz, 1H), 4.18-4.04 (m, 2H), 3.29-3.16 (m, 4H), 2.4 (s, 1H), 1.20 (t, J=7.0 Hz, 3H); $^{13}$C NMR (100 MHz, $CDCl_3$): δ (ppm) 171.8, 161.7, 136.6, 133.4, 132.2, 128.3, 127.5, 127.4, 126.6, 126.5, 126.1, 125.5, 61.0, 30.3, 29.0, 28.2, 14.0; IR (Neat): $\nu_{max}$ 3019, 2981, 1721, 1369, 1332, 1266, 1191, 1033, 971, 855, 816, 746, 667 $cm^{-1}$; Mass (m/z): 268.00 $(M+H)^+$ (calculated for $C_{17}H_{17}NO_2$: M 267.1259); HPLC: 95% (Purity).

Example 32

Ethyl 3-(4-(trifluoromethoxy) phenethyl)-2H-azirine-2-carboxylate (28): Yield: 21% as a colorless oil $R_f$=0.5 (20% EtOAc/hexane); $^1$H NMR (400 MHz, $CDCl_3$): δ (ppm) 7.28 (d, J=8.6 Hz, 2H), 7.17 (d, J=8.6 Hz, 2H), 4.22-4.09 (m, 2H), 3.19-3.06 (m, 4H), 2.4 (s, 1H), 1.25 (t, J=7.0 Hz, 3H); $^{13}$C NMR (100 MHz, $CDCl_3$): δ (ppm) 171.8, 161.6, 147.9, 137.9, 129.6, 121.2, 61.1, 29.6, 29.1, 28.3, 14.1; IR (Neat): $\nu_{max}$ 2925, 2853, 1725, 1509, 1254, 1192, 1154, 1020, 973, 920, 846, 809, 788, 672 $cm^{-1}$; Mass (m/z): 302.00 (M+H)+ (calculated for $C_{14}H_{14}F_3NO_3$: M 301.0925); HPLC: 97% (Purity).

Example 33

Octyl 3-(4-methoxyphenethyl)-2H-azirine-2-carboxylate (29): Yield: 50% as a colorless oil $R_f$=0.5 (20% EtOAc/hexane); $^1$H NMR (400 MHz, $CDCl_3$): δ (ppm) 7.15 (d, J=8.6 Hz, 2H), 6.84 (d, J=8.6 Hz, 2H), 4.15-4.0 (m, 2H), 3.78 (s, 3H), 3.13-3.06 (m, 2H), 3.05-2.97 (m, 2H), 2.42 (s, 1H), 1.69-1.52 (m, 2H), 1.38-1.19 (m, 10H), 0.88 (t, J=7.0 Hz, 3H); $^{13}$C NMR (100 MHz, $CDCl_3$): δ (ppm) 172.0, 161.7, 158.3, 131.2, 129.2, 114.0, 65.2, 55.1, 31.7, 29.4, 29.1, 29.0, 28.7, 28.5, 25.7, 22.5, 14.0; IR (Neat): $\nu_{max}$ 2926, 2855, 1790, 1724, 1612, 1512, 1464, 1246, 1177, 1107, 1034, 976, 810, 723 $cm^{-1}$; Mass (m/z): 332.00 (M+H)+ (calculated for $C_{20}H_{29}NO_3$: M 331.2147); HPLC: 98% (Purity).

Example 34

Ethyl 3-(2-(tetrahydrofuran-2-yl) ethyl)-2H-azirine-2-carboxylate (30): Yield: 21% as a colorless oil $R_f$=0.4 (20% EtOAc/hexane); $^1$H NMR (400 MHz, $CDCl_3$): δ (ppm) 4.24-4.09 (m, 2H), 3.99-3.79 (m, 2H), 3.73 (m, 1H), 3.02-2.85 (m, 2H), 2.45 (s, 1H), 2.09-1.82 (m, 4H), 1.57-1.46 (m, 2H), 1.26 (t, J=7.2 Hz, 3H); $^{13}$C NMR (100 MHz, $CDCl_3$): δ (ppm) 172.1, 162.1, 67.7, 61.0, 31.0, 30.0, 29.0, 25.7, 23.8, 23.9, 14.2; IR (Neat): $\nu_{max}$ 2925, 2855, 1791, 1725, 1445, 1369, 1332, 1263, 1186, 1068, 1032, 972, 790 $cm^{-1}$; Mass (m/z): 212.00 $(M+H)^+$ (calculated for $C_{11}H_{17}NO_3$: M 211.1208); HPLC: 93% (Purity).

Example 35

Ethyl 3-(4-cyanophenethyl)-2H-azirine-2-carboxylate (31): Yield: 39% as a colorless oil $R_f$=0.5 (20% EtOAc/hexane); $^1$H NMR (500 MHz, $CDCl_3$): δ (ppm) 7.61 (d, J=8.4 Hz, 2H), 7.37 (d, J=8.4 Hz, 2H), 4.21-4.07 (m, 2H), 3.16 (m, 4H), 2.4 (s, 1H), 1.24 (t, J=7.2 Hz, 3H); $^{13}$C NMR (75 MHz, $CDCl_3$): δ (ppm) 171.6, 161.4, 144.6, 132.4, 129.1, 118.5, 110.7, 61.1, 30.2, 29.2, 27.8, 14.1; IR (Neat): $\nu_{max}$ 2982, 2934, 2227, 1789, 1721, 1193, 1033, 908, 823, 754, 729, 667 $cm^{-1}$; Mass (m/z): 243.45 $(M+H)^+$ (calculated for $C_{14}H_{14}N_2O_2$: M 242.1055); HPLC: 93% (Purity).

Example 36

Ethyl 3-(4-butoxyphenethyl)-2H-azirine-2-carboxylate (32): Yield: 55% as a colorless oil $R_f$=0.5 (20% EtOAc/hexane); $^1$H NMR (400 MHz, $CDCl_3$): δ (ppm) 7.13 (d, J=8.6 Hz, 2H), 6.83 (d, J=8.6 Hz, 2H), 4.22-4.09 (m, 2H), 3.93 (t, J=6.6 Hz, 2H), 3.17-3.06 (m, 2H), 3.06-2.97 (m, 2H), 2.42 (s, 1H), 1.80-1.70 (m, 2H), 1.54-1.42 (m, 2H), 1.25 (t, J=7.0 Hz, 3H), 0.97 (t, J=7.3 Hz, 3H); $^{13}$C NMR (100 MHz, $CDCl_3$): δ (ppm) 171.9, 161.8, 157.9, 131.0, 129.1, 114.6, 67.6, 61.0, 31.2, 29.4, 28.9, 28.7, 19.2, 14.1, 13.8; IR (Neat): $\nu_{max}$ 2958, 2933, 1726, 1612, 1511, 1244, 1193, 1034, 906, 752, 730, 668 $cm^{-1}$; Mass (m/z): 290.25 $(M+H)^+$ (calculated for $C_{17}H_{23}NO_3$: M 289.1677); HPLC: 99% (Purity).

Example 37

Ethyl 3-(2-(anthracen-9-yl)ethyl)-2H-azirine-2-carboxylate (33): Yield: 32% as a colorless oil $R_f$=0.4 (20% EtOAc/hexane); $^1$H NMR (500 MHz, $CDCl_3$): δ (ppm) 8.4 (s, 1H), 8.23 (d, J=8.8 Hz, 2H), 8.04 (d, J=8.3 Hz, 2H), 7.56 (t, J=8.8 Hz, 2H), 7.49 (t, J=8.3 Hz, 2H), 4.29-4.15 (m, 2H), 4.1 (t, J=8.0 Hz, 2H), 3.35-3.23 (td, J=7.6, 3.0 Hz, 2H), 2.5 (s, 1H), 1.30 (t, J=7.1 Hz, 3H); $^{13}$C NMR (100 MHz, $CDCl_3$): δ (ppm) 171.9, 161.9, 131.5, 130.9, 129.4, 129.4, 126.9, 126.2, 125.0, 123.4, 61.2, 29.5, 27.8, 22.4, 14.2; IR (Neat): $\nu_{max}$ 2980, 1789, 1722, 1332, 1262, 1194, 1095, 1031, 884, 839, 787, 731, 665 $cm^{-1}$; Mass (m/z): 318.20 $(M+H)^+$ (calculated for $C_{21}H_{19}NO_2$: M 317.1415); HPLC: 98% (Purity).

Example 38

Ethyl 3-(3,4-dimethoxyphenethyl)-2H-azirine-2-carboxylate (34): Yield: 46% solid, M.P=55-57° C. $R_f$=0.5 (20% EtOAc/hexane); $^1$H NMR (400 MHz, $CDCl_3$): δ (ppm) 6.82-6.73 (m, 3H), 4.21-4.08 (m, 2H), 3.86 (s, 3H), 3.84 (s, 3H), 3.14-3.07 (m, 2H), 3.06-2.98 (m, 2H), 2.43 (s, 1H), 1.24 (t, J=7.0 Hz, 3H); $^{13}$C NMR (100 MHz, $CDCl_3$): δ (ppm) 171.8, 161.6, 148.8, 147.6, 131.7, 120.0, 111.5, 111.2, 61.0, 55.7, 55.7, 29.8, 28.9, 28.6, 14.0; IR (Neat): $\nu_{max}$ 2936, 2835, 1721, 1514, 1418, 1259, 1236, 1188, 1025, 850, 806, 763 $cm^{-1}$; Mass (m/z): 278.20 $(M+H)^+$ (calculated for $C_{15}H_{19}NO_4$: M 277.1314); HPLC: 96% (Purity).

Example 39

Diethyl 3-(4-methoxyphenethyl)-2H-azirine-2,2-dicarboxylate (35): Yield: 11% as a colorless oil $R_f$=0.5 (20% EtOAc/hexane); $^1H$ NMR (400 MHz, $CDCl_3$): δ (ppm) 7.17 (d, J=8.6 Hz, 2H), 6.84 (d, J=8.6 Hz, 2H), 4.27 (q, J=7.0 Hz, 2H), 3.7 (s, 3H), 3.6 (q, J=7.0 Hz, 2H), 3.05-2.98 (m, 2H), 2.96-2.87 (m, 2H), 1.33 (t, J=7.0 Hz, 3H), 1.24 (t, J=7.0 Hz, 3H); $^{13}C$ NMR (100 MHz, $CDCl_3$): δ (ppm) 170.0, 164.6, 162.7, 157.8, 133.6, 129.2, 113.8, 86.7, 59.9, 55.2, 44.8, 33.1, 29.6, 14.4, 13.4; IR (Neat): $\nu_{max}$ 2975, 2932, 1696, 1582, 1511, 1443, 1363, 1301, 1244, 1190, 1165, 1081, 1035, 822, 785; Mass (m/z): 274.00 $(M-OEt)^+$ (calculated for $C_{17}H_{21}NO_5$: M 319.1419); HPLC: 90% (Purity).

Example 40

Ethyl 3-(4-vinylphenethyl)-2H-azirine-2-carboxylate (36): Yield: 29% as a colorless oil $R_f$=

0.5 (20% EtOAc/hexane); $^1H$ NMR (400 MHz, $CDCl_3$): δ (ppm) 7.36 (d, J=8.1 Hz, 2H), 7.20 (d, J=8.1 Hz, 2H), 6.69 (m, 1H), 5.72 (dd, J=17.6, 0.8 Hz, 1H), 5.23 (dd, J=10.8, 0.8 Hz, 1H), 4.22-4.09 (m, 2H), 3.17-3.11 (m, 2H), 3.11-3.03 (m, 2H), 2.43 (s, 1H), 1.25 (t, J=7.0 Hz, 3H); $^{13}C$ NMR (75 MHz, $CDCl_3$): δ (ppm) 171.9, 161.7, 138.8, 136.3, 136.1, 128.4, 126.4, 113.6, 61.1, 30.0, 29.0, 28.3, 14.1; IR (Neat): $\nu_{max}$ 2980, 2925, 2853, 1722, 1512, 1369, 1333, 1264, 1189, 1032, 990, 908, 839, 828, 708 $cm^{-1}$; Mass (m/z): 244.00 $(M+H)^+$ (calculated for $C_{15}H_{17}NO_2$: M 243.1259); HPLC: 90% (Purity).

Example 41

Ethyl 3-(3-(2, 3-dihydrobenzofuran-5-yl)propyl)-2H-azirine-2-carboxylate (37): Yield: 24% as a colorless oil $R_f$=0.4 (20% EtOAc/hexane); $^1H$ NMR (400 MHz, $CDCl_3$): δ (ppm) 7.01 (s, 1H), 6.90 (d, J=8.0 Hz, 1H), 6.70 (d, J=8.0 Hz, 1H), 4.54 (t, J=8.6 Hz, 2H), 4.24-4.10 (m, 2H), 3.17 (t, J=8.6 Hz, 2H), 2.80 (t, J=7.2 Hz, 2H), 2.68 (t, J=7.3 Hz, 2H), 2.41 (s, 1H), 2.09-1.98 (m, 2H), 1.26 (t, J=7.2 Hz, 3H); $^{13}C$ NMR (75 MHz, $CDCl_3$): δ (ppm) 172.0, 161.9, 158.5, 132.4, 127.8, 127.1, 124.9, 109.0, 71.1, 61.0, 34.2, 29.7, 28.6, 26.2, 25.8, 14.1; IR (Neat): $\nu_{max}$ 2935, 1791, 1723, 1615, 1491, 1369, 1191, 1102, 982, 944, 818, 750 $cm^{-1}$; Mass (m/z): 274.20 $(M+H)^+$ (calculated for $C_{16}H_{19}NO_3$: M 273.1364); HPLC: 96% (Purity).

Example 42 tert-Butyl 3-(2-(2-(ethoxycarbonyl)-2H-azirin-3-yl)ethyl)-1H-indole-1-carboxylate (38): Yield: 38% as colorless oil $R_f$=0.4 (30% EtOAc/hexane); $^1H$ NMR (400 MHz, $CDCl_3$): δ (ppm) 8.3 (s, 1H), 7.52 (d, J=7.8 Hz, 1H), 7.45 (s, 1H), 7.37-7.31 (td, J=7.2, 1.2 Hz, 1H), 7.28-7.23 (dt, J=7.4, 0.8 Hz, 1H), 4.23-4.09 (m, 2H), 3.27-3.21 (m, 2H), 3.21-3.15 (m, 2H), 2.48 (s, 1H), 1.67 (s, 6H), 1.56 (s, 3H), 1.25 (t, J=7.2 Hz, 3H); $^{13}C$ NMR (75 MHz, $CDCl_3$): δ (ppm) 171.9, 161.9, 125.0, 124.6, 124.1, 122.9, 122.5, 118.5, 118.2, 115.4, 83.7, 81.6, 61.1, 29.1, 28.1, 26.7, 19.9, 14.1; IR (Neat); $\nu_{max}$ 2980, 2932, 1724, 1608, 1453, 1370, 1308, 1192, 1084, 1034, 856, 747, 667 $cm^{-1}$; Mass (m/z): 257.15 $(M-Boc)^+$ (calculated for $C_{20}H_{24}N_2O_4$: M 356.1736); HPLC: 94% (Purity).

Example 43

Ethyl 3-(2-(2, 3-dihydrobenzofuran-5-yl)ethyl)-2H-azirine-2-carboxylate (39): Yield: 48% as colorless oil $R_f$=0.5 (20% EtOAc/hexane); $^1H$ NMR (500 MHz, $CDCl_3$): δ (ppm) 7.06 (s, 1H), 6.95 (d, J=8.0 Hz, 1H), 6.71 (d, J=8.0 Hz, 1H), 4.55 (t, J=8.6 Hz, 2H), 4.24-4.10 (m, 2H), 3.18 (t, J=8.6 Hz, 2H), 3.13-3.05 (m, 2H), 3.04-2.95 (m, 2H), 2.42 (s, 1H), 1.26 (t, J=7.1 Hz, 3H); $^{13}C$ NMR (125 MHz, $CDCl_3$): δ (ppm) 171.9, 161.8, 158.8, 131.2, 127.7, 127.4, 124.8, 109.2, 71.1, 61.0, 29.7, 29.6, 29.0, 14.1; IR (Neat): $\nu_{max}$ 2980, 2930, 1790, 1721, 1492, 1187, 1102, 1033, 981, 942, 814, 789, 773, 711 $cm^{-1}$; Mass (m/z): 260.15 $(M+H)^+$ (calculated for $C_{15}H_{17}NO_3$: M 259.1208); HPLC: 98% (Purity).

Example 44

Ethyl 3-(3-(benzofuran-5-yl)propyl)-2H-azirine-2-carboxylate (40): Yield: 49% as colorless oil $R_f$=0.5 (20% EtOAc/hexane); $^1H$ NMR (400 MHz, $CDCl_3$): δ (ppm) 7.61 (d, J=2.0 Hz, 1H), 7.43 (d, J=8.4 Hz, 1H), 7.40 (s, 1H), 7.11 (dd, J=8.4, 1.3 Hz, 1H), 6.72 (d, J=2.0 Hz, 1H), 4.26-4.11 (m, 2H), 2.92-2.76 (m, 4H), 2.43 (s, 1H), 2.20-2.04 (m, 2H), 1.27 (t, J=7.0 Hz, 3H); $^{13}C$ NMR (100 MHz, $CDCl_3$): δ (ppm) 172.1, 161.9, 153.7, 145.2, 134.9, 127.6, 124.8, 120.6, 111.2, 106.3, 61.1, 34.6, 28.7, 26.3, 25.9, 14.2; IR (Neat): $\nu_{max}$ 2981, 2934, 2865, 1791, 1721, 1537, 1261, 1189, 1028, 973, 883, 814, 770, 736, 640 $cm^{-1}$; Mass (m/z): 271.25 $(M+H)^+$ (calculated for $C_{16}H_{17}NO_3$: M 271.1208); HPLC: 100% (Purity).

Example 45

Ethyl 3-(2-(benzo[d][1,3]dioxol-5-yl)ethyl)-2H-azirine-2-carboxylate (41): Yield: 29% as a colorless oil $R_f$=0.4 (20% EtOAc/hexane); $^1H$ NMR (400 MHz, $CDCl_3$): δ (ppm) 6.75 (d, J=7.8 Hz, 1H), 6.72 (d, J=1.5 Hz, 1H), 6.68 (dd, J=7.8, 1.7 Hz, 1H), 5.94 (s, 2H), 4.24-4.10 (m, 2H), 3.13-3.05 (m, 2H), 3.04-2.94 (m, 2H), 2.43 (s, 1H), 1.27 (t, J=7.2 Hz, 3H); $^{13}C$ NMR (125 MHz, $CDCl_3$): δ (ppm) 171.9, 161.7, 147.7, 146.2, 132.9, 121.1, 108.6, 108.3, 100.9, 61.1, 30.0, 29.0, 28.7, 14.1; IR (Neat): $\nu_{max}$ 2982, 2904, 1790, 1723, 1608, 1503, 1245, 1191, 1037, 975, 931, 858, 810, 772 $cm^{-1}$; Mass (m/z): 262.15 $(M+H)^+$ (calculated for $C_{14}H_{15}NO_4$: M 261.1001); HPLC: 99% (Purity).

Example 46

Ethyl 3-(4-(2, 3-dihydrobenzofuran-5-yl)butyl)-2H-azirine-2-carboxylate (42): Yield: 39% as a colorless oil $R_f$=0.5 (20% EtOAc/hexane); $^1H$ NMR (400 MHz, $CDCl_3$): δ (ppm) 6.99 (s, 1H), 6.88 (d, J=8.0 Hz, 1H), 6.68 (d, J=8.0 Hz, 1H), 4.54 (t, J=8.5 Hz, 2H), 4.24-4.10 (m, 2H), 3.16 (t, J=8.5 Hz, 2H), 2.82 (t, J=6.7 Hz, 2H), 2.58 (t, J=6.7 Hz, 2H), 2.41 (s, 1H), 1.85-1.65 (m, 4H), 1.25 (t, J=7.0 Hz, 3H); $^{13}C$ NMR (100 MHz, $CDCl_3$): δ (ppm) 172.0, 161.8, 158.2, 133.5, 127.6, 126.9, 124.7, 108.8, 71.1, 61.0, 34.6, 31.1, 29.7, 28.7, 26.5, 23.6, 14.1; IR (Neat): $\nu_{max}$ 2978, 2934, 2859, 1791, 1723, 1491, 1188, 1031, 982, 944, 813, 714 $cm^{-1}$; Mass (m/z): 310.00 $(M+Na)^+$ (calculated for $C_{17}H_{21}NO_3$: M 287.1521); HPLC: 97% (Purity).

Example 47

Ethyl 3-(3-(benzo[d][1,3]dioxol-5-yl)propyl)-2H-azirine-2-carboxylate (60): Yield: 48% as colorless oil $R_f$=0.5 (20%

EtOAc/hexane); $^{1}$H NMR (400 MHz, $CDCl_3$): δ (ppm) 6.73 (d, J=7.9 Hz, 1H), 6.67 (d, J=1.5 Hz, 1H), 6.63 (dd, J=7.9, 1.5 Hz, 1H), 5.93 (s, 2H), 4.25-4.07 (m, 2H), 2.81 (t, J=7.2 Hz, 2H) 2.69 (t, J=7.4 Hz, 2H), 2.43 (s, 1H), 2.10-1.93 (m, 2H), 1.27 (t, J=7.0 Hz, 3H); $^{13}$C NMR (100 MHz, $CDCl_3$): δ (ppm) 172.0, 161.8, 147.6, 145.9, 134.2, 121.2, 108.8, 108.2, 100.8, 61.0, 34.4, 28.7, 26.0, 25.8, 14.1; IR (Neat): $\nu_{max}$ 2981, 2926, 2872, 1791, 1722, 1503, 1488, 1369, 1333, 1244, 1188, 1035, 973, 927, 861, 809, 633 $cm^{-1}$; Mass (m/z): 298.00 $(M+Na)^+$, 276.00 $(M+H)^+$ (calculated for $C_{15}H_{17}NO_4$: M 275.1157); HPLC: 97% (Purity).

Example 48

Ethyl 3-(3-(dibenzo[b,d]furan-2-yl)propyl)-2H-azirine-2-carboxylate (44): Yield: 49% as a colorless oil $R_f$=0.5 (20% EtOAc/hexane); $^{1}$H NMR (400 MHz, $CDCl_3$): δ (ppm) 7.94 (d, J=8.3 Hz, 1H), 7.70 (d, J=1.4 Hz, 1H), 7.5 (d, J=8.3 Hz, 1H), 7.49 (d, J=8.3 Hz, 1H), 7.47-7.42 (td, J=7.3, 1.3 Hz, 1H), 7.37-7.30 (td, J=7.3, 0.8 Hz, 1H), 7.27 (dd, J=8.3, 1.7 Hz, 1H), 4.27-4.13 (m, 2H), 2.93 (t, J=7.4 Hz, 2H), 2.85 (t, J=7.2 Hz, 2H), 2.4 (s, 1H), 2.24-2.09 (m, 2H), 1.27 (t, J=7.09 Hz, 3H); $^{13}$C NMR (100 MHz, $CDCl_3$): δ (ppm) 172.0, 161.8, 156.3, 154.7, 134.9, 127.4, 127.0, 124.2, 123.9, 122.5, 120.4, 120.1, 111.5, 111.3, 61.0, 34.5, 28.6, 26.2, 25.8, 14.1; IR (Neat): $\nu_{max}$ 2981, 2934, 2866, 1728, 1479, 1447, 1332, 1187, 1028, 800, 767, 748, 725, 624, 615 $cm^{-1}$; Mass (m/z): 322.00 $(M+H)^+$ (calculated for $C_{20}H_{19}NO_3$: M 321.1364); HPLC: 99% (Purity).

Example 49

Ethyl 3-(3-(chroman-6-yl)propyl)-2H-azirine-2-carboxylate (45): Yield: 49.5% as a colorless oil $R_f$=0.5 (20% EtOAc/hexane); $^{1}$H NMR (400 MHz, $CDCl_3$): δ (ppm) 6.88 (dd, J=8.1, 2.0 Hz, 1H), 6.84 (s, 1H), 6.71 (d, J=8.1 Hz, 1H), 4.24-4.11 (m, 4H), 2.81 (t, J=7.21 Hz, 2H), 2.75 (t, J=6.4 Hz, 2H), 2.65 (t, J=7.4 Hz, 2H), 2.41 (s, 1H), 2.09-1.95 (m, 4H), 1.27 (t, J=7.0 Hz, 3H); $^{13}$C NMR (100 MHz, $CDCl_3$): δ (ppm) 172.1, 161.9, 153.2, 131.9, 129.6, 127.1, 122.0, 116.6, 66.3, 61.0, 33.9, 28.6, 26.0, 25.9, 24.8, 22.3, 14.1; IR (Neat): $\nu_{max}$ 2930, 2857, 1724, 1499, 1369, 1333, 1266, 1188, 1126, 1061, 1033, 1007, 820 $cm^{-1}$; Mass (m/z): 288.10 $(M+H)^+$ (calculated for $C_{17}H_{21}NO_3$: M 287.1521); HPLC: 98% (Purity).

Example 50

Ethyl (E)-3-(4-(dimethylamino)styryl)-2H-azirine-2-carboxylate (46): Yield: 49% yellow color solid, M.P=119-121° C. $R_f$=0.5 (30% EtOAc/hexane); $^{1}$H NMR (400 MHz, $CDCl_3$): δ (ppm) 7.46 (d, J=8.8 Hz, 2H), 7.24 (d, J=15.5 Hz, 1H), 6.86 (d, J=15.5 Hz, 1H), 6.68 (d, J=8.8 Hz, 2H), 4.27-4.14 (m, 2H), 3.05 (s, 6H), 2.63 (s, 1H), 1.28 (t, J=7.0 Hz, 3H); $^{13}$C NMR (125 MHz, $CDCl_3$): δ (ppm) 172.3, 156.4, 152.1, 149.9, 130.2, 121.7, 111.7, 103.2, 61.0, 40.0, 28.6, 14.2; IR (Neat): $\nu_{max}$ 2981, 2905, 1751, 1725, 1590, 1524, 1367, 1330, 1170, 1037, 968, 919, 810, 728, 567 $cm^{-1}$; Mass (m/z): 259.15 $(M+H)^+$ (calculated for $C_{15}H_{18}N_2O_2$: M 258.1368); HPLC: 83% (Purity).

Example 51

Ethyl 3-(4-(dimethylamino)phenethyl)-2H-azirine-2-carboxylate (47): Yield: 47% as a pale color oil $R_f$=0.5 (30% EtOAc/hexane); $^{1}$H NMR (400 MHz, $CDCl_3$): δ (ppm) 7.10 (d, J=8.8 Hz, 2H), 6.70 (d, J=8.8 Hz, 2H), 4.24-4.10 (m, 2H), 3.15-3.06 (m, 2H), 3.03-2.95 (m, 2H), 2.92 (s, 6H), 2.42 (s, 1H), 1.26 (t, J=7.0 Hz, 3H); $^{13}$C NMR (100 MHz, $CDCl_3$): δ (ppm) 172.0, 161.8, 149.4, 128.8, 127.1, 112.8, 61.0, 40.6, 29.3, 28.9, 28.8, 14.1; IR (Neat): $\nu_{max}$ max 2981, 2928, 2801, 1789, 1724, 1614, 1333, 1190, 1164, 1034, 946, 810 $cm^{-1}$; Mass (m/z): 261.15 $(M+H)^+$ (calculated for $C_{15}H_{20}N_2O_2$: M 260.1524); HPLC: 95% (Purity).

Example 52

3-(4-methoxyphenethyl)-2H-azirine-2-carbonitrile (48): Compound 48 was achieved from the 5-(4-methoxyphenyl)-3-oxo-pentanenitrile following the general procedure described for the compound 1. $^{1}$H NMR (400 MHz, $CDCl_3$): δ (ppm) 7.1 (d, 2H), 6.8 (d, 2H), 3.7 (s, 3H), 3.2 (m, 2H), 3.1 (m, 2H), 2.1 (s, 0.9H), 1.9 (d, 0.4H).

Example 53

Diethyl (3-(4-methoxyphenethyl)-2H-azirin-2-yl)phosphonate (49): The synthesis of compound 49 was achieved from the diethyl [4-(4-methoxyphenyl)-2-oxobutyl]phosphonate following the general procedure described for compound 1. $^{1}$H NMR (400 MHz, $CDCl_3$): δ (ppm) 7.1 (d, 2H), 6.8 (d, 2H), 4.1 (m, 4H), 3.7 (s, 3H), 3.1 (m, 2H), 3.0 (m, 2H), 1.7-1.6 (d, 1H), 1.3 (q, 6H); Mass (m/z): 312 $(M+H)^+$ (calculated for: $C_{15}H_{22}NO_4P$: M 311.31).

Example 54

Ethyl 3-(4-((tetrahydrofuran-3-yl)oxy)phenethyl)-2H-azirine-2-carboxylate (50): The synthesis of compound 50 was achieved from p-ketoester following the general procedure described for the compound 1. $^{1}$H NMR (400 MHz, $CDCl_3$): δ (ppm) 7.1 (d, 2H), 6.8 (d, 2H), 4.8 (m, 1H), 4.1 (m, 2H), 3.9 (m, 3H), 3.8 (m, 1H), 3.1 (m, 4H), 2.4 (s, 1H), 2.1 (m, 2H), 1.25 (t, 3H); Mass (m/z): 304.2 $(M+H)^+$ (calculated for $C_{17}H_{21}NO_4$: M 303.3).

Example 55

5-(3-(4-Methoxyphenethyl)-2H-azirin-2-yl)-1H-tetrazole (51): To a stirred mixture of 3-[2-(4-methoxyphenyl)ethyl]-2H-azirene-2-carbonitrile (600 mg, 1 equiv), ammonium chloride (1.1 g, 7 equiv) and sodium azide (390 mg, 2 equiv) was added IPA (2.5 mL) and water (2.5 mL) at room temperature and stirred for 10 min. The reaction mixture was evaporated under reduced pressure to dryness. Crude was taken into diethyl ether (20 mL), stirred for 10 min then ether layer was separated, dried over sodium sulfate and filtered. Dioxane HCl (1 mL) was added to ether layer, compound was precipitated out which was filtered, washed with DCM and dried to obtain 5-{3-[2-(4-methoxyphenyl)ethyl]-2H-aziren-2-yl}-1H-tetrazole.hydrochloride (103 mg, 14.12%) as an off white solid. $^{1}$H NMR (400 MHz, $D_2O$): δ (ppm) 7.2 (d, 2H), 6.9 (d, 2H), 3.8 (s, 3H), 3.3 (s, 1H), 2.9 (m, 2H), 2.6 (m, 2H); $^{1}$H NMR (400 MHz, $CD_3OD$): δ (ppm) 7.1 (d, 2H), 6.8 (d, 2H), 3.7 (s, 3H), 3.3 (s, 1H), 2.8 (m, 2H), 2.6 (m, 2H); $^{1}$H NMR (400 MHz, DMSO): δ (ppm) 9.3 (s, 2H), 7.3 (d, 1H), 7.1 (m, 4H), 6.8 (d, 2H), 3.7 (s, 3H), 2.8 (m, 2H).

Example 56: Biological Activity and Screening

Materials & Methods

Methodologies and Results for Compound 1

Compound 1 possessed a potent anti-angiogenic activity on primary tubulogenesis screening (75 nM) and 3D angiogenesis screening (250 nm) activity. The compound showed its anti-angiogenic activity in different models such as matrigel implantation assay, CAM and ear angiogenesis assay. The compound 1 inhibits the tumor growth in the in vivo xenograft mouse model both in the intramuscular and intra peritoneal injection 25 mg/kg compound. The compound 1 partially inhibits the expression of VEGFR2 and SRC kinase expression. The compound 1 inhibited angiogenesis it through its binding of the ligand endothelin. In total, the compound 1 is a potent inhibitor angiogenesis with a new target.

Compound 1 Reduces the Initial Primary In Vitro Tubulogenesis in HUVECs

Figure 2:
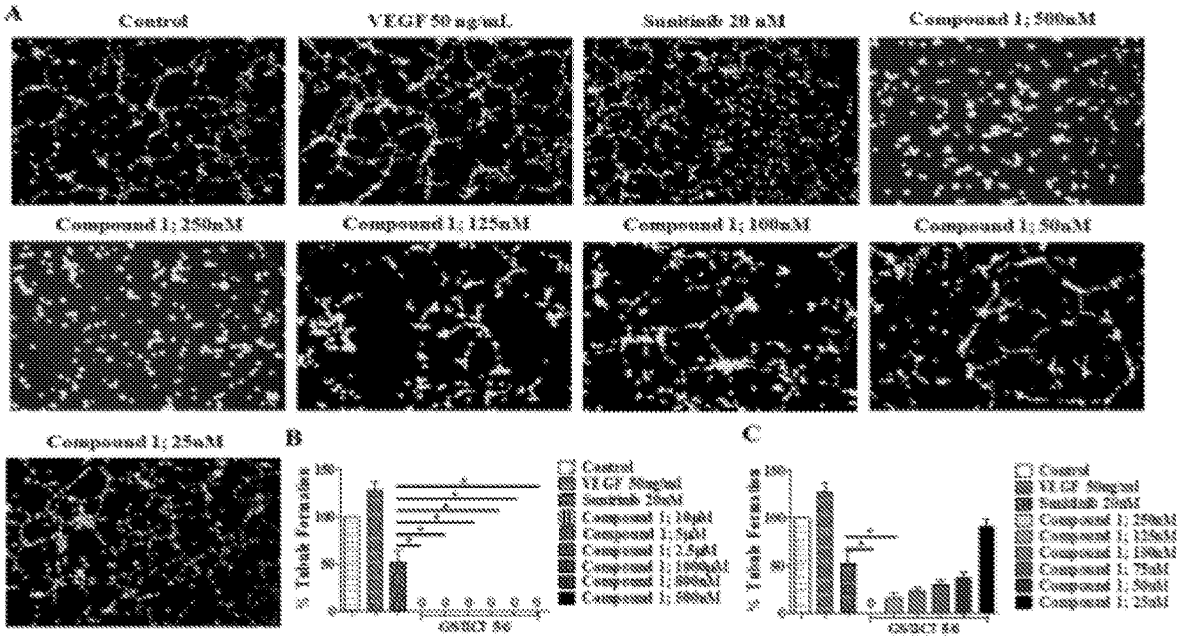
FIG. 2 represents effect of Compound 1 on capillary tube formation of HUVECs. Endothelial cells in Matrigel were incubated with ECM basal medium in the presence of compound 1 at the indicated concentrations for 6 h. Cell viability was assessed by Calcein-AM dye added few min. before the completion of 6 h. then photographs at 10×magnification were taken using an inverted microscope. The tubule length of HUVECs was quantified by Leica QWin software. Tubule network formation is expressed as a percentage of that vehicle (0.1% DMSO) treated cells (control). Graphs were plotted and data are represented as mean±SEM with significant difference from sunitinib (50 nM) at $*p<0.05$.

To examine the effect of Compound 1 on angiogenesis, capillary tube formation assay was performed on regular or reduced growth factor Matrigel, taking VEGF (50 ng/mL) treated cells as a positive control and sunitinib (50 nM) as a negative control (FIG. 2). HUVECs seeded onto the matrigel with compound 1 at different concentrations of (10 µM, 5 µM, 1 µM, 800 nM, 500 nM, 250 nM, 125 nM, 75 nM, 50 nM, 25 nM and 10 nM) were incubated for six hours. A complete tubulogenesis inhibition of treated endothelial cells with no toxic effect on the cells was observed till 500 nM concentration of compound 1. As light increase in the tubule formation at 250 nM which was consistent till 125 nM concentration, observed in treated cells. At 75 nM of compounds concentration 50% tubule formation as compared to control was observed. This was further reduced to a concentration of 25 nM that showed complete angiogenesis. Then further detailed endothelial tubule network assay was performed for different structural analogs of compound 1 to find the IC50 value that are listed in Table 1 from Compound 1 to compound 51. Taken together, these findings demonstrated that this synthetic compound 1, expresses a potent anti-angiogenic effect by remarkably inhibiting the tubule formation at a very low dose concentration.

TABLE 1

Anti-angiogentic activity of compounds 1-51 (IC50 values)

| S. No. | Compound name | IC50 value | remarks |
|---|---|---|---|
| 1 | Compound 1 | 75 nM | comparable to sunitinib |
| 2 | Compound 2 | 250 nM | |
| 3 | Compound 3 | Not Active | |
| 4 | Compound 4 | Not Active | |
| 5 | Compound 5 | 350 nM | |
| 6 | Compound 6 | 5 µM | |
| 7 | Compound 7 | 4 µM | |
| 8 | Compound 8 | 500 nM | |
| 9 | Compound 9 | 550 nM | |
| 10 | Compound 10 | 600 nM | |
| 11 | Compound 11 | 450 nM | |
| 12 | Compound 12 | 200 nM | |
| 13 | Compound 13 | 100 nM | comparable to sunitinib |
| 14 | Compound 14 | 750 nM | |
| 15 | Compound 15 | 800 nM | |
| 16 | Compound 16 | 800 nM | |
| 17 | Compound 17 | 400 nM | |
| 18 | Compound 18 | 400 nM | |
| 19 | Compound 19 | 800 nM | |
| 20 | Compound 20 | 750 nM | |
| 21 | Compound 21 | 750 nM | |
| 22 | Compound 22 | 600 nM | |
| 23 | Compound 23 | 600 nM | |
| 24 | Compound 24 | 700 nM | |
| 25 | Compound 25 | 700 nM | |
| 26 | Compound 26 | 500 nM | |
| 27 | Compound 27 | 100 nM | comparable to sunitinib |
| 28 | Compound 28 | 50 nM | comparable to sunitinib |
| 29 | Compound 29 | 250 nM | |
| 30 | Compound 30 | 250 nM | |
| 31 | Compound 31 | 250 nM | |
| 32 | Compound 32 | 50 nM | comparable to sunitinib |
| 33 | Compound 33 | 50 nM | comparable to sunitinib |
| 34 | Compound 34 | 250 nM | |
| 35 | Compound 35 | 250 nM | |
| 36 | Compound 36 | 250 nM | |
| 37 | Compound 37 | 50 nM | comparable to sunitinib |
| 38 | Compound 38 | 75 nM | comparable to sunitinib |
| 39 | Compound 39 | 2.5 µM | |
| 40 | Compound 40 | 500 nM | |
| 41 | Compound 41 | 1 µM | |
| 42 | Compound 42 | 25 nM | comparable to sunitinib |
| 43 | Compound 43 | 250 nM | |
| 44 | Compound 44 | 250 nM | |
| 45 | Compound 45 | 100 nM | comparable to sunitinib |
| 46 | Compound 46 | 500 nM | |
| 47 | Compound 47 | 500 nM | |
| 48 | Compound 48 | 250 nM | |
| 49 | Compound 49 | 250 nM | |
| 50 | Compound 50 | 250 nM | |
| 51 | Compound 51 | 100 nM | comparable to sunitinib |

Detailed Screening data of Compound 1

Compound 1 Exhibited no Post Endothelial Mediated Tubule Disruption Activity

Figure 3:
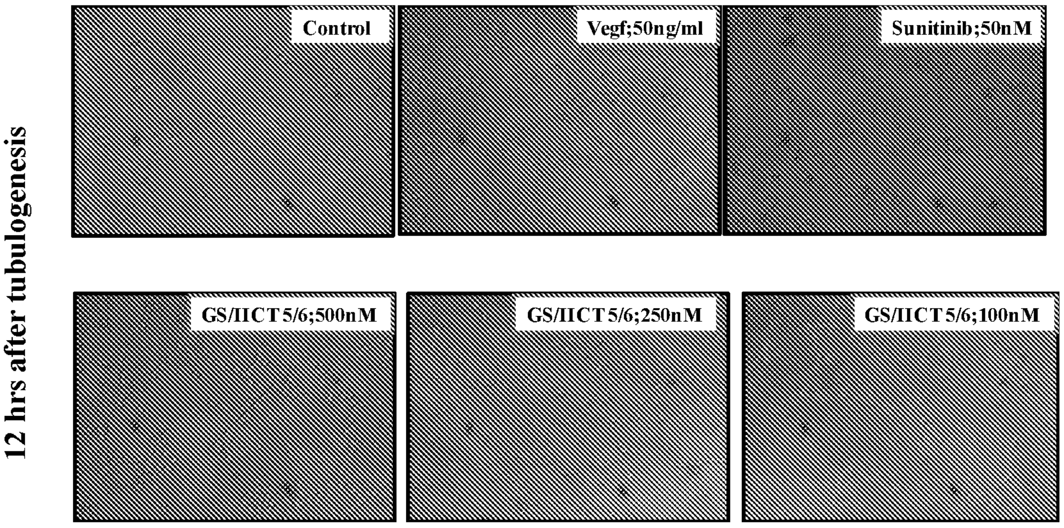
FIG. 3 represents effect of Compound 1 on post tubule formation by ECs. (A) ECs were incubated with indicated different concentrations of compound 1 along with VEGF (50 ng/mL) and sunitinib (50 nM) after 6 h of treatment to the already formed tubule. Post treatment photographs were taken at using an inverted microscope at 10×magnification.

Next, we have checked the vascular disrupting activity of preformed tubules. Compound 1 could not be able to disrupt the preformed tubules, suggesting that this molecule could inhibit only the newly forming angiogenesis (FIG. 3).

Compound 1 Retards the Migration of Endothelial Cells

Figure 4:
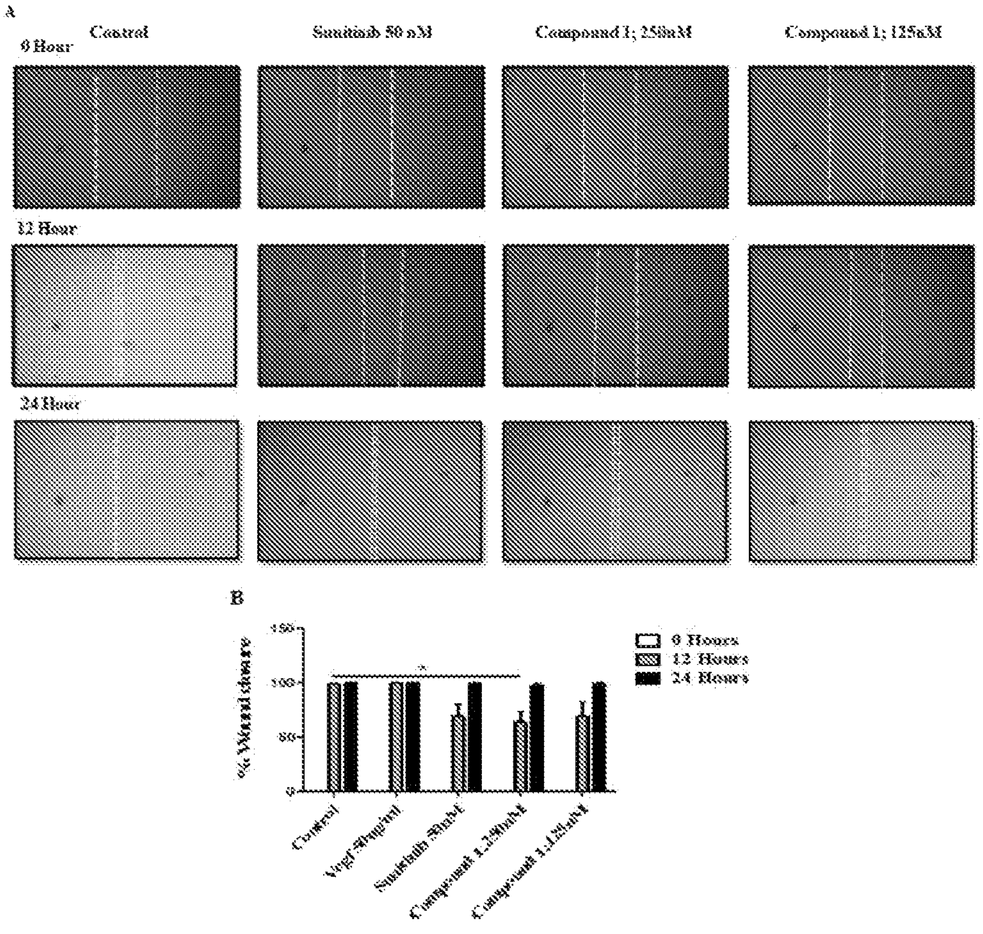
FIG. 4 represents In vitro wound closure assay showing effect of Compound 1 migration of HUVECs. (A) ECs were incubated with 2.5% FBS in the presence of VEGF, sunitinib and Compound 1 at the indicated concentrations for 24 h after linear scratched wounds were created in the confluent cells. Post treatment photographs were taken at 0 hr, 12 h and 24 h using an inverted microscope at 10×magnification. (B) Data were quantified using Image J software and graphs were plotted by calculating the % migration of that vehicle treated cells (control). Compound 1 inhibits the wound closure by ECs in a dose dependent manner. The values represent the mean±SEM from (n=3) independent experiments with significant difference compared from control at $*p<0.05$.

As per previous reports, some anti-angiogenic compounds also show anti-migratory effect by modulating the expression of proteins responsible for blood vessels formation. A Scratch was made to the confluent endothelial cells containing VEGF (50 ng/mL) and sunitinib (50 nM) as a positive and negative control respectively and Compound 1 at 250 nM and 125 nM as a test compound. 0%, 75% and 60% wound closure was observed at 0 nM, 125 nM and 250 nM respectively observed at 0 h and 12 h and complete migration was observed at 24 h of Compound 1 treated cells. 75% wound closure at 125 nM and 60% wound closure at 250 nM showed similar effect like sunitinib at 50 nM whereas control and positive control (VEGF at 50 ng/mL) have resulted 80% and 90% of wound closure effect. This result demonstrates that compound 1 have got a potent anti-migratory effect at a very low dose concentration till 12 h (FIG. 4). This might contribute to its potent anti-angiogenic effect.

Compound 1 Inhibits Tubule Formation in 3D Angiogenesis

Figure 5:
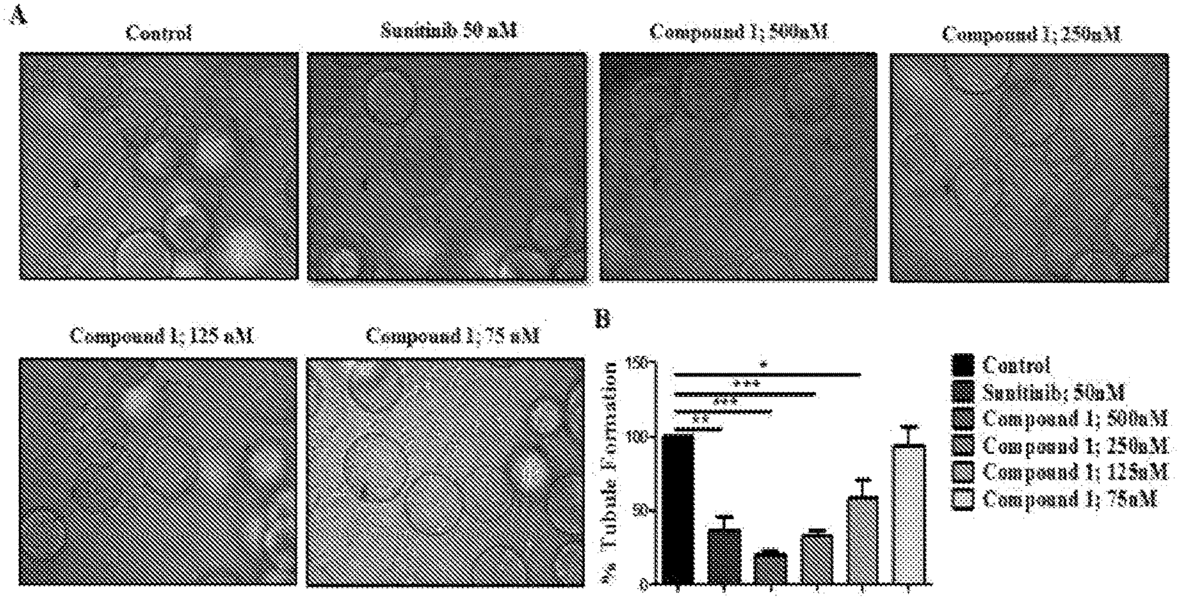
FIG. 5: Compound 1 exhibits reduced in-vitro 3D angiogenesis by HUVECs. (A) ECs were seeded on fibrinogen matrix and were treated with sunitinib and compound 1 at indicated concentrations. Post 5 days of incubation pictures were taken at 10× using inverted microscope. (B) Tube length was quantified using Leica QWin software and graph was plotted taking control (0.01% DMSO) treated cells. Data are represented as mean±SEM with significant difference from control at $*p<0.05$, $p<0.01$ and $*p<0.001$.

Anti-angiogenic effect of Compound 1 was further validated by 3D angiogenesis assay (FIG. 5). Cytodex beads coated with ECs in fibrin matrix showed tubulogenesis inhibitory effect of Compound 1 at 500 nM, 250 nM, 125 nM and 75 nM as compared to control that showing 100% tubule formation. A 100% tubule formation similar to control was observed at 75 nM concentrations. Hence the observed results again further validated the anti-angiogenic effect of Compound 1 on ECs in 3D environment.

Figure 6:
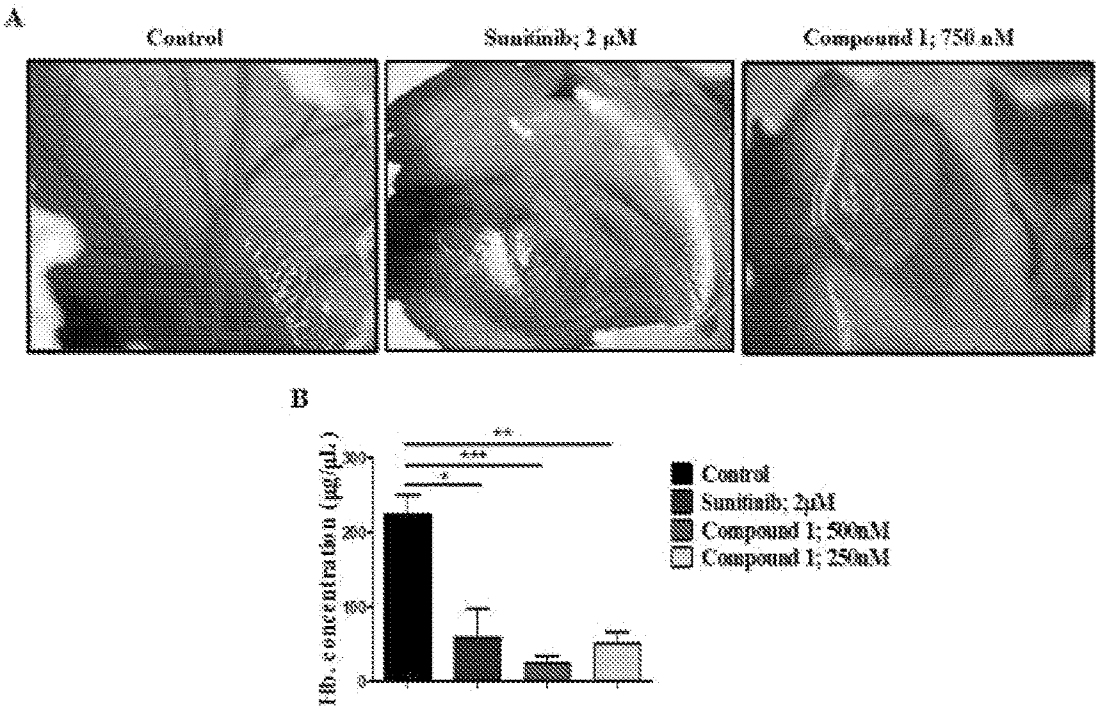
FIG. 6: Compound 1 treatment suppressed neovascularisation in the chick CAM. (A) Chick CAM assays were used to observe the effect of Compound 1 on angiogenesis in vivo. 1 $mm^2$ window was made in 8 days old chicken eggs to expose the CAM, and a gelatin disc (1 $mm^2$ diameter) treated with vehicle (0.1% DMSO), sunitinib and Compound 1 at a indicated concentrations were placed on the CAM surface. Post 4 days of incubation, the discs and associated CAM were photographed and excised out, for hemoglobin estimation by drapkin's reagent. (B) Blood vessel density was calculated and Hb. concentration was measured and representative graph was plotted for the control and treatment group and data are represented as mean±SEM with significant difference from control at $*p<0.05$, $p<0.01$ and $*p<0.001$.

CAM (Chick Chorio-Allantoic Membrane) Assay Demonstrated Diminished Neo-Vascularization by Compound 1 Treatment The anti-angiogenic effect of compound 1 was further confirmed by CAM assay that inhibit the formation of new blood vessels onto the CAM membrane that provides the nourishment to the developing chick embryo (FIG. 6). Compound 1 treatment at 500 nM and 250 nM have suppressed blood vessels density and reduced hemoglobin content to 50-60 μg/mL as compared to sunitinib (2 μM) showing 100 μg/mL of Hb. Increased neovascularization in the CAM along with a high Hemoglobin content of 200 μg/mL was observed in control cells which is very high as compared to Compound 1 as well as sunitinib. Hence, Compound 1 again proved to be a potent anti-angiogenic compound through inhibiting the blood vessels formation in the CAM.

Compound 1 Prevented the In Vivo Blood Vessel Formation

Figure 7:
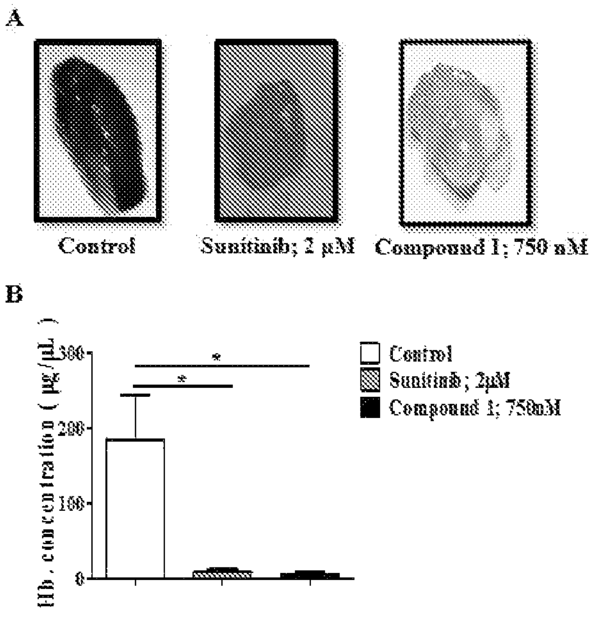
FIG. 7: Compound 1 treatment inhibited VEGF-induced neo-angiogenesis in vivo. (A) Post 7 days treatment of control (0.1% DMSO), sunitinib and Compound 1 at a given concentration, the mice was sacrificed and representative Matrigel plugs were excised and photographed. (B) Hemoglobin estimation was performed using drapkin's reagent and graph was plotted with data that are represented as mean±SEM from three independent experiments with significant difference from control at $*p<0.05$ using t-test analysis.

Apart from in vitro, Compound 1 also exhibited its anti-angiogenic effect in vivo through matrigel plug assay. Matrigel injected along with Compound 1 at 750 nM concentration into the dorsal skin of the mice exhibited significant reduction in blood vessels formation through the implanted Matrigel (FIG. 7). The phenotypic reduction of angiogenesis by Compound 1 was also validated through the hemoglobin estimation that had resulted to 10-15 g/mL hemoglobin concentration that is comparable to sunitinib at (2 μM) while control mice displayed more than 200 μg/mL of hemoglobin content which was significantly increased as compared to Compound 1. Therefore, this data has clearly shown the potent anti-angiogenic effect of Compound 1 in vivo.

Compound 1 Displayed Reduced Ear Angiogenesis

Figure 8:
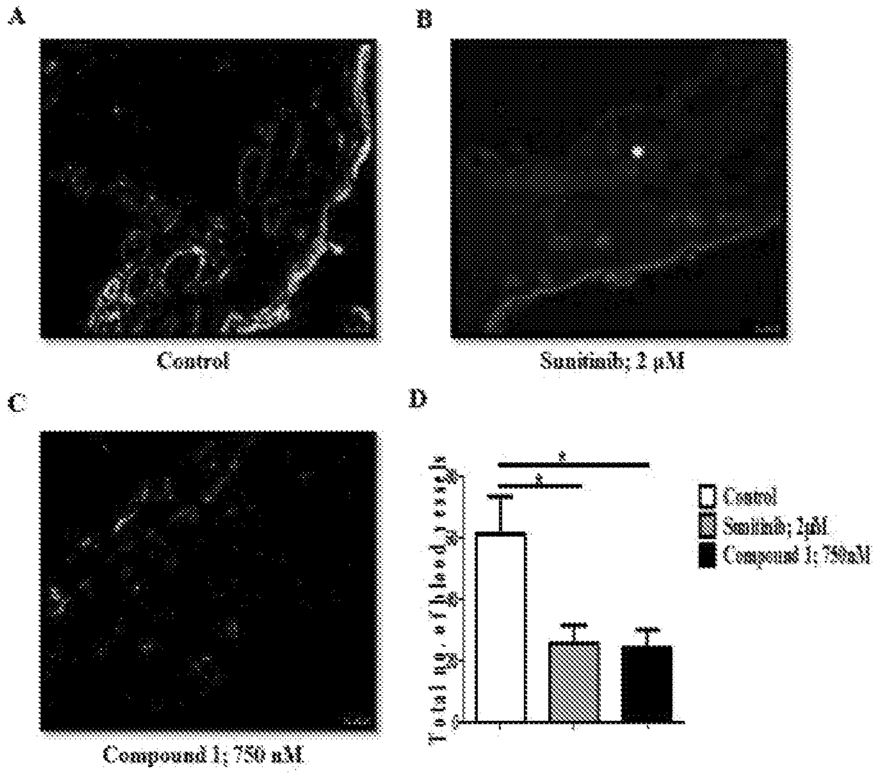
FIG. 8: Compound 1 treatment suppressed VEGF-induced ear vascularizationin vivo. (A) Control (0.1% DMSO), (B) sunitinib and (C) Compound 1 at their indicated concentration dissolved in 100 μL of 1×PBS injected into the flanks of Balb/c mice (5 mice/treatment group). After 7 days of treatment ears were harvested, cryo-sectioned at 5 μM thickness. CD31 immunostained and photographed under inverted microscope at 20× magnification. (B) Vasculature was quantified by counting total macro and micro blood vessels. Plotted graph is representative of four independent experiments and are represented as mean±SEM with significant difference compared with control at $*p<0.05$.

As VEGF induced vessel permeability is one of the crucial parts of angiogenesis, so the anti-angiogenic effect of Compound 1 on VEGF induced micro-vessels formation in Balb/c mice through ear angiogenesis assay was performed (FIG. 8). The obtained results revealed that control group mice receiving 1×PBS along with VEGF and bFGF expressed increased micro-vessels density as shown by PECAM1 or CD31 staining of frozen ear sections but the presence of Compound 1 at 750 nM along with VEGF and bFGF, reduced CD31 expression and micro-vessels density. A similar inhibitory effect was observed with the sunitinib at 2 μM concentration. This clearly implies that Compound 1 could inhibit the formation of VEGF induced vasculature in vivo at much lower concentration than sunitinib proving it to be better anti-angiogenic agent than sunitinib.

Combinatory Dose of Chiral Isomers (1-1) and (2-1) of Compound 1 Potentiates the Anti-Angiogenic Activity on HUVECs Isomer (1-1) means chiral isomer 1 of racemic compound 1;

Isomer (2-1) means chiral isomer 2 of racemic compound 1.

Chiral isomer 1

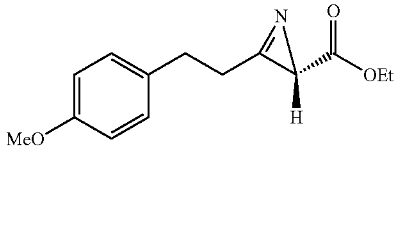

-continued

Chiral isomer 2

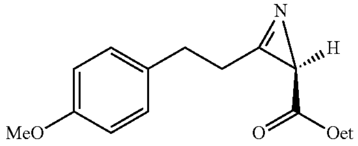

Figure 9:
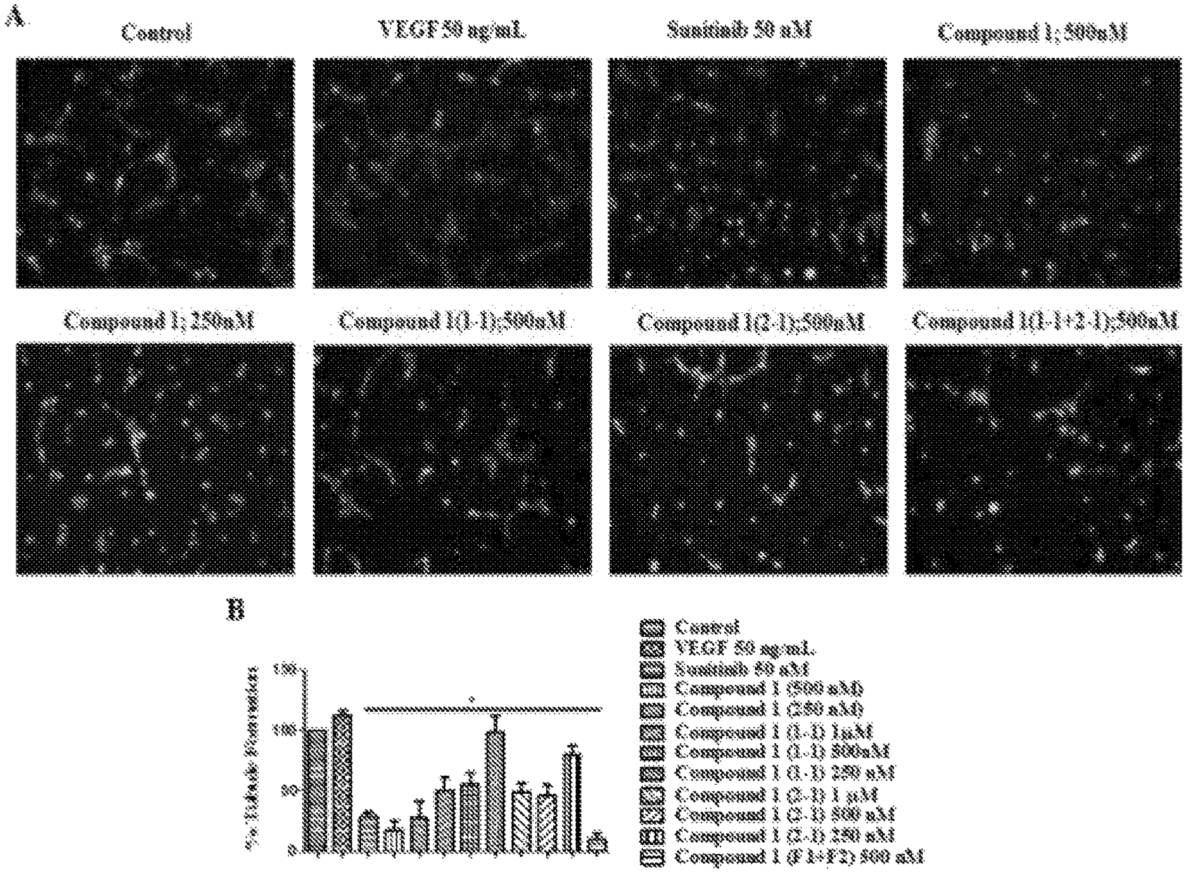
FIG. 9 represents effect of racemic mixture (chiral isomer 1-1 and chiral isomer 2-1) of Compound 1 on capillary tube formation of HUVECs. Endothelial cells seeded in matrigel were incubated at the indicated concentrations of compound 1 racemic mixtures (1-1 and 2-1) with ECM basal medium for 6 h. Calcein-AM treatment was added to the ECs few minutes before completion of 6 h and pictures were captured using an inverted microscope at 10×magnification. The tubular structures of HUVECs were measured using Leica QWin software and tubulogenesis was expressed as a % of that vehicle (0.1% DMSO) treated cells (control) well. Data are represented as mean±SEM with significant difference from sunitinib (50 nM) at $*p<0.05$.

As previously, the anti-angiogenic activity of Compound 1 has already been confirmed by various approaches, it becomes mandatory to check the anti-angiogenic effect of the chiral isomers (1-1 and 2-1) of Compound 1 (FIG. 9). To confirm this ECs treated with different concentrations of chiral isomers (1-1 and 2-1) of Compound 1 (racemic) (1 μM, 500 nM and 250 nM) individually as well in combination. As observed before, Compound 1 at 500 nM and 250 nM showed effective tubulogenesis inhibition with 15% and 25% tubule formation respectively. Chiral isomer (1-1) at 1 μM concentration showed 50% angiogenesis, similar result was observed at 500 nM concentration and the activity was further lost at lower dose of 250 nM that showed no reduction in tubulogenesis and showing 100% tubule formation. Almost similar trend was observed with chiral isomer (2-1) at 1 μM and 500 nM showing 50% tubulogenesis and at 250 nM concentration showing 100%. But interestingly the combination of chiral isomers 1-1 and 2-1 at (500 nM) concentration, expressed potent and significant anti-angiogenic activity, compared with sunitinib at 50 nM with 25% tubule formation. Hence this data has clearly shown the combined effect of chiral isomers (1-1) and (2-1) possess a powerful anti-angiogenic property in comparison to their alone activity.

Figure 10:
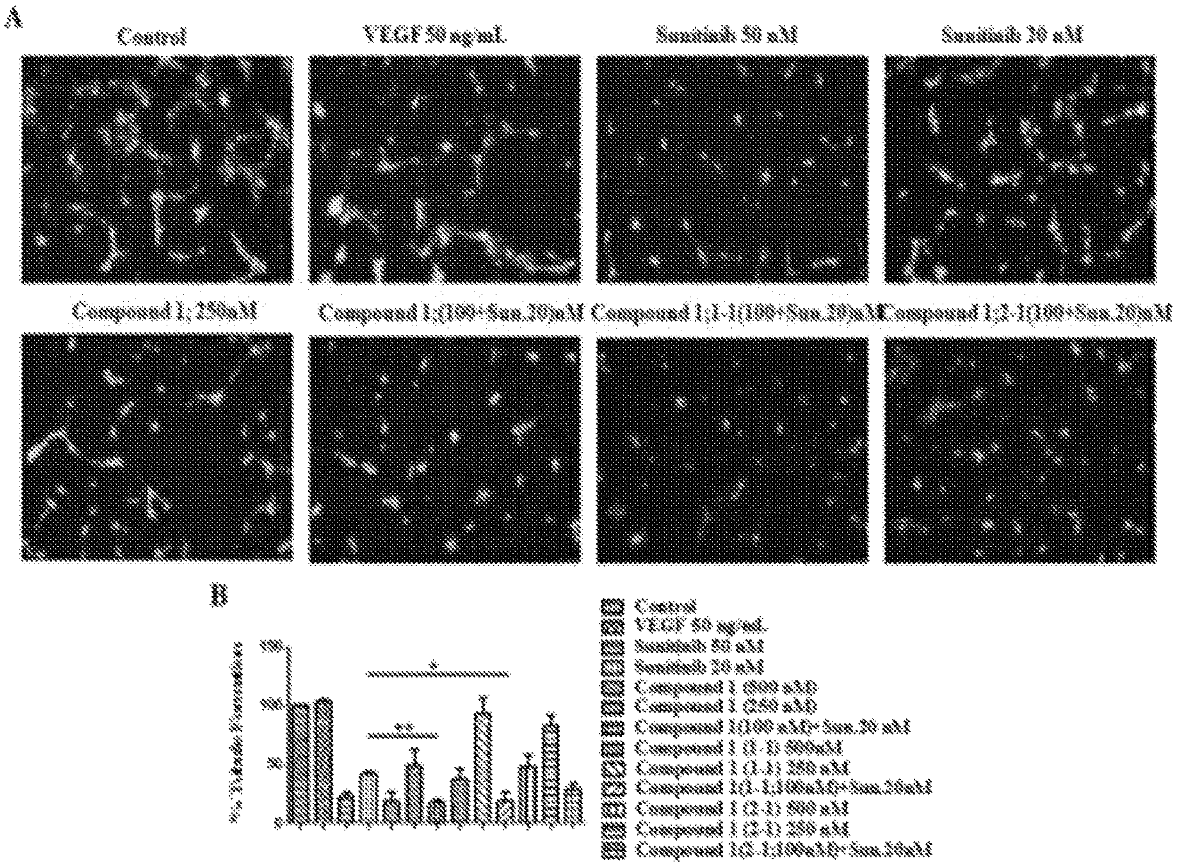
FIG. 10 represents effect of co-treatment of chiral isomers of Compound 1 (chiral isomer 1-1 and chiral isomer 2-1) and sunitinib at lower dose concentration on capillary tube formation of HUVECs. HUVEC cells were incubated with or without sunitinib (20 nM) for 6 h at indicated concentrations of chiral isomers of Compound 1 (1-1 and 2-1). Photographs were taken using an inverted microscope at 10×magnification after Calcein-AM treatment to the ECs few minutes before completion of 6 h. The tubule length of HUVECs was quantified by Leica QWin software represented as a % of that vehicle (0.1% DMSO) treated cells (control) well. Data are represented as mean±SEM from (n=3) independent experiments with significant difference compared from sunitinib (20 nM) at $*p<0.05$.

Synergistic Effect of Chiral Isomers (1-1) and (2-1) and Sunitinib at Lower Doses Have Better Antiangiogenic Effect As it has been clearly demonstrated that chiral isomers (1-1) and (2-1) of compound 1 in combination have better anti-angiogenic effect at 500 nM in comparison to individual effect (FIG. 10). The effect of Compound 1 (racemic) and their chiral isomers (1-1) and (2-1) at 100 nM concentration combined with a low concentration of sunitinib (20 nM) were tested for anti-angiogenic effect. A similar trend of tubulogenesis with 50% of tubule formation was observed at 500 nM and 80-90% at 250 nM concentration of Compound 1 and its chiral isomers individually. Sunitinib was employed at 50 nM concentration that showed 25% tubulogenesis while 20 nM concentration of sunitinib showed 40% of tubule formation. As individual effect of Compound 1 (racemic) and its chiral isomers on angiogenesis were not as effective as it was expected, so it was decided to observe the combined effect of Compound 1 (racemic) and its chiral isomer (1-1) at 100 nM with sunitinib at 20 nM on angiogenesis that resulted in significant reduction in tubule formation to approximately 15%. However, isomer (2-1) at 100 nM along with sunitinib at 20 nM concentration showed a reduced tubulognesis to around 30%. Hence, the present data clearly demonstrates the increased anti-angiogenic effect of Compound 1 and its chiral isomers (1-1) and (2-1) in presence of low concentration of sunitinib could be beneficial against cancer treatment.

Reduced Expression of p-Src and p-VEGFR2 Might Contribute to Anti-Angiogenic Effect of Compound 1

Figure 11:
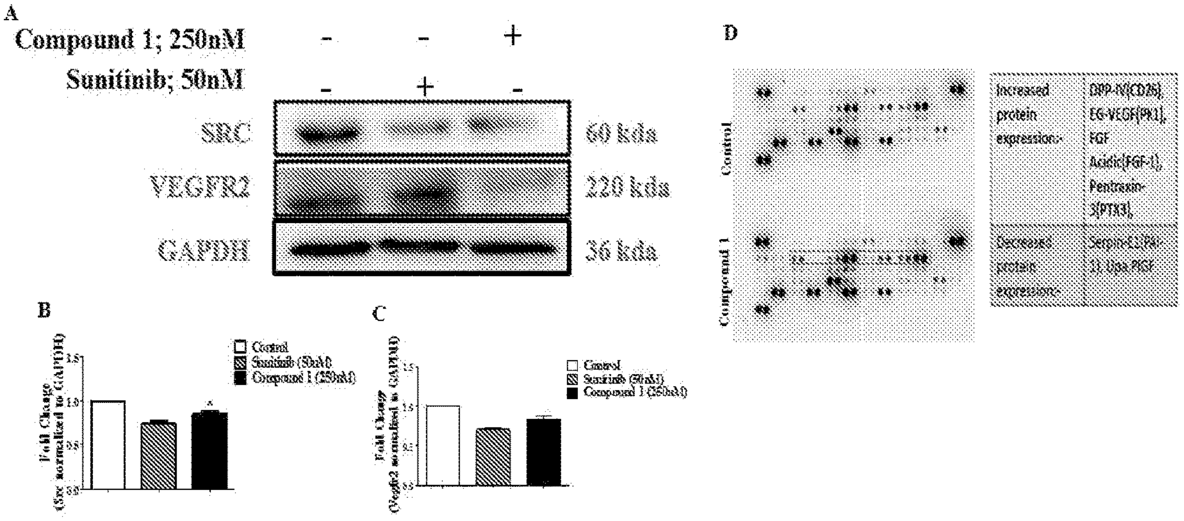
FIG. 11 represents Compound 1 treated HUVECs exhibits reduced Src-kinase and VEGFR2 expression. (A) Serum-starved HUVECs were treated with control (0.1% DMSO), sunitinib and Compound 1 at a given concentrations and then incubated for 6 h. The expression level of phospho-VEGFR2 and GAPDH (housekeeping protein) was analyzed by immunoblotting. (B) Blots were quantified with Image-J software and the bar graphs represent the relative density of phospho-VEGFR2 normalized with GAPDH and the data are represented as mean±SEM with significant difference compared with control at $*p<0.05$. (D) Protein angiogenesis array showing up-regulation of anti-angiogenic protein and down-regulation of pro-angiogenic proteins on endothelial cell treated with Compound 1 at 260 nM.

VEGFR2, a receptor tyrosine kinase mediates angiogenesis by binding to its ligand, VEGF that phosphorylates VEGFR2 and induces further downstream signaling responsible for angiogenesis. VEGFR2 expression as well as the expression of Src was checked in HUVECs as reported earlier both the proteins are very important in regulating the angiogenesis (FIG. 11). Immuno blotting revealed marked reduction in Src-kinase and p-VEGFR2 expression with Compound 1 treatment at 250 nM. This expression is similar to known receptor tyrosine kinase inhibitor sunitinib at 50 nM. No change in the expression pattern of Src and VEGFR2 of the control sample was observed. Hence, this data clearly suggests that the Src-kinase and VEGFR2 inhibition could be the possible reason that imparts the anti-angiogenic and anti-migratory effect to Compound 1. To ascertain further, we performed the protein angiogenesis array on endothelial cell treated with Compound 1. We observed that this small molecule inhibitor has significantly increased the protein expression of anti-angiogenic proteins and decreased the expression of angiogenic proteins.

Figure 12:
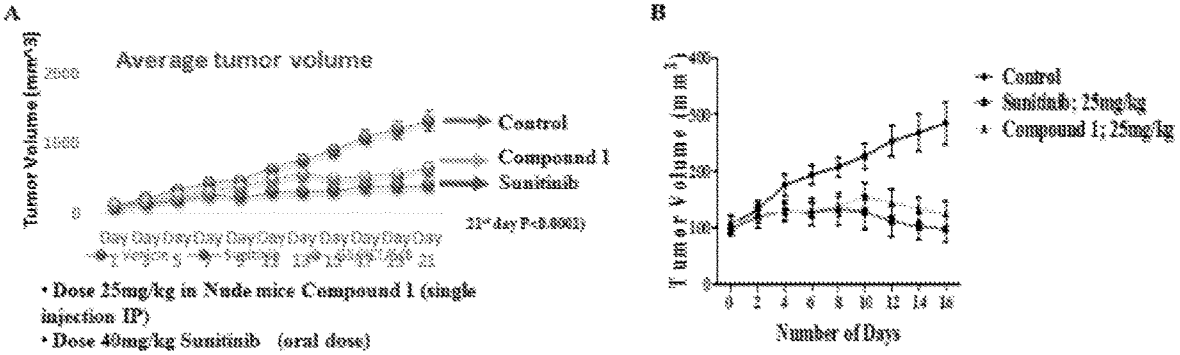
FIG. 12 represents Compound 1 inhibited tumor growth in vivo. Tumor sizes were recorded every alternate day by Vernier caliper measurements and calculated as [4/3*22/7*(length/2)*(width/2)]. (A) Nude mice with induced HCT116 tumor were given vehicle to the control group, sunitinib at (40 mg/kg) as a standard drug given orally and Compound 1 at (25 mg/kg) through IP route for 21 days and tumor regression was calculated for all groups. (B) Nude Mice with induced HCT116 colon tumor were given both, sunitinib and Compound 1 at (25 mg/kg) intra-muscularly for 15 days after attaining a tumor size of 100 $mm^3$, tumor volume reduction for treated groups were calculated and compared with control. Data are expressed as means±S.E.M. (6 mice/group) with significant difference compared with control at $p<0.0001$.
Figure 13:
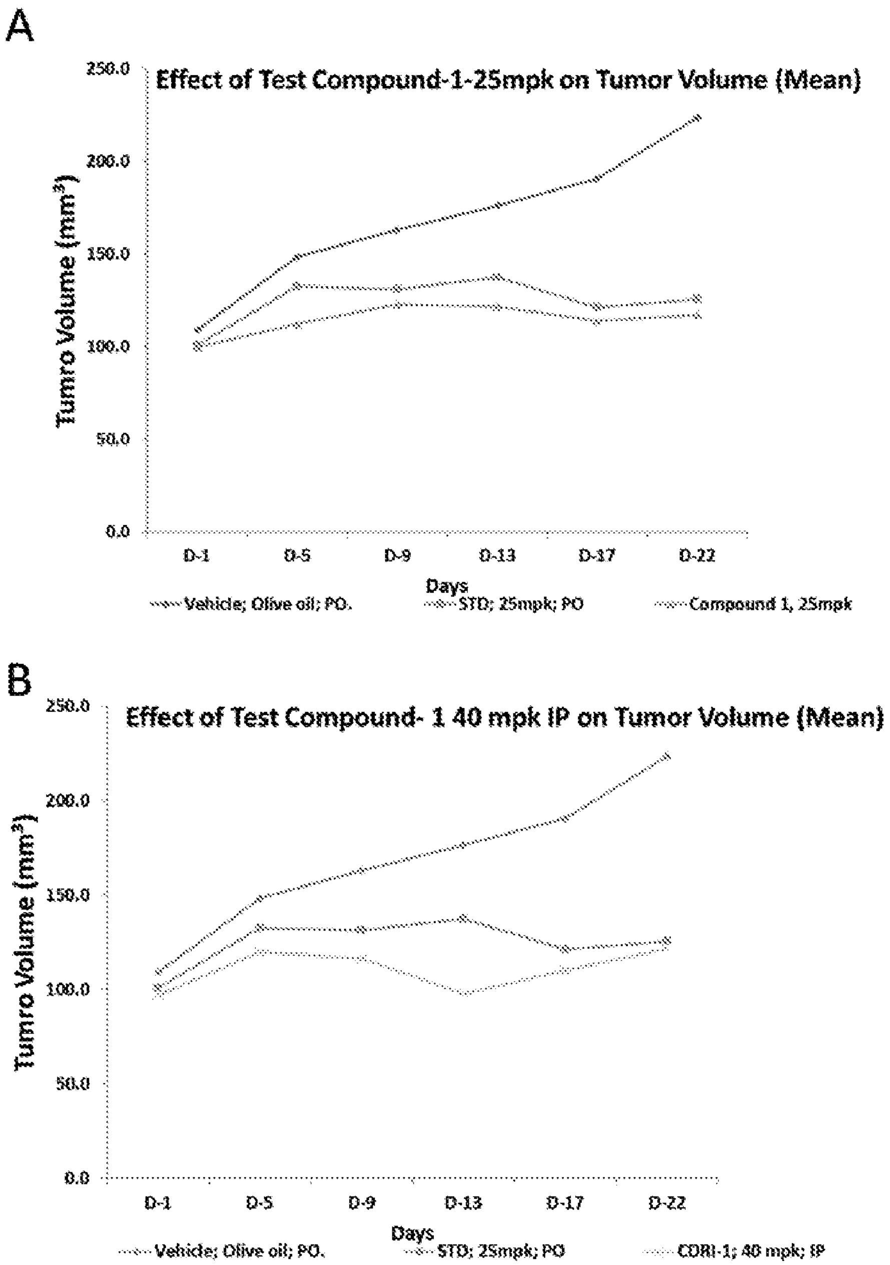
FIG. 13 represents Effect of Compound 1 on triple negative breast cancer celline MDA-MB 468 in xenograft mouse model. A. Compound 1, 25 mg/kg regresses tumor growth similar to that of sunitinib at different days. B. Compound 1, 40 mg/kg regresses tumor growth better than the standard compound sunitinib.

Compound 1 Effectively Reduces the Implanted Human Colon and MDA-MB 468 (Triple Negative Breast Cancer) Tumor Size in Nude Mice A nude mice model bearing orthotopic HCT116 colon tumor or MDA-MB 468 was used to evaluate the anti-tumor angiogenesis effect of Compound 1 in vivo (FIG. 12). (A) Nude mice with HCT 116 colon tumor were treated with sunitinib at 40 mg/kg was given orally and compound 1 at 25 mg/kg injected through IP route for 21 days that resulted in progressive significant decrease in tumor volume in comparison to vehicle (olive oil) injected IP to the mice with tumor. (B) Compound 1 and sunitinib at (25 mg/kg) treatments showed powerful inhibitory effect on the growth of HCT116 cells xenografts in nude mice. Values of T/C in the Compound 1 (25 mg/kg) group were 94.77% (day 2), 72.79% (day 4), 67.93% (day 6), 66.22% (day 8), 68.70% (day 10), 56.83% (day 12), 49.80% (day 14) and 43.88% (day 16) suggesting that Compound 1 inhibited tumor growth in a dose-dependent manner during the 15-d treatment. Similarly, Compound 1 (25 mg/kg and 40 mg/kg) reduced the tumor growth of MDA-MB 468 triple negative breast cancer cell line, similar or better than the standard compound sunitinib (FIG. 13). Finally, the experiment showed tumor reduction of 62.02% by Compound 1 and 54.58% by sunitinib in comparison to vehicle treated control group. To investigate the effects of Compound 1 on angiogenesis and molecular targets in vivo, we examined the expression level of endothelial-specific marker (CD31) in tumor samples. Most noticeably, histological analysis of sections stained with an endothelial-specific antibody (CD31) showed that Compound 1 (25 mg/kg) reduced the vascular density in tumor tissues compared with the control group. Altogether, these results further supported that Compound 1 strongly inhibited growth of orthotopic HCT116 colon tumor as well as MDA-MB 468 triple negative breast cancer in nude mice through inhibiting neo-vascularization in tumor tissue.

Compound 1 Treatment Modulates Thrombospondin 1 and Endothelin 1 Gene Expression in HUVECs Modulation in the number of genes and their expression was observed in compound 1 treated HUVECs by mRNA sequence analysis. Heat map graph clearly demonstrates that the genes that are commonly up-regulated and the ones that are down-regulated with Compound 1 treatment at all concentrations (10 μM, 1 μM, 500 nM and 250 nM) with respect to control samples of HUVECs have summarized in Table 2. The gene expression that was observed to be up-regulated and down regulated genes in the tumor samples treated with Compound 1 at 25 mg/kg for 15 days with respect to control samples are summarized in Table 3. Amongst all the genes those were modulated by the treatment of Compound 1, Thrombospondin gene is one of them whose up-regulation is well reported to inhibit angiogenesis. Therefore, this data implies that Thrombospondin 1 could be one of the crucial molecular targets that is being regulated by Compound 1 molecule and exhibiting its anti-angiogenic effect.

TABLE 2

Expression of up-regulated and down-regulated genes after Compound 1 treatment in HUVECs

| S. No. | Up regulated Gene name | S. No. | Down regulated Gene name |
|---|---|---|---|
| 1 | two pore segment channel 1 (TPCN1) | 1 | ATPase family (ATAD3A), AAA domain containing 3A (ADC3A) |
| 2 | staufen double-stranded RNA binding protein 2 (STAU2) | 2 | elaC ribonuclease Z 2 (ELAC2) |
| 3 | methylenetetrahydrofolate dehydrogenase (NADP+ dependent) 1-like (MTHF1L) | 3 | family with sequence similarity 53 member (FAM53C) |
| 4 | mitogen-activated protein kinase 7 (MAPK7) | 4 | notchless homolog 1 (NLE1) |
| 5 | argininosuccinate lyase (ASL) | 5 | receptor type K (PTPRK) |

TABLE 3

Expression of up-regulated and down-regulated genes in Compound 1 treated Tumors

| S. No. | Up regulated Gene name | S. No. | Down regulated Gene name |
|---|---|---|---|
| 1 | apoptotic peptidase activating factor 1 (APAF1) | 1 | armadillo repeat containing, X-linked 3 (ARMCX3) |
| 2 | mitogen-activated protein kinase 14 (MAPK14) | 2 | bromodomain adjacent to zinc finger domain 2B (BAZ2B) |
| 3 | mitogen-activated protein kinase kinase kinase kinase 2 (MAP4K2) | 3 | mitogen-activated protein kinase kinase 7 (MAP2K7) |

TABLE 3-continued

| Expression of up-regulated and down-regulated genes in Compound 1 treated Tumors | | | |
|---|---|---|---|
| S. No. | Up regulated Gene name | S. No. | Down regulated Gene name |
| 4 | nucleolar protein 8 (NOL8) | 4 | protein tyrosine phosphatase |
| 5 | TNFAIP3 interacting protein 1 (TNIP1) | 5 | CD36 molecule (thrombospondin receptor) (CD36) |
| 6 | zinc finger protein 131 (ZNF131) | 6 | elaC ribonuclease Z 2 (ELAC2) |
| 7 | abl interactor 1(ABI1) | | |

Drug Affinity Receptor Target (DART) Analysis Confirmed the Involvement of Thrombospondin 1 and Endothelin 1 in Compound 1 Mediated Anti-Angiogenesis Intact protein band was observed in Compound 1 10 mM lane whereas no band in control lane at the same position was observed. This could be due to the binding of drug to the protein lysate that has protected them against the protease digestion whereas control sample with same volume of vehicle has undergone complete protease digestion that leads to absence of any band in the control lane. LC/MS-MS analysis for the excised band from Compound 1 sample has revealed several proteins that were bounded by the drug. According to the PLGS score the proteins involved in angiogenesis are summarized in Table 4 given below. Amongst these obtained proteins Thrombospondin 1, Endothelin, Angiopoietin well known to be involved in the regulation of angiogenesis. Hence, DART analysis once again confirmed the mRNA sequence analysis data that thrombospondin1, endothelin and angiopoetin are the protein target that are being regulated by Compound 1 and imparting it an anti-angiogenic effect.

TABLE 4

| DART analysis showing protein sequence found for HUVECs treated with Compound 1 | | |
|---|---|---|
| S. No. | Protein code | PLGS Score |
| 1 | Solute carrier organic anion transporter family member (SO6A1) | 172.24 |
| 2 | Arf-GAP with GTPase, ANK repeat and PH domain-containing protein (AGAP2) | 133.917 |
| 3 | Rho GTPase-activating protein 5 (RHG05) | 123.896 |
| 4 | Thrombospondin type-1 (THSD1) | 61.3797 |
| 5 | Mitogen-activated protein kinase 7 (MAPK7) | 35.8921 |
| 6 | Endothelin-converting enzyme 2 (ECE2) | 20.3571 |
| 7 | Armadillo repeat-containing protein 2 (ARMC2) | 10.7788 |
| 8 | Angiopoietin-4 (ANGP4) | 9.0398 |

Figure 14:
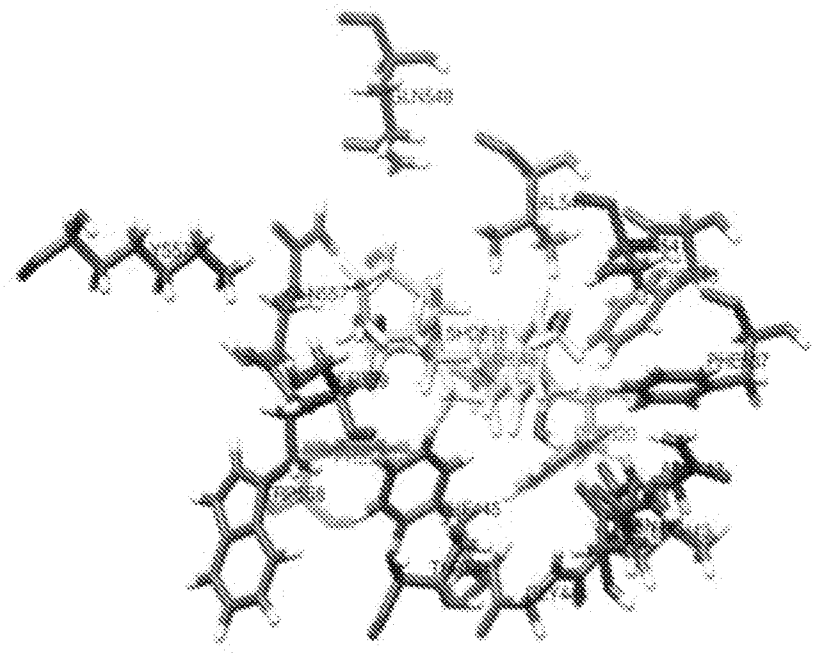
FIG. 14 represents 3D molecular structure for Compound 1.

3D Molecular Docking Reveals the Possible Active Site of Endothelin Protein Modulated by Compound 1 for its Anti-Angiogenic Effect (FIG. 14).

Figure 15:
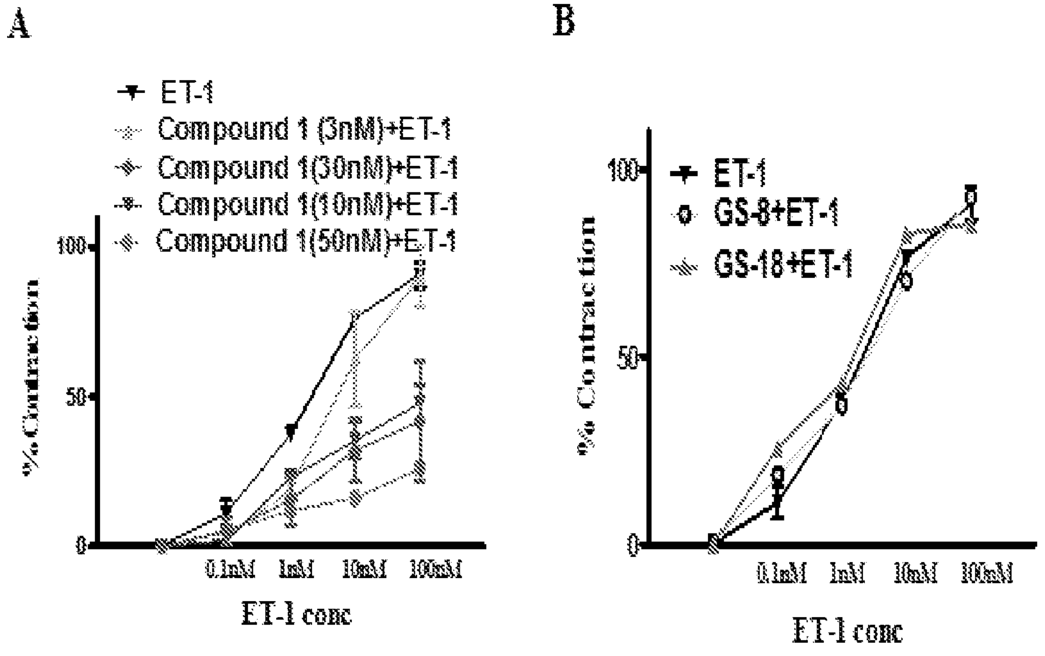
FIG. 15 represents effect of Compound 1 on endothelin-1 concentration-response curves. (A) Concentration-response curve of endothelin-1 in isolated carotid arteries of vehicle-treated (Control) and Compound 1 treated mice. (B) Concentration-response curve of endothelin-1 in isolated carotid arteries of vehicle-treated (Control) and compound 3 along with compound 8 treated mice.

Compound 1 Imparts its Anti-Angiogenic Property by Regulating Endothelin-1 Receptor of Endothelial Cells To test for the selectivity of the putative Endothelin-1 receptor, we applied endothelin-1 or Compound 1 in a concentration dependent manner to the aortic ring to observe its contraction inhibition activity (FIG. 15). Compound 1 as a possible antagonist of ET-1 receptor, initiated the inhibition of ET-1 mediated contraction at a low concentration of 3 nM, that subsequently decreases the % contraction of aortic ring to about 35% and 25% at 10 nM and 30 nM of Compound 1 with increased concentration of ET-1 at 100 nM. Finally, Compound 1 at 50 nM resulted in significant decrease of % contraction of aortic ring to about 20% even in presence of ET-1 at 100 nM concentration. The ET-1 inhibitory efficacy was also tested for other isomer of this compound series, so compound 3 and compound 8 were also employed that showed no effect as compound 1 at all concentrations of ET-1 induced contraction of aortic rings. Therefore, the present data suggest, ET-1 activity modulation by Compound 1 could be the possible target behind its anti-angiogenic effect.

Pharmacokinetic Assessment of Compound 1 and its Chiral Isomers 1 and 2 after Intramuscular Administration In Vivo Pharmacokinetic Study In vivo pharmacokinetic study was performed in male Sprague Dawley (SD) rats (n=4). Intramuscular (IM) formulation of compound 1 Chiral 1 and 2 were prepared by individually dissolving accurately weighed quantity of compound 1, chiral isomers 1 and 2 (20 mg) in 1 mL of olive oil followed by vortexing for 2 min and sterilize through syringe filter. Blood samples were collected from the retro orbital plexus of rats under light ether anesthesia into microfuge tubes containing heparin as an anti-coagulant at 0.25, 0.5, 1, 3, 5, 7, 9, 24, 30, 48 and 72 hours post-dosing after intramuscular dose. Plasma sample was harvested by centrifuging the blood at 13000 rpm for 10 min on Sigma 1-15 K (Frankfurt, Germany) and stored frozen at −70±10° C. until bioanalysis. Each plasma sample (100 µl) was processed using protein precipitation method using 200 µl acetonitrile containing medicarpine as internal standard (I.S.) as protein precipitant, and 10 µl of the supernatant was injected for LC-MS/MS.

Results and Discussion

In Vivo Pharmacokinetics

Figure 16:
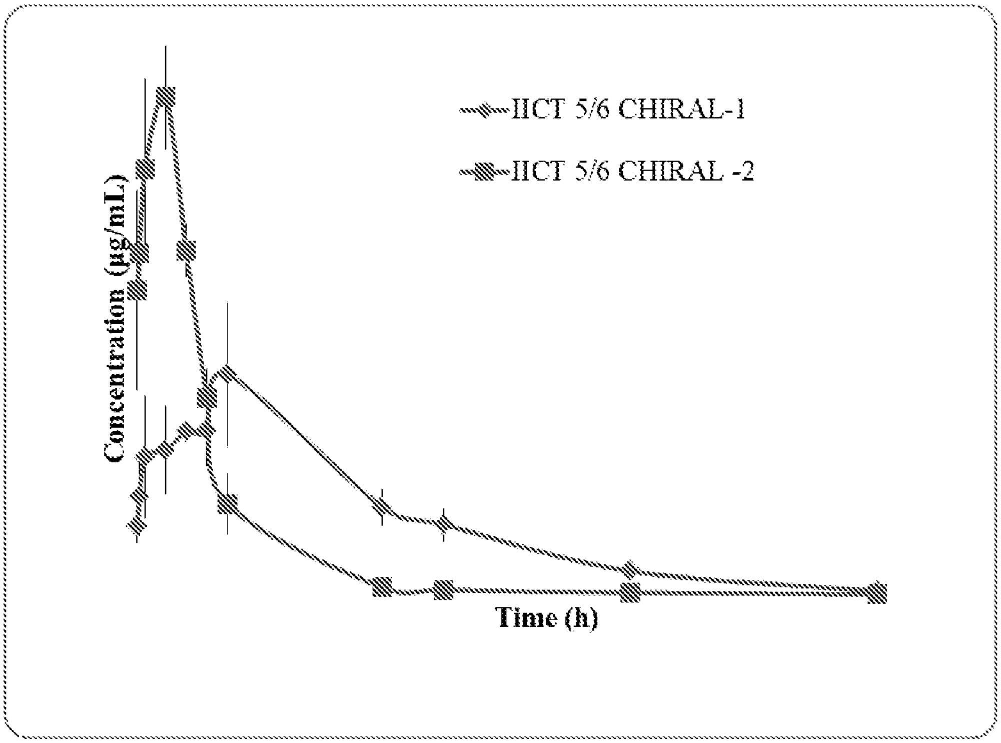
FIG. 16 represents intramuscular pharmacokinetic profiles of Chiral isomers-1 and 2 of compound 1 at 20 mg/Kg dose in male SD rats (n=4, each).

The mean plasma concentration-time profiles of compound 1 are shown in the table 5 and FIG. 16 and their estimated pharmacokinetic parameters are represented in the table 6. After intramuscular administration at 20 mg/kg dose, the max plasma concentration of Chiral isomers 1 and 2 was found to be 4.81±1.56 and 10.82±1.13 µg/mL, respectively. Furthermore, the apparent volume of distribution ($V_d$) and clearance (Cl) of Chiral isomers 1 and 2 were found to be 3.2±0.84 L/kg, 0.16±0.03 L/h/kg and 3.9±0.24 L/kg, 0.23±0.01 L/h/kg respectively. AUC 0-∞ (h*µg/mL) were found to be high upon IM route of administration of chiral isomer-1 at 20 mg/kg dose (120.65±24.09) as compared to chiral isomer-2 (85.48±6.1). The time taken for the systemic levels to reduce to half (half-life, ti/2) of chiral isomers 1 and 2 were found to be 13.27±1.51 h and 9.14±0.12 h, respectively.

TABLE 5

Time vs plasma concentration data of compound 1 chiral isomers 1 and 2 after intramuscular dose at 20 mg/kg dose.

| | Concentration (μg/mL) | |
|---|---|---|
| Time (h) | Chiral-1 | Chiral-2 |
| 0.25 | 1.52 ± 0.36 | 6.64 ± 2.17 |
| 0.5 | 2.15 ± 0.83 | 7.44 ± 0.40 |
| 1 | 3.02 ± 1.33 | 9.27 ± 1.96 |
| 3 | 3.17 ± 0.94 | 10.82 ± 1.13 |
| 5 | 3.57 ± 0.10 | 7.5 ± 0.56 |
| 7 | 3.58 ± 0.75 | 4.3 ± 0.62 |
| 9 | 4.81 ± 1.56 | 2.0 ± 0.66 |
| 24 | 1.93 ± 0.38 | 0.18 ± 0.013 |
| 30 | 1.55 ± 0.36 | 0.13 ± 0.015 |
| 48 | 0.545 ± 0.09 | 0.076 ± 0.004 |
| 72 | 0.11 ± 0.04 | 0.044 ± 0.006 |

TABLE 6

Pharmacokinetic parameters of compound 1 upon intramuscular administration. Data represented as mean ± S.D. (n = 4, each)

| Parameters | Compound 1 Chiral isomer-1 | Compound 1 of Chiral isomer-2 |
|---|---|---|
| $t_{1/2}$ (h) | 13.27 ± 1.51 | 9.14 ± 0.12 |
| $C_{max}$(μg/mL) | 4.81 ± 1.56 | 10.82 ± 1.13 |
| $T_{max}$ (h) | 9 | 3 |
| $AUC_{0-72}$ (h*μg/mL) | 118.49 ± 24.83 | 84.90 ± 6.02 |
| $AUC_{0-\infty}$ (h*μg/mL) | 120.65 ± 24.09 | 85.48 ± 6.1 |
| Cl (L/h/kg) | 0.16 ± 0.03 | 0.23 ± 0.01 |
| $V_d$ (L/kg) | 3.2 ± 0.84 | 3.9 ± 0.24 |

Pharmacokinetic Assessment of Bulk Compound 1, Chiral Isomer-1 of Compound 1 and Chiral Isomer-2 of Compound 1 after Intramuscular Administration In Vivo Pharmacokinetic Study In vivo pharmacokinetic study was performed in male Sprague Dawley (SD) rats (n=4). Intramuscular (IM) formulation of bulk of compound 1 as well as chiral isomer-1 and chiral isomer-2 was prepared by dissolving accurately weighed quantity of compound 1 (20 mg) in 1 mL of olive oil followed by vortexing for 2 min and sterilize through syringe filter. Blood samples were collected from the retro orbital plexus of rats under light ether anesthesia into microfuge tubes containing heparin as an anti-coagulant at 0.25, 0.5, 1, 3, 5, 7, 9, 24, 30, 48 and 72 hours post-dosing after intramuscular dose. Plasma sample was harvested by centrifuging the blood at 13000 rpm for 10 min on Sigma 1-15 K (Frankfurt, Germany) and stored frozen at −70±10° C. until bioanalysis. Each plasma sample (100 μl) was processed using protein precipitation method using 200 μl acetonitrile containing medicarpine as internal standard (I.S.) as protein precipitant, and 10 μl of the supernatant was injected for LC-MS/MS.

Results and Discussion

In Vivo Pharmacokinetics

Figure 17:
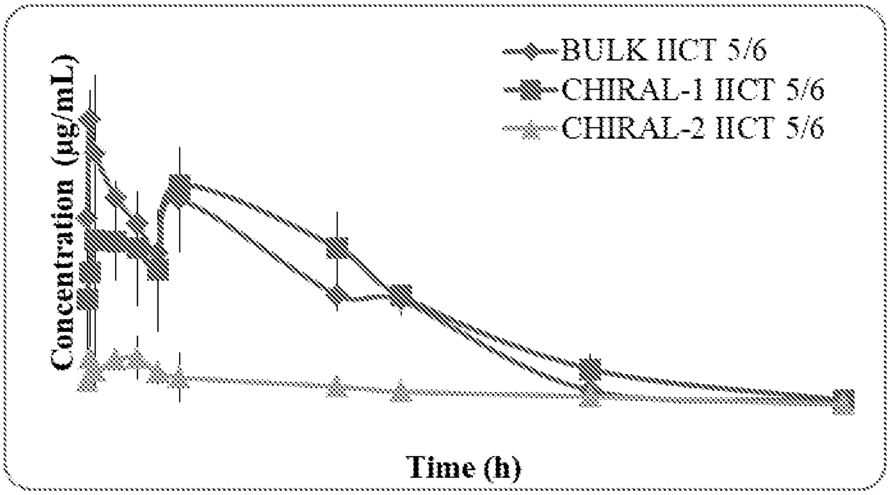
FIG. 17 represents intramuscular Pharmacokinetic Profiles of Bulk compound 1 (racemic) as well as Chiral isomer-1 and Chiral isomer-2 of compound 1 at 20 mg/Kg dose in male SD rats (n=4, each).

The mean plasma concentration-time profiles of compound 1 are shown in the table 7 and FIG. 17 and their estimated pharmacokinetic parameters are represented in the table 8. After intramuscular administration at 20 mg/kg dose, the max plasma concentration (C max) of Compound 1 (racemic), Chiral isomer-1 and 2 was found to be 4.62±0.435, 3.91±0.847 and 0.945±0.143 μg/mL, respectively. Furthermore, the apparent volume of distribution ($V_d$) of compound 1 (racemic), Chiral isomer-1 and 2 were found to be 4.017±0.868 L/kg, 4.273±1.167 and 24.497±6.339 L/h/kg, respectively. However, over all systemic exposure i.e AUC 0-∞ (h*μg/mL) were found to be high upon IM route of administration of chiral isomer-1 at 20 mg/kg dose ((110.95±14.987)) as compare to compound 1 (racemic) (98.56±9.399) and chiral isomer-2 (20.644±2.977). The time taken for the systemic levels to reduce to half (half-life, $t_{1/2}$) of compound 1 (racemic), chiral isomers 1 and 2 were found to be 13.53±1.70 h, 16.03±2.376 h and 17.11±2.454 h, respectively.

TABLE 7

Time-Mean Plasma concentration profile of Bulk of compound 1 (racemic) as well as Chiral -1 and Chiral-2 compound 1after IM administration at 20 mg/kg dose.

| | Concentration (μg/mL) | | |
|---|---|---|---|
| Time (h) | Compound 1 (racemic) | Chiral isomer-1 | Chiral isomer-2 |
| 0.25 | 2.91 ± 0.95 | 1.678 ± 1.06 | 0.409 ± 0.15 |
| 0.5 | 4.44 ± 0.46 | 2.09 ± 1.65 | 0.7676 ± 0.05 |
| 1 | 3.93 ± 1.2 | 2.576 ± 1.96 | 0.557 ± 0.26 |
| 3 | 3.236 ± 0.24 | 2.56 ± 0.59 | 0.745 ± 0.12 |
| 5 | 2.833 ± 0.32 | 2.463 ± 0.88 | 0.762 ± 0.34 |
| 7 | 2.386 ± 0.53 | 2.1166 ± 0.94 | 0.536 ± 0.17 |
| 9 | 3.213 ± 0.81 | 3.44 ± 0.26 | 0.463 ± 0.37 |
| 24 | 1.736 ± 0.24 | 2.466 ± 0.57 | 0.323 ± 0.04 |
| 30 | 1.656 ± 0.23 | 1.726 ± 0.15 | 0.246 ± 0.12 |
| 48 | 0.262 ± 0.12 | 0.593 ± 0.22 | 0.1693 ± 0.10 |
| 72 | 0.107 ± 0.01 | 0.109 ± 0.04 | 0.0443 ± 0.006 |

TABLE 8

Pharmacokinetic parameters of Bulk compound 1 (racemic), Chiral isomer-1 and Chiral isomer-2 upon IM administration. Data represented as mean ± S.D. (n = 4, each)

| Parameters | Compound 1 (racemic) | Chiral isomer-1 | Chiral isomer-2 |
|---|---|---|---|
| $t_{1/2}$ (h) | 13.53 ± 1.70 | 16.03 ± 2.376 | 17.11 ± 2.454 |
| $T_{max}$ (h) | 0.667 ± 0.288 | 6.33 ± 4.618 | 3 ± 2 |
| $C_{max}$(μg/mL) | 4.62 ± 0.435 | 3.91 ± 0.847 | 0.945 ± 0.143 |
| $AUC_{0-72}$ (h*μg/mL) | 96.45 ± 9.846 | 108.35 ± 15.854 | 19.54 ± 3.260 |
| $AUC_{0-\infty}$ (h*μg/mL) | 98.56 ± 9.399 | 110.95 ± 14.987 | 20.644 ± 2.977 |
| MRT | 17.96 ± 1.567 | 21.019 ± 0.463 | 22.671 ± 4.539 |
| $V_d$ (L/kg) | 4.017 ± 0.868 | 4.273 ± 1.167 | 24.497 ± 6.339 |
| Cl (L/h/kg) | 0.204 ± 0.0196 | 0.182 ± 0.0249 | 0.981 ± 0.130 |

Materials and Methods

Reagents

DMSO was purchased from Sigma (D2650); Mouse-Fibroblast Growth Factor-basic (FGF) was from Sigma (St. Louis, MO), human-VEGF was purchased from (Sigma; V7259), mouse-VEGF was purchased from (Sigma; V4512), hemoglobin (H7379). Phospho-VEGFR2 (Tyr1175) CST; Raf Family Antibody Sampler kit (#2330 CST); anti-CD31 (sc-1506) Santa Cruz Biotechnology. Alexa 488-conjugated goat anti-rabbit IgG secondary antibodies were obtained from (Invitrogen; A27034). Matrigel was purchased from (CORNING; 354230) and hemoglobin from (Sigma; H7379); Sunitinib Maleate, used as a positive control was purchased from (Sigma; 341031-54-7); all other procured chemicals were of the highest grade commercially available.

In Vitro Cell Culture

The human endothelial cell line, HUVEC was purchased from (Himedia, India) at passage 2 and was cultured in complete Dulbecco's Modified Eagle Medium (DMVEM, Himedia, India) supplemented with 10% fetal bovine serum (FBS, Himedia, India) and 1% Penicillin/Streptomycin (Himedia, India) at 37° C. in 5% $CO_2$ and was allowed to attain a confluency rate of 80%-90%. The cultured cells were then used for different experiments.

Capillary-Like Tube Formation Assay

HUVECs (Human Umbilical Vein Endothelial Cells) were seeded onto the pre-coated matrigel (CORNING; 354230) in 96 wells plate at the rate of 11000 cells/well in incomplete ECM basal medium. Control group received vehicle, VEGF at 50 ng/mL as a positive and sunitinib at 50 nM as a negative control were used. Compound 1 at different dose concentrations (10 μM, 5 μM, 1 μM, 800 nM, 500 nM, 250 nM, 100 nM, 75 nM, 50 nM and 25 nM) were employed on seeded HUVECs in incomplete medium. Post 6 h of incubation Calcein-AM (Invitrogen) was added to all the respective groups and then the tubule pattern was observed and photographs were taken using an inverted fluorescent microscope (DM 6000, Leica Microsystems, USA). Relative tubule lengths were measured using Leica Q-Win software version 3.5.1. (Leica Microsystems, Switzerland).

Wound Healing Assay

Endothelial cells were grown inside 6-well plate at a confluency rate of 90%. And then with the help of 200 μL tip a straight line scratch was made in the middle of the grown ECs. After giving a gentle wash with 1×PBS, control group received vehicle in 2.5% FBS media. VEGF at 50 ng/mL as a positive control and sunitinib at 50 nM concentration was used as a negative control. Compound 1 at a dose concentration of 250 nM and 125 nM were used onto the wounded cells to observe its anti-migratory effect. After 0 h, 12 h and 24 h of post treatment the wound closure area was observed and micrographed using an inverted microscope (Olympus, Centre Valley, PA, USA) and were analysed by Image J software. Control well at 100% was used to express inhibition percentage and the assay was performed for three-five times independently.

3D Angiogenesis Assay

Endothelial cells (ECs) were trypsinized and then coated on cytodex beads at the rate of 1500 cells per bead in 5% DMEM medium at 37° C. for 4 h by rotating it gently on IP rotor. Fibrinogen (2 mg/mL) and Aprotonin (40 U/μL) were added to the ECs coated beads and this was subsequently added to the 96 well plate pre-coated with pro-thrombin (10 U/μL) and incubated for 15 min. Vehicle control in 2.5% DMEM media with different doses of Compound 1 (500 nM, 250 nM, 125 nM and 75 nM) were used to observe the anti-angiogenic effect of Compound 1 on 3D angiogenesis pattern. Post 3 days of incubation the results were observed and photographs were taken under inverted microscope (Olympus, Centre Valley, PA, USA) and relative tubule lengths were measured using Leica Q-Win software version 3.5.1. (Leica Microsystems, Switzerland).

Experimental Animals

All experiments were conducted according to international ethical standards with prior approval from the Institutional Animal Ethics Committee (IAEC) [IAEC/2015/129] of CSIR-Central Drug Research Institute (CSIR-CDRI) and Committee for the Purpose of Control and Supervision of Experiments on Animals (CPCSEA). Male Balb/c mice (20-25 g) of aged 8-10 weeks were procured from the National Laboratory Animal Centre (NLAC) of CSIR-CDRI, Lucknow, India. CrTac:NCr-Foxn1$^{nu}$ (athymic nude mice, female, 8-10 weeks) were procured from (Taconic Biosciences, U.S.). Animals were housed under standard environmental conditions of 12 h/12 h light-dark cycle, 23±2° C., ambient temperature and humidity 60-65%, in polypropylene cages. Food, in the form of dry pellets ad libitum, and water were available to the mice.

Matrigel Plug Assay

Compound 1 ability to modulate neovascularization was evaluated by matrigel plug assay, using mouse-VEGF and bFGF (R&D systems, Minneapolis) as stimulus. 300 μL of matrigel (Corning Inc., Corning, NY, USA) were allowed to liquefy at 4° C., supplemented with either VEGF (50 ng/μl), bFGF (50 ng/μl) and heparin (10 mg/mL) as a control or with sunitinib (2 M) as a positive control. All groups and test groups having similar condition along with Compound 1 (750 nM) were carefully mixed with pre-chilled pipette tips to prevent aeration and gelatinization. 4-5 weeks old male Balb/c mice anesthetized with ketamine (100 mg/kg) and xylazine (10 mg/kg) i.p. were injected subcutaneously (s.c.) with matrigel mixtures (0.300 ml) in two locations into the dorsal part. After ten days, mice were euthanized, the dorsal skin retaining the Matrigel implants were dissected. Matrigel plugs were excised after photographs were taken and angiogenic response was evaluated by spectrophotometric measurement of hemoglobin content using the Drabkin's method according to the manufacturer's protocol (Cat no. D5941-6VL; Sigma, St. Louis, Mo). Absorbance was measured at 540 nm and hemoglobin concentration was calculated.

Ear Angiogenesis Assay

Sterile 1×PBS having mouse VEGF (50 ng/mL), bFGF (50 ng/mL), Heparin (10 mg/mL) and sunitinib (2 μM) as a positive control along with compound 1 (750 nM) as a test compound were injected subcutaneously into the ear of 8- to 12-week old male Balb/c mice. Equal volume of 1×PBS with all components except drug was used as a control and was injected in contra lateral ear. After 6 days, mice were sacrificed and the ears were excised and embedded in OCT for cryo-sectioning. Frozen sections of 5 m sizes were immunostained with endothelial cell markers anti CD31 and anti PECAM 1 antibody. This was quantified by total number of blood vessels count.

CAM (Chick Chorio-Allantoic Membrane) Assay

The eggs were incubated horizontally for 3 days at 37° C. in a 60% humidified atmosphere, using a hybridization incubator (combi-SV 12) with one hour scheduled rotation. Post 3 days of incubation, 2-3 mL of albumin was aspirated from the acute pole of the egg to create false air sac directly over the CAM. Post fertilization (Day 8), a fine blade was used to make an approximate 0.5 cc square incision on the eggshell under sterile conditions and the eggshell window fragment was removed to access the CAM beneath. A piece of gelatin sponge embedded in Compound 1 (500 nM and 250 nM) and sunitinib (2 μM) individually were placed on the CAM of the chicken embryo and incubated for 12 days. Sterile parafilm tape was used to seal back the window and the eggs were further incubated without the rotation setting. After 12 days of incubation the CAM integration was assessed by visual inspection and photographed with a digital camera (Canon EOS); the CAM membrane along with gelatin sponge were harvested and its hemoglobin (Hb.) estimation was done by Drabkin's method according to the manufacturer's protocol (Sigma, St. Louis, MO). Absorbance was measured at 540 nm and hemoglobin concentration was calculated.

Immunoblotting

Whole cell lysates of endothelial cells at 6 h of treatment with Compound 1 (250 nM) and sunitinib (50 nM) were prepared using the RIPA-lysis buffer. Proteins were fractionated and resolved on 8% SDS-PAGE gels and transferred onto PVDF membranes (Millipore). After incubation in blocking buffer (5% BSA in 1×TBST) for 1 h the membranes were incubated with primary antibodies specific for p-Akt and p-Src. GAPDH was used as housekeeping and loading control. The blots were then incubated with specific HRP-conjugated secondary antibodies and bands were visualized using ECL (Millipore) on Image Quant (LAS4010) chemiluminescence detection system. The band intensities were quantified using My Image Analysis software.

Orthotopic Tumor Implantation Model

HCT 116 (Human colon cancer cell line) cells were trypsinised and the pellet was dissolved in ice chilled 1×PBS. HCT 116 cells suspension to a concentration of ($1*10^6$) cells in 50 μL PBS solution, were left on ice with occasional agitation. Mice were anaesthetized with ketamine: xylazine (100:10 mg/kg), abdominal side area was shaved and sterilized using 70% ethanol. 50 μL of cell suspension was injected slowly subcutaneously to all the mice. After 2 days, booster dose of tumor cells was injected to all mice as performed previously. The growth of the tumor was measured by using vernier caliper on day 2, 4, 6, 8, 10, 12, 14, 16 18, 20, 23 and presented in the form of tumor volume ($mm^3$)=[4/3*π*(long axis/2)*(short axis/2)]. After attaining a volume of 100 $mm^3$ of tumor size, all mice were distributed equally (n=6–8) in 3 groups of controls received vehicle (Olive oil). Sutent (25 mg/kg) as a positive control was given orally and Compound 1 (25 mg/kg) dissolved in olive oil was injected intra-muscularly for 15 days and the tumor size regression was measured on every alternate day as described previously. Post 15 days of treatment, mice from all groups were sacrificed and tumor was excised out and processed further for immunohistochemistry and molecular analysis.

mRNA Sequence Analysis

High quality intact RNA was isolated using RNeasy Minikit (QIAGEN) from the tumor samples of control and Compound 1 at (25 mg/kg) treated groups and also from the HUVECs treated with compound 1 at different dose concentrations (10 μM, 1 μM, 500 nM, 250 nM) for 6 h>3-4 μg of isolated RNA was sent for mRNA sequence analysis. Heat map graph for the down-regulated and up-regulated genes were generated for each of the respective samples.

Drug Affinity Receptor Target (DART) Analysis

HUVECs with confluency of 80-85% in 100 mm dish were trypsinised and the media was removed and washed twice with 1×PBS. These cells were lysed with lysis buffer at 4° C. Control and treatment group with 100 ag of protein were incubated with vehicle and Compound 1 at a concentration of 10 mM for 15-30 mins at RT with gentle shaking. Then different proteases like thermolysin (10 μg/15 μL) and pronase at (10 μg/L) were added to both the control and treatment groups for 5-10 mins at RT. Digestion was stopped by adding protease inhibitor (20×) at specific interval and allowed to incubate at 4° C. for 10 mins. 6×SDS-PAGE loading dye was added to all the respective samples and heated at 70° C. for 10 mins. SDS-PAGE was performed for the given control and treatment group samples and then the gel was stained with 0.05% Coomassie Brilliant Blue (CBB-R250). After destaining the gel, bands of different molecular weight of treatment and control groups were excised off from the gel and further employed for the protein sequence analysis through LC/MS-MS (Liquid chromatography/Mass spectroscopy).

Statistical Analysis

The results from at least three independent experiments are expressed as mean±SEM. Statistical significance were analyzed using two-tailed Student' T-test or ANOVA was used to test the variability amongst groups. Using graph pad prism software version 5.00.28 (GraphPad Software, Inc., San Diego, CA, USA) all the statistical test was performed. A Probability (P) value less than 0.05 were considered statistically significant.

Abbreviations Used

HUVEC, Human Umbilical Vein Endothelial cell; VEGF, Vascular Endothelial Growth Factor; bFGF, basic Fibroblast Growth Factor; PBS, Phosphate Buffer Saline; BSA, Bovine Serum Albumin; CD31, cluster of differentiation 31; PECAM1, Platelet endothelial cell adhesion molecule; RT, room temperature; LC/MS-MS, Liquid Chromatography/Mass-Mass Spectroscopy.

Advantages of the Invention

1. The main advantage of the present invention is that it provides novel and useful synthetic azirine containing compounds.
2. The advantage of the present invention is that it provides an efficient method of preparation for the above azirine containing compounds.
3. Another advantage of the present invention is the use of these azirine containing compounds as potential anti-angiogenesis agents.

We claim:

1. A pharmaceutical composition comprising the compound of formula (I) or a pharmaceutically acceptable salt thereof (I)

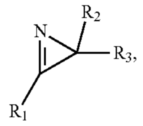

in combination with at least one pharmaceutically acceptable excipient, where:

$R_1$ is selected from the group consisting of alkyl ($C_2$-$C_{12}$), and alkenyl ($C_2$-$C_{12}$); and $R_2$ and $R_3$ are independently selected from the group consisting of —H, —$COOR_4$, cyano, and tetrazole, each of $R_1$, $R_2$, and $R_3$ is further substituted with one or more substituents selected from the group consisting of hydrogen, alkoxy, amino, nitro,

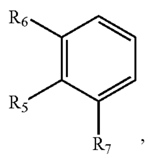 , 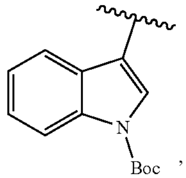 ,

-continued

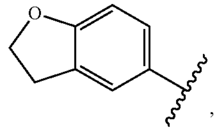,
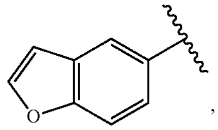,
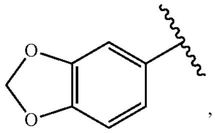,
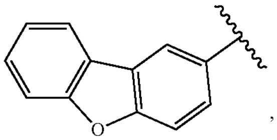,
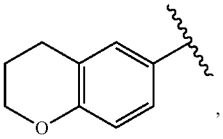,
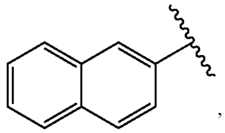,
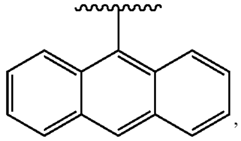, and 5-7 membered hetrocyclic rings having a hetroatom chosen from O, N, or S;

each $R_4$ is selected from the group consisting of alkyl ($C_1$-$C_{12}$), allyl;

$R_5$, $R_6$, $R_7$ are either same or different and selected from the group consisting of H,—OMe, $CH_3$, t-butyl, halogen, —$OCF_3$, —CN, —OBu, vinyl, dimethylamino, and

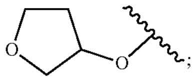 [SMILES: *OC1CCOC1];

each halogen is selected from the group consisting of chlorine (Cl), bromine (Br), fluorine (F), and iodine (I); and $R_5$ and $R_6$ are optionally joined to form a 5 to 6 membered heterocyclic ring, wherein the at least one pharmaceutically acceptable excipient is selected from the group consisting of carboxymethylcellulose, tween 20, polyethylene glycol (PEG 400), dimethyl formamide (DMF), and olive oil.

2. The pharmaceutical composition of claim 1, comprising a pharmaceutically acceptable salt of the compound of formula (I) chosen from basic salts of the compound of formula (I) or acidic salts of the compound of formula (I), wherein:

the basic salts of the compound of formula (I) are selected from the group consisting of aluminum salts, calcium salts, lithium salts, magnesium salts, potassium salts, and sodium salts; and the acidic salts of the compound of formula (I) are selected from the group consisting of hydrochlorides, hydrobromides, hydroiodides, nitrates, sulfates, bisulfates, phosphates, acid phosphates, isonicotinates, acetates, lactates, salicylates, citrates, tartrates, pantothenates, bitartrates, ascorbates, succinates, maleates, gentisinates, fumarates, gluconates, glucaronates, saccharates, formates, benzoates, glutamates, methanesulfonates, ethanesulfonates, benzenesulfonates, and p-toluenesulfonates.

3. A method of treating angiogenesis, the method comprising:

administering the pharmaceutical composition of claim 2 to a subject in need thereof.

4. The method of claim 3, wherein the angiogenesis is an abnormal angiogenesis.

5. The method of claim 3, wherein the angiogenesis pertains to an eye disorder.

6. The method of claim 3, wherein the angiogenesis pertains to macular degeneration or abnormal intraocular pressure.

7. The method of claim 1, wherein the compound according to formula (I) is selected from the group consisting of (i) ethyl 3-(4-methoxyphenethyl)-2H-azirine-2-carboxylate (1):

(1)

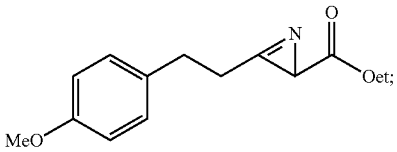

(ii) ethyl 3-(pent-4-en-1-yl)-2H-azirine-2-carboxylate (2):

(2)

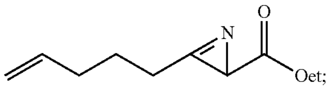

(iii) ethyl 3-dodecyl-2H-azirine-2-carboxylate (3):

(3)

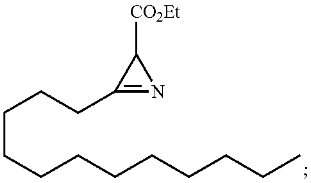;

(iv) ethyl 3-(4-methylpent-3-en-1-yl)-2H-azirine-2-carboxylate (4):

(4)

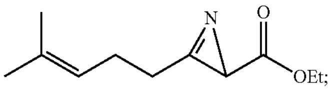

(v) ethyl (E)-3-(4,8-dimethylnona-3,7-dien-1-yl)-2H-azirine-2-carboxylate (5):

(5)

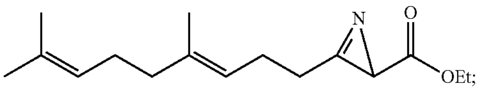

(vi) ethyl 3-phenethyl-2H-azirine-2-carboxylate (6):

(6)

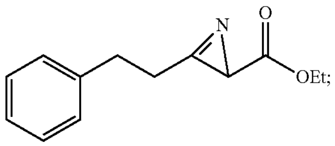

(vii) ethyl 3-(4-methylphenethyl)-2H-azirine-2-carboxylate (7):

(7)

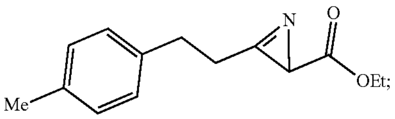

(viii) ethyl 3-(4-chlorophenethyl)-2H-azirine-2-carboxylate (8):

(8)

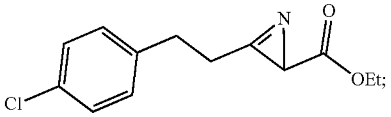

(ix) ethyl 3-(4-(tert-butyl)phenethyl)-2H-azirine-2-carboxylate (9):

(9)

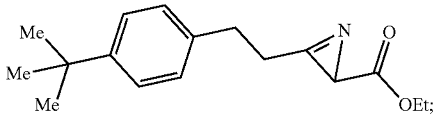

(x) ethyl 3-(4-fluorophenethyl)-2H-azirine-2-carboxylate (10):

(10)

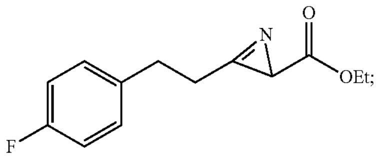

(xi) ethyl (E)-3-(4-phenylbut-3-en-1-yl)-2H-azirine-2-carboxylate (11):

(11)

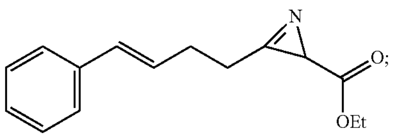

(xii) ethyl 3-(3,4,5-trimethoxyphenethyl)-2H-azirine-2-carboxylate (12):

(12)

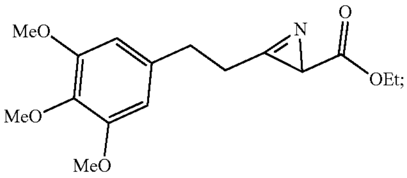

(xiii) ethyl (E)-3-(4-methoxystyryl)-2H-azirine-2-carboxylate (13):

(13)

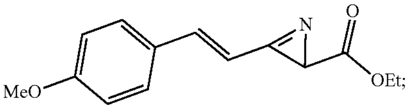

(xiv) methyl 3-(4-methoxyphenethyl)-2H-azirine-2-carboxylate (14):

(14)

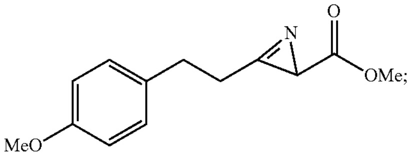

(xv) ethyl 3-(4-bromophenethyl)-2H-azirine-2-carboxylate (15):

(15)

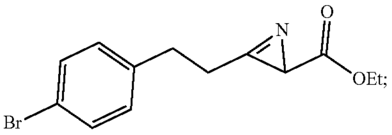

(xvi) ethyl 3-(4-iodophenethyl)-2H-azirine-2-carboxylate (16):

(16)

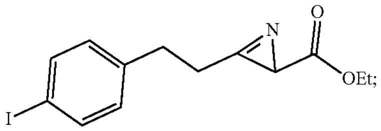

(xvii) tert-Butyl 3-(4-methoxyphenethyl)-2H-azirine-2-carboxylate (17):

(17)

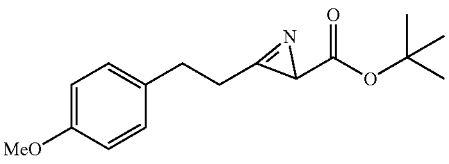

;

(xix) propyl 3-(4-methoxyphenethyl)-2H-azirine-2-carboxylate (19):

(19)

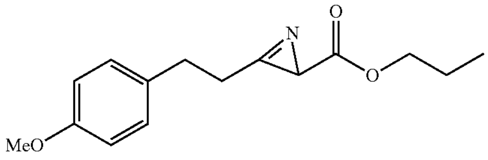

;

(xx) isopropyl 3-(4-methoxyphenethyl)-2H-azirine-2-carboxylate (20):

(20)

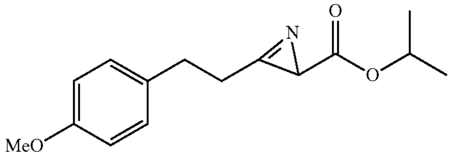

;

(xxi) isobutyl 3-(4-methoxyphenethyl)-2H-azirine-2-carboxylate (21):

(21)

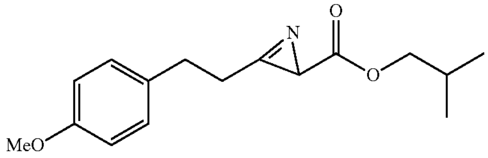

;

(xxii) sec-butyl 3-(4-methoxyphenethyl)-2H-azirine-2-carboxylate (22):

(22)

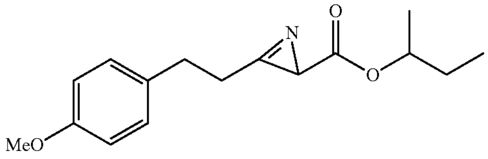

;

(xxiii) pentyl 3-(4-methoxyphenethyl)-2H-azirine-2-carboxylate (23):

(23)

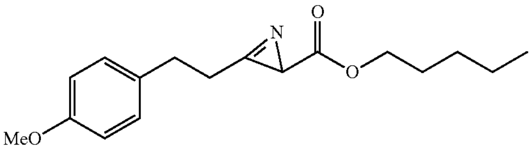

;

(xxiv) isopentyl 3-(4-methoxyphenethyl)-2H-azirine-2-carboxylate (24):

(24)

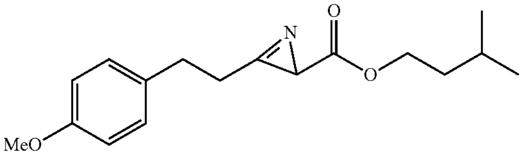

;

(xxvi) allyl 3-(4-methoxyphenethyl)-2H-azirine-2-carboxylate (26):

(26)

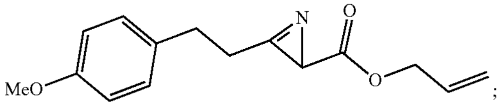

;

(xxvii) ethyl 3-(2-(naphthalen-2-yl)ethyl)-2H-azirine-2-carboxylate (27):

(27)

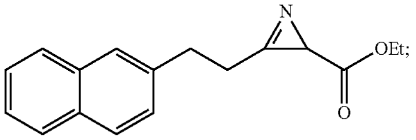

(xxviii) ethyl 3-(4-(trifluoromethoxy)phenethyl)-2H-azirine-2-carboxylate (28):

(28)

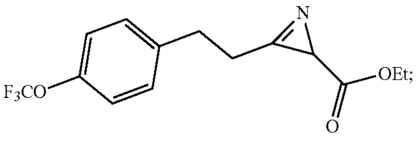

(xxix) octyl 3-(4-methoxyphenethyl)-2H-azirine-2-carboxylate (29):

(29)

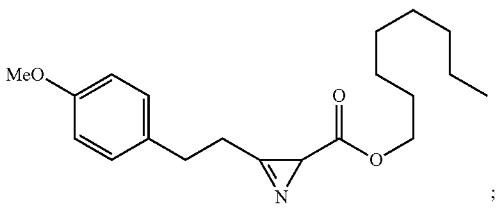

;

(xxx) ethyl 3-(2-(tetrahydrofuran-2-yl)ethyl)-2H-azirine-2-carboxylate (30):

(30)

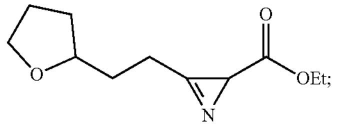

(xxxi) ethyl 3-(4-cyanophenethyl)-2H-azirine-2-carboxylate (31):

(31)

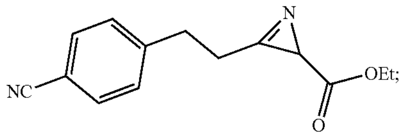

(xxxii) ethyl 3-(4-butoxyphenethyl)-2H-azirine-2-carboxylate (32):

(32)

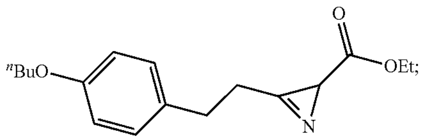

(xxxiii) ethyl 3-(2-(anthracen-9-yl)ethyl)-2H-azirine-2-carboxylate (33):

(33)

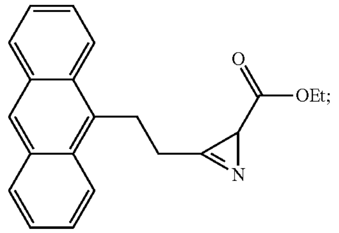

(xxxiv) ethyl 3-(3,4-dimethoxyphenethyl)-2H-azirine-2-carboxylate (34):

(34)

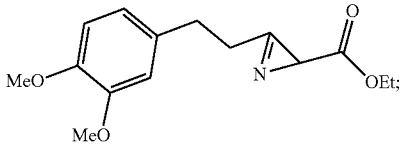

(xxxv) diethyl 3-(4-methoxyphenethyl)-2H-azirine-2,2-dicarboxylate (35):

(35)

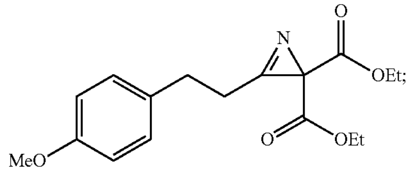

(xxxvi) ethyl 3-(4-vinylphenethyl)-2H-azirine-2-carboxylate (36):

(36)

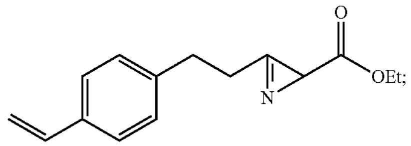

(xxxvii) ethyl-3-(3-(2,3-dihydrobenzofuran-5-yl)propyl)-2H-azirine-2-carboxylate (37);

(37)

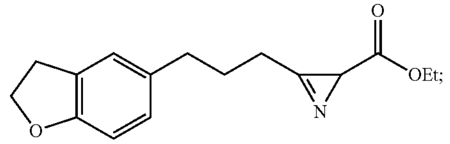

(xxxviii) tert-butyl 3-(2-(2-(ethoxycarbonyl)-2H-azirin-3-yl)ethyl)-1H-indole-1-carboxylate (38):

(38)

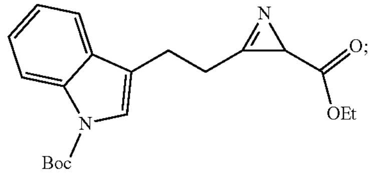

(xxxix) ethyl 3-(2-(2,3-dihydrobenzofuran-5-yl)ethyl)-2H-azirine-2-carboxylate (39):

(39)

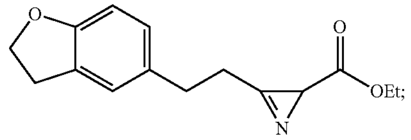

(xl) ethyl 3-(3-(benzofuran-5-yl)propyl)-2H-azirine-2-carboxylate (40):

(40)

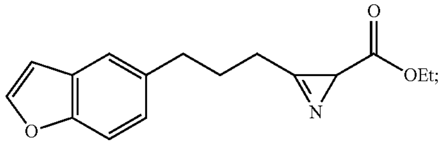

(xli) ethyl 3-(2-(benzo[d][1,3]dioxol-5-yl)ethyl)-2H-azirine-2-carboxylate (41):

(41)

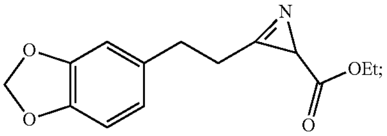

(xlii) ethyl 3-(4-(2,3-dihydrobenzofuran-5-yl)butyl)-2H-azirine-2-carboxylate (42):

(42)

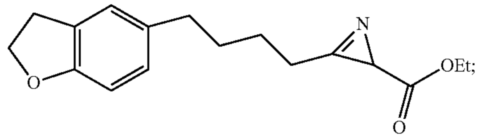

(xliii) ethyl 3-(3-(benzo[d][1,3]dioxol-5-yl)propyl)-2H-azirine-2-carboxylate (43):

(43)

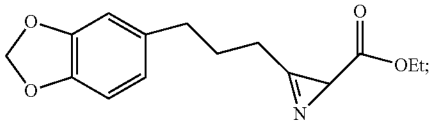

(xliv) ethyl 3-(3-(dibenzo[b,d]furan-2-yl)propyl)-2H-azirine-2-carboxylate (44):

(44)

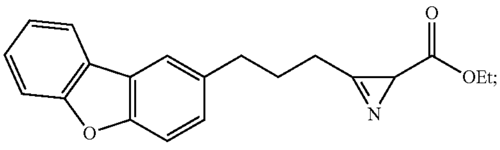

(xlv) ethyl 3-(3-(chroman-6-yl)propyl)-2H-azirine-2-carboxylate (45):

(45)

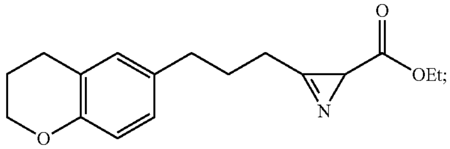

(xlvi) ethyl (E)-3-(4-(dimethylamino)styryl)-2H-azirine-2-carboxylate (46):

(46)

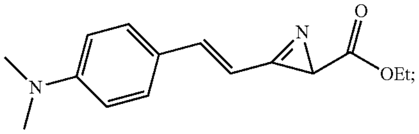

(xlvii) ethyl 3-(4-(dimethylamino)phenethyl)-2H-azirine-2-carboxylate (47):

(47)

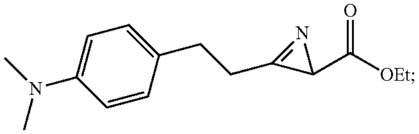

(xlviii) 3-(4-methoxyphenethyl)-2H-azirine-2-carbonitrile (48):

(48)

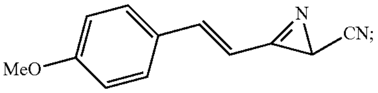

(l) ethyl 3-(4-((tetrahydrofuran-3-yl)oxy)phenethyl)-2H-azirine-2-carboxylate (50):

(50)

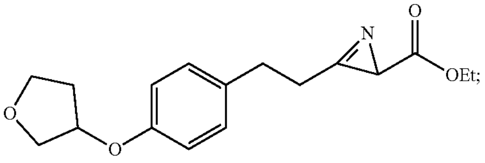

(li) 5-(3-(4-methoxyphenethyl)-2H-azirin-2-yl)-1H-tetrazole (51):

(51)

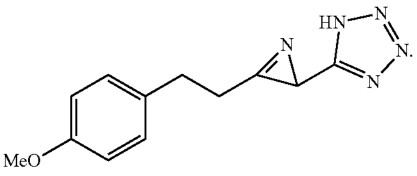

8. The method of claim 1, wherein the compound according to formula (I) is:

(i) ethyl 3-(4-methoxyphenethyl)-2H-azurine-2-carboxylate (1):

(1)

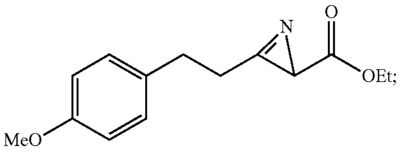

9. A process for the preparation of the parmaceutical composition of claim 1, the process comprising:

(a) treating a beta-keto ester compound of formula (II):

(II)

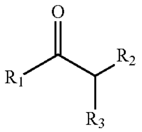

where $R_1$, $R_2$, and $R_3$ are as defined in formula (I), with a hydroxylamine salt and an amine base in alcoholic solvent at temperature from −5° C. to 5° C. for 6 hours to 12 hours to obtain an oxime compound of formula (III):

(III)

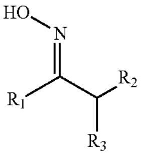

where $R_1$, $R_2$, and $R_3$ are as defined in formula (I) and formula (II);

(b) treating the oxime compound of formula (III) obtained in (a) with p-toluenesulfonic anhydride and an amine base in organic solvent at temperature from −5° C. to 5° C. for 6 hours to 12 hours to obtain a tosyloxime compound of formula (IV):

(IV)

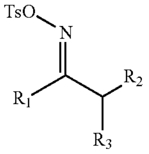

where $R_1$, $R_2$, and $R_3$ are as defined in formula (I) and formula (III); and (c) performing (1) or (2) to obtain the azirine containing compound of formula (I):

(1) treating the tosyloxime compound of formula (IV) obtained in (b) with an amine base in organic solvent at a temperature from −5° C. to 5° C. for 6 hours to 12 hours; or (2) treating the oxime compound of formula (III) obtained in (a) with p-toluenesulfonyl chloride and an amine base in organic solvent at a temperature from −5° C. to 5° C. for 6 hours to 12 hours.

10. The process according to claim 9, wherein the amine base is selected from the group consisting of pyridine, triethylamine, pyrrolidine, and imidazole.

11. The process according to claim 9, wherein:

the organic solvent is selected from the group consisting of toluene, tetrahydrofuran, dioxin, dichloromethane, chloroform, hexane, pentane, heptane, and acetonitrile; and the alcoholic solvent is selected from the group consisting of methanol, ethanol, propanol, butanol, and isopropanol.

* * * * *